(12) United States Patent
Naccarato

(10) Patent No.: US 10,925,782 B2
(45) Date of Patent: Feb. 23, 2021

(54) STAIR TRAVERSING DEVICE

(71) Applicant: QUANTUM ROBOTIC SYSTEMS INC., Toronto (CA)

(72) Inventor: Francesco Naccarato, Toronto (CA)

(73) Assignee: QUANTUM ROBOTIC SYSTEMS INC., Toronto (CA)

( * ) Notice: Subject to any disclaimer, the term of this patent is extended or adjusted under 35 U.S.C. 154(b) by 0 days.

(21) Appl. No.: 16/654,632

(22) Filed: Oct. 16, 2019

(65) Prior Publication Data

US 2020/0093664 A1    Mar. 26, 2020

Related U.S. Application Data

(63) Continuation of application No. 15/778,186, filed as application No. PCT/CA2016/051368 on Nov. 22, 2016, now Pat. No. 10,583,056.
(Continued)

(51) Int. Cl.
*A61G 5/06* (2006.01)
*B62D 57/024* (2006.01)
(Continued)

(52) U.S. Cl.
CPC .............. *A61G 5/061* (2013.01); *A61B 5/023* (2013.01); *B62D 57/024* (2013.01); *B62B 5/02* (2013.01)

(58) Field of Classification Search
CPC ...... A61G 5/061; A61B 5/023; B62D 57/024; B62B 5/02
See application file for complete search history.

(56) References Cited

U.S. PATENT DOCUMENTS 3,304,094 A    2/1967 Wenger
3,438,641 A    4/1969 Bradley
(Continued)

FOREIGN PATENT DOCUMENTS

CN    101954936 A    1/2011
CN    102283750 A    12/2011
(Continued)

OTHER PUBLICATIONS

Search Report and Written Opinion issued for PCT/CA2016/051368 dated Jan. 27, 2017, 6 pages.
(Continued)

*Primary Examiner* — Kevin Hurley
*Assistant Examiner* — Marlon A Arce
(74) *Attorney, Agent, or Firm* — Rothwell, Figg, Ernst & Manbeck, P.C.

(57) ABSTRACT

A stair traversing device comprising a payload body for transporting a payload, a step frame, and a mechanism between the step frame and the payload body to move the step frame relative to the payload body along a cyclical path. The mechanism drives a movement of one of the payload body and the step frame along a first segment of the cyclical path from a retracted configuration to an extended configuration, and drives a movement of the other one of the payload body and the step frame along a second segment of the cyclical path back into the retracted configuration. The payload body and the step frame are configured to remain fixedly in position on a stair when the other one of the payload body and the step frame is moved. The mechanism is configured to maintain the relative orientation between the payload body and the stair.

14 Claims, 38 Drawing Sheets

Related U.S. Application Data

(60) Provisional application No. 62/258,741, filed on Nov. 23, 2015.

(51) Int. Cl.
*A61B 5/023* (2006.01)
*B62B 5/02* (2006.01)

(56) References Cited

U.S. PATENT DOCUMENTS

| | | | |
|---|---|---|---|
| 3,592,282 A | 7/1971 | Soileau | |
| 4,569,409 A * | 2/1986 | Kluth | A61G 5/061 180/8.2 |
| 6,695,084 B2 | 2/2004 | Wilk | |
| 7,677,345 B2 | 3/2010 | Hosoda | |
| 8,418,787 B2 | 4/2013 | Bouhraoua et al. | |
| 8,596,388 B2 | 12/2013 | Bouhraoua et al. | |
| 8,776,917 B2 | 7/2014 | Bouhraoua et al. | |
| 10,434,028 B2 * | 10/2019 | Barto | A61H 3/00 |
| 2003/0127259 A1 | 7/2003 | Logstrup | |
| 2014/0265171 A1 | 9/2014 | Ramakrishnan | |
| 2014/0326521 A1 | 11/2014 | Hacikadiroglu et al. | |

FOREIGN PATENT DOCUMENTS

| | | |
|---|---|---|
| CN | 205417720 U | 8/2016 |
| CN | 105996910 A | 10/2016 |
| DE | 2014011235 A1 | 2/2016 |
| DE | 102014011235 A1 | 2/2016 |
| EP | 1476343 B1 | 11/2004 |
| ES | 2380465 A1 | 5/2012 |
| JP | H0585364 A | 4/1993 |
| JP | H06206547 A | 7/1994 |
| JP | H07267094 A | 10/1995 |
| JP | 2007153521 A | 6/2007 |
| KR | 20030040992 A | 5/2003 |

OTHER PUBLICATIONS

Escalera Step Detection Safety System. http://handtrucks2go.com/Escalera-Step-Detection-Safety-System.html. Retreived from the Internet on Aug. 15, 2018, 3 pages.

YouTube video clip entitled "Stairclimber Scalamobil," uploaded on Jan. 22, 2009 by user "Michael Urso". Retrieved from Internet: <https://www.youtube.com/watch?v=m7DmqZ-NLOE>.

* cited by examiner

Stair Traversing Device

Stair Traversing Device

FIG. 3B   FIG. 3C

Stair Traversing Device

Stair Traversing Device

Stair Traversing Device

Stair Traversing Device

Stair Traversing Device

Stair Traversing Device

Stair Traversing Device

Stair Traversing Device

Stair Traversing Device

Stair Traversing Device

Stair Traversing Device

Stair Traversing Device

Stair Traversing Device

Stair Traversing Device

Stair Traversing Device

Stair Traversing Device

Stair Traversing Device

FIG. 23A   FIG. 23B

Stair Traversing Device

Stair Traversing Device

Stair Traversing Device

Stair Traversing Device
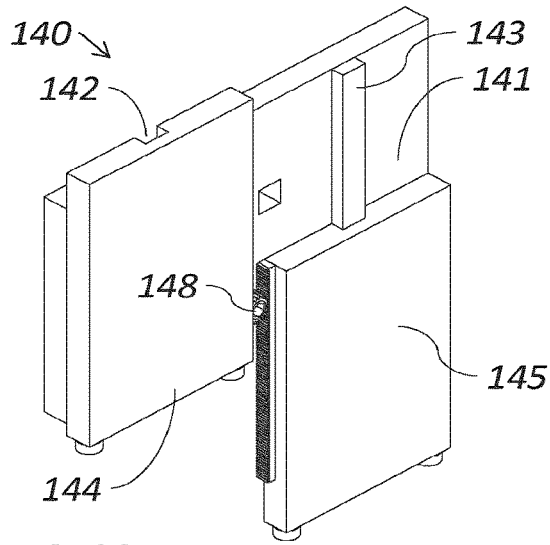
FIG. 28A
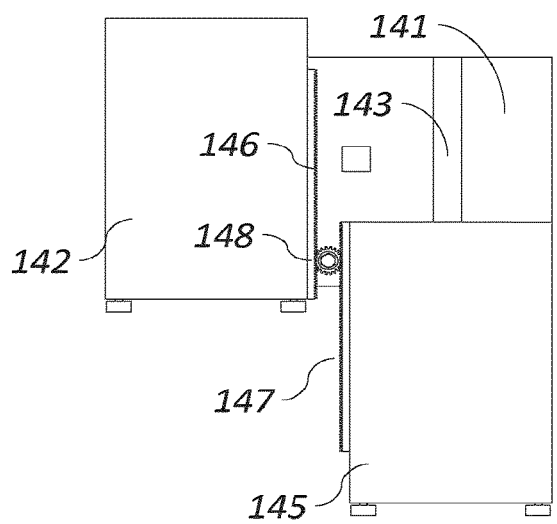
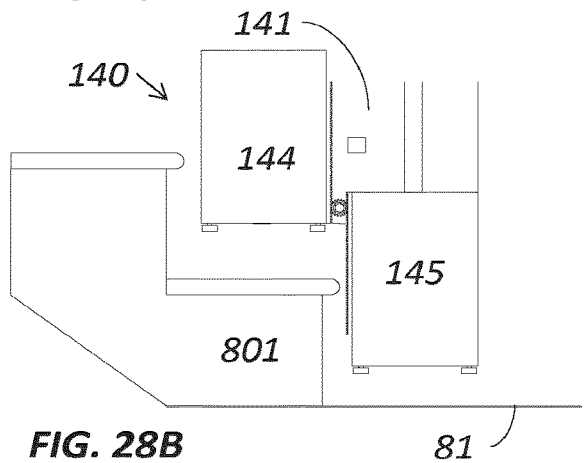
FIG. 28B
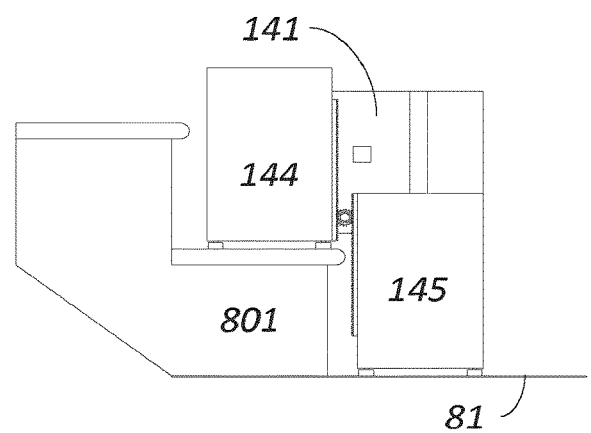
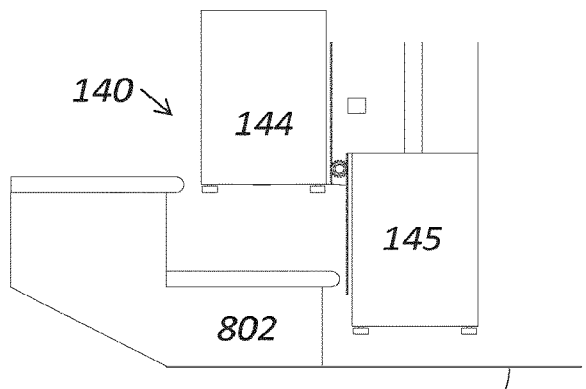
FIG. 28C
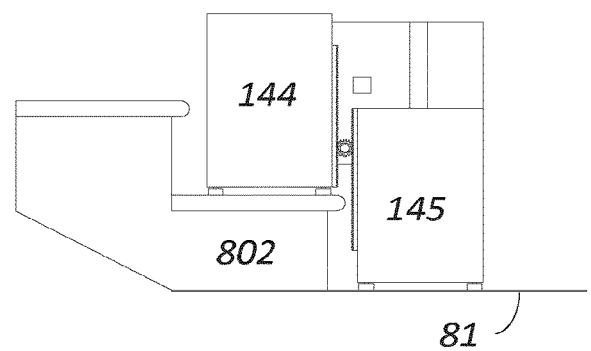

Stair Traversing Device

Stair Traversing Device

Stair Traversing Device

Stair Traversing Device

Stair Traversing Device

Stair Traversing Device

Stair Traversing Device

Stair Traversing Device
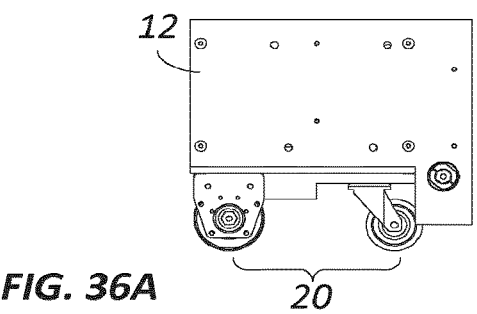
*FIG. 36A*
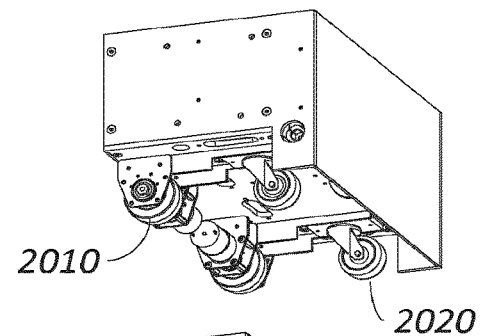
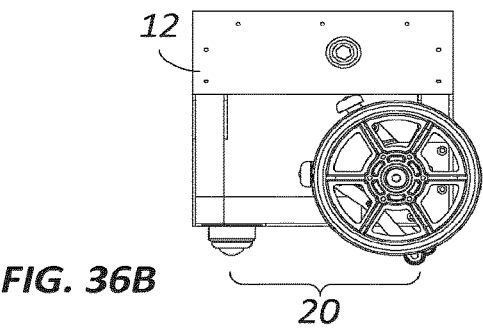
*FIG. 36B*
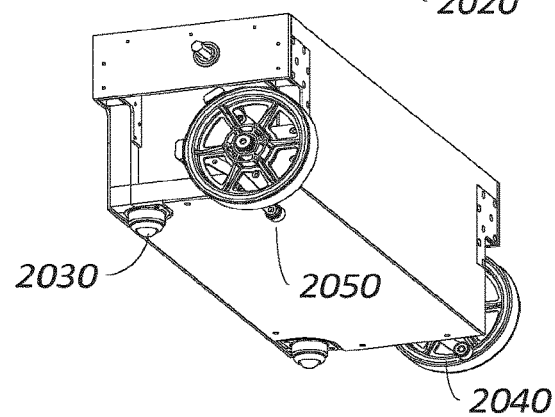
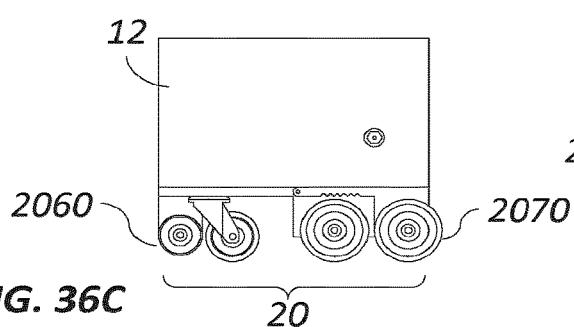
*FIG. 36C*
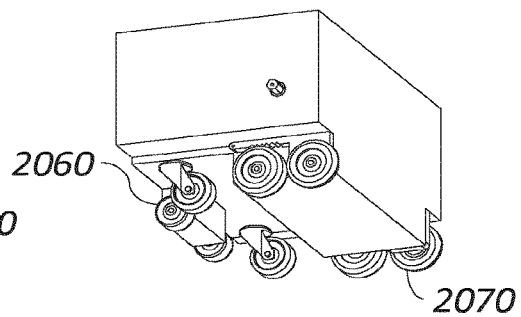
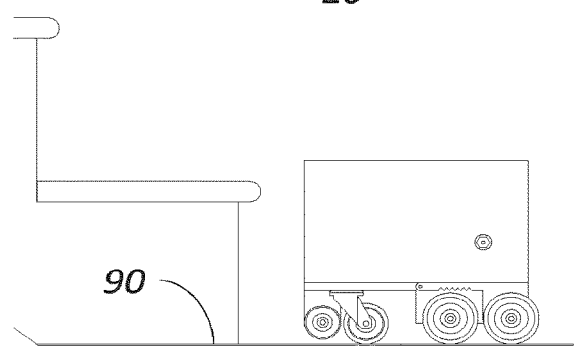
*FIG. 36D*
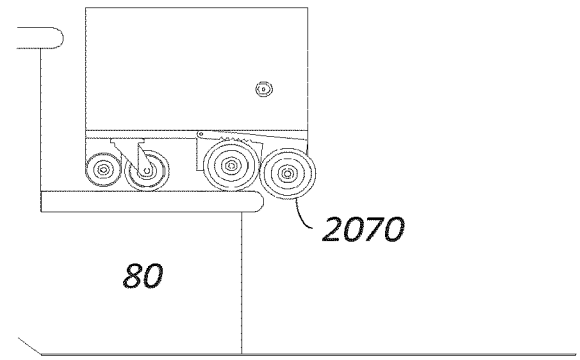

Stair Traversing Device

Stair Traversing Device

Stair Traversing Device

Stair Traversing Device

STAIR TRAVERSING DEVICE

CROSS REFERENCE TO RELATED APPLICATION

This application is a continuation of U.S. patent application Ser. No. 15/778,186 filed on May 22, 2018, which is a 35 U.S.C. 371 National Phase Entry Application from PCT/CA2016/051368 filed Nov. 22, 2016, which claims the benefit of Provisional Application Ser. No. 62/258,741 filed on Nov. 23, 2015, the disclosure of which are incorporated herein in their entirety by reference.

FIELD OF THE INVENTION

The present invention relates to a mechanical device that is capable of traversing stairs, and particularly a stair traversing device which utilizes the repeated cyclical motion of a step frame assembly that is partially shaped to conform to the profile of a stair step.

BACKGROUND OF THE INVENTION

Within both industrial settings and everyday households, carrying heavy loads up and down stairs is cumbersome and may even pose a potential safety hazard. Unfortunately, existing solutions for traversing stairs have significant shortcomings.

Material handling devices, such as hand trucks, carts and dollies, are frequently used to assist in carrying loads up and down stairs. However, these devices require the payload to be tilted in order to balance the center of mass, and must be stabilized by the human operator.

Similarly, mobility devices for the elderly, disabled or infirm, such as wheelchairs and motorized scooters, are generally designed to operate on a level surface. To traverse stairs, these devices generally require ramps or the assistance of another person.

Stairs are a significant barrier for mobile robots, particularly those intended for domestic applications. For example, the Roomba vacuum cleaner, which is intended to automate the task of vacuuming, lacks the ability to traverse stairs and must be manually carried from one level of the house to another. Other robots rely on tank-like treads, which require the payload to tilt, or use anthropomorphic legs, which necessitate an extremely complex and expensive solution.

Presently, various designs of stair traversing devices with level-keeping capabilities have been put forth in the prior art. Some are implemented in the form of coordinated walking elements or a series of articulating wheel sets, while others are implemented in the form of a robot with feedback control.

US Patent Publication No. US 2014/0326521 discloses one such solution that relates to a transport device comprising a load carrying body, at least one central walking element, a first side walking element and a second side walking element. At least one central walking element is arranged in-between the two side walking elements. The walking elements are arranged at the load carrying body in a manner to be capable of moving up and down with respect to the load carrying body, wherein the side walking elements can move up and down independently from the central walking elements by means of vertical actuators. Also, the walking elements are arranged at the load carrying body in a manner to be capable of moving back and forth in horizontal direction with respect to the load carrying body, wherein the walking elements can move back and forth independently from the central walking elements by means of horizontal actuators.

U.S. Pat. No. 7,677,345 discloses another solution in the form of a mobile, wheeled robot. In particular, the '345 Patent discloses a moving robot of narrow footprint, having quick traveling performance on a plane-surface, as well as an anti-tumbling function. The robot is able to cope with travel over surfaces with level differences by means of its wheel arrangement. In front and rear of main driving wheels, each being controlled through the inverted pendulum control, are disposed supporting legs, tips of which can be lifted up and down, wherein the tips of the supporting legs are positioned to keep a predetermined distance between a traveling surface, when running on the inverted two-wheels travel, and the supporting legs are fixed or either one in the fall-down direction is thrust out into the fall-down direction, so as to protect it from falling down. Further, upon the basis of detection information of floor-surface distance sensors and side-surface distance sensor, which are provided at the tips of the supporting legs, the robot senses an existence of a level difference and/or an inclined surface, so as to let the supporting legs to escape from the level difference and/or the inclined surface, and holds the position of gravity center thereof, stably, through other one of the supporting legs, being landed on the ground, and the main driving wheels; thereby enabling to travel over the level difference and the inclines surface.

Yet another stair-climbing apparatus is disclosed in U.S. Pat. No. 8,776,917. The patent discloses a stair-climbing apparatus that has a series of articulating wheel sets extending below a load carrying platform. All of the wheel sets are vertically adjustable to negotiate stairways and similar changes of elevation. The lead wheel set is fixed longitudinally relative to the platform, while following wheel sets are longitudinally adjustable to adjust for the pitch or slope of different stairways. The apparatus uses sensors e.g., mechanical, infrared, ultrasonic, etc. to detect the presence of the stair risers and their height, control of the assembly being accomplished by a control circuit on board the machine. The wheel sets are raised and lowered independently of one another by pantograph mechanisms extending between the platform and the wheel sets. The horizontally adjustable wheel sets are positioned by a longitudinally disposed rack on the platform.

The devices disclosed in the prior art, such as the ones identified above, may rely on either a plurality of moving components that may be driven by multiple actuators. Further, the prior art devices may require active control involving complex control logic in order to traverse the stairs while remaining level. These features generally result in large, complex electro-mechanical devices that require multiple moving components working under synchronized control. Greater complexity generally increases the likelihood of error and failure, and typically results in higher manufacturing and maintenance costs. Thus, there is a need for smaller, simpler and purely mechanical stair traversing device that remains stable and level without the need for active electronic control.

SUMMARY OF THE INVENTION

General Description

To at least partially overcome the stated disadvantages of previously known devices, the present invention, in one embodiment, provides a device comprising a payload body capable of carrying a load in a stable, nominally level orientation that relies on the cyclical motion of a uniquely shaped step frame, facilitated by one or more actuators, in traversing stairs, thereby maintaining a stable, level orientation without the need for active control.

In particular, the stair traversing device comprises a payload body that possesses the capability to travel over nominally horizontal surfaces. Such capability may be provided by wheels, tracks, legs with feet, or any other suitable movement means. The payload body comprises a main body that may contain actuators, control logic, power sources, etc. The actuators may be motorized or human powered. The payload body also comprises a load carrying surface upon which a load may be carried in a nominally level manner.

The stair traversing device further comprises a step frame, which may consist of a single body, multiple bodies connected by a structure, or separate multiple bodies moving in unison. The step frame is characterized by a main body portion and an overhanging portion, which, in at least one embodiment, form at essentially a right angle so as to conform to the outer shape of a stair step. The overhanging portion extends from the main body portion of the frame from the side that faces the stairs, and is at a height that is at least capable of clearing the next one or multiple stair steps.

The step frame is attached to the payload body via a mechanism comprising a non-rotating connection that permits linear translation of the step frame in either or both of the horizontal and vertical axes while preventing any rotational movement relative to the payload body. The mechanism also comprises a cyclical motion mechanism that is connected to the step frame and causes the frame to move along a cyclical path relative to the payload body. The non-rotating connection prevents the frame from rotating while traversing the cyclical path. The non-rotation connection and the cyclical motion mechanism may be distinct features of the mechanism, or may be combined into the same feature. The translational movement of the frame along this closed path is repeated in a cyclical manner for each stair step. The cyclical motion mechanism may be driven by one or more actuated inputs, either in the form of motorized or manually-operated actuators. The traversal of the cyclical path is reversed when the direction of traversal of the stairs is changed from climbing to descending.

Stair Traversing Method

To execute the cyclical motion to traverse up stairs, the stair traversing device approaches and makes contact with the first step, all the while its weight is fully supported by the payload body.

Next, from this initial retracted configuration, the cyclical motion begins as the step frame descends so that the bottom portion of the frame makes contact with the floor, and another portion of the step frame, preferably the overhanging portion, makes contact with the intended step to be cleared.

The weight of the device is then transferred from the payload body to the step frame as the payload body ascends to a height that is at least greater than the level of the step intended to be cleared.

Then, the payload body advances primarily horizontally until the entire payload body is above the tread of the step intended to be cleared. The payload body then descends until the bottom contacts the tread of the step. The device is in its fully extended configuration.

The weight is transferred back from the step frame to the payload body, which is now positioned on top of the step intended to be cleared.

The step frame is then lifted to clear the one or more steps upon which the payload body rests. After clearing the height of the one or more steps, the step frame again translates primarily horizontally until the device returns to its retracted configuration, thus completing the cyclical motion. The entire process is repeated for the subsequent steps.

During the cyclical motion described above, it is to be noted that the device, with or without payload, remains statically stable throughout the climbing sequence. Particularly, when the weight of the device is supported by the step frame, the device remains stable by means of the frame's contact against the step, throughout the entire horizontal travel of the center of gravity. When the weight is transferred back onto the payload body once it is on top of the next step, the center of gravity shifts to reside fully within the support base of the payload body again. Preferably, the frame is relatively light-weight compared to the payload body, so that changes in its horizontal position have a comparatively small impact on the position of the center of gravity for the entire system.

To traverse down a flight of stairs, the above climbing sequence is performed essentially in reverse order. In particular, upon detection of the first edge of the top step, while the weight rests with the payload body, the step frame translates primarily horizontally until the bottom of the step frame has travelled sufficient distance greater than the length of one or more steps intended to be cleared. Then the step frame is lowered until the frame makes contact with a step. Then the weight is shifted from the payload body to the frame as the payload body is translated primarily horizontally. The payload body then descends until it makes contact with the step that the step frame is resting upon. The weight of the device is transferred back onto the payload body and the step frame translates further to return to its initial position relative to the payload body.

Payload Body

Accordingly, in one embodiment, the present invention comprises a payload body containing mechanism for rotating a drive shaft that operates the cyclical motion mechanism. The payload body further comprises a movement support mechanism for movement on nominally flat surfaces.

In another embodiment, the payload body may be a mobile robot containing sensors, control logic, power sources.

In another embodiment, the payload body may be teleoperated by an operator.

In another embodiment, the payload body may be a hand truck that is manually operated by a human operator.

In another embodiment, the payload body may be a wheelchair.

Mechanism

Non-Rotating Connector in Guide Slot

In one embodiment, the mechanism is fixedly attached to the sides of the payload body. The non-rotating connection may comprise a square lug that slidingly engages the parallel horizontal sides of a rectangular guide slot in a carriage, which prevents the lug from rotating as it moves along the guide slot. The carriage in turn slidingly engages with parallel vertical rails in the main body of the mechanism. The cyclical motion mechanism may be implemented by way of four sprockets connected by a chained loop with the drive shaft driving one of the sprockets, and with the lug rotatably attached to one of the chain links. When cyclical motion mechanism is activated, the non-rotating connection executes a rectangular-shaped cyclical path that corresponds to the shape of the chained loop.

Non-Rotating Carriage Assembly

In another embodiment, the non-rotating connection may consist of a carriage slidingly engaged via a set of rollers to one or two vertical rails affixed to the main body of the mechanism. Concurrently, another set of rollers permits a horizontal rail to slide horizontally relative to the carriage. The horizontal rail may comprise at least two attachment points to which the step frame would be fixedly attached.

Chain Loop Mechanism

In another embodiment of the mechanism, the non-rotating connection may be implemented as a non-rotating carriage assembly while the cyclical motion mechanism may be implemented by way of four sprockets connected by a chained loop with the drive shaft driving one of the sprockets.

In another embodiment, the cyclical motion mechanism may be implemented by two sets of chain-and-sprocket loop assemblies, one for each of the vertical and horizontal directions of movement. In such embodiment, one or more actuators may be needed to drive the chain-and-sprocket loop assemblies.

Looped Rack Mechanism

In another embodiment, the cyclical motion mechanism may comprise a driven toothed pinion configured to traverse a toothed rack forming a closed planar loop. The pinion may be restrained to the toothed rack by various means. The step frame may be connected to the rack. As the pinion traverses around the toothed rack, the step frame may be restrained by a non-rotating connection in the form of a non-rotating carriage assembly, causing the frame to translate in a cyclical path that coincides with the shape of the loop formed by the toothed rack.

In another embodiment, the pinion may be restrained against the toothed rack by a constraint mechanism comprising a plurality of pins on a base plate. At least one of the pins is in contact with the inner surface of the toothed rack, opposite of the toothed surface, while at least one of the pins is in contact with the outer surface of the toothed rack such that, together, the inner and out pins restrains the pinion connected to the base plate to the toothed rack.

Rotary Crank Mechanism

In another embodiment, the cyclical motion mechanism may consist of a rotary crank arm. One end of the crank may be turned by a drive shaft while the other end may be connected by a pin to the step frame. The frame may be constrained from rotating by way of a non-rotating carriage assembly. The resulting cyclical motion is circular.

Non-Rotating Hub Mechanism

In another embodiment, the cyclical motion mechanism and the non-rotating connection may be combined into a rotary crank arm mechanism. A first hub, concentric with the drive shaft of the crank arm, is non-rotatably fixed to the payload body. A second hub is rotatably connected to the end of the crank arm by a bearing and a short axle. The second hub is non-rotatably affixed to the step frame. A first rotating apparatus or first sprocket is concentric with and fixedly attached to the first hub, while a second rotating apparatus or second sprocket is concentric with and fixedly attached to axle of the second hub. A connecting apparatus, such as a chain loop connects the first and second sprockets. When the crank arm turns by means of the drive shaft, the second hub moves in a circular path but is prevented from rotating relative to the first hub, thus providing a non-rotating connection to the step frame.

In another embodiment, the sprockets and chain loop described above may be replaced with pulleys and a belt, respectively.

In another embodiment, the sprockets and chain loop described above may be replaced with an odd number of intermeshing gears.

Double Crank Arm Mechanism

In another embodiment, the cyclical motion mechanism may be implemented using a double crank-arm mechanism. The drive shaft rotates a primary crank arm. A primary non-rotating apparatus or pulley, concentric with the drive shaft of the primary crank arm, is non-rotatably fixed to the main body of the mechanism. A secondary rotating apparatus or pulley is connected to the primary pulley through a connecting apparatus or belt. A second crank arm is connected to the second pulley and is used to connect to the step frame. The ratios between the diameters of the pulleys and lengths of the crank arms are configured so that the cyclical path generated is a hypotrochoid path.

Step Frame

Each mechanism is connected to a step frame, which may consist of a single body, multiple similar bodies connected by a rigid structure, or multiple similar bodies moving in unison by means of interconnected mechanisms.

Fixed Geometry

In one embodiment, a step frame with a fixed geometry comprises a main body with an overhanging portion that extends from a height that is at least greater than the height of a single step. The overhanging portion and the main body portion of the step frame form at essentially a right angle to conform to the shape of a step. The main body portion and the overhanding portion may comprise features, such as support feet or friction pads, for making load-bearing contact with each the steps.

In another embodiment, the step frame's main body may be essentially "L" shaped with an overhanging portion extending from a height that is at least greater than the height of a stair step.

Variable Geometry

The step frame may have a variable geometry. In one embodiment, the step frame may include a fold-away overhanging portion that is deployed before ascending or descending a step.

In another embodiment, the step frame may have an upper portion and a lower portion connected by a sliding rail that permits the lower portion to slide horizontally, thus allowing the step frame to convert from a "climbing" configuration to a "descending" configuration without the need to change direction.

Level Finding

The step frame may possess a level-finding capability. In one embodiment, the level finding capability may be realized as a step frame consists of a main body with two vertical rails attached. Two frame panels slidingly engage the two vertical rails. The surfaces of the panels facing each other may each include a toothed rack such that the two panels may be connected by a toothed pinion gear fixed upon the back frame. When the main body is lowered, one or the other panel makes first contact with either the upper or lower step. Then, the two panels may move in opposite vertical directions such that one of the panels is lowered, and the other panel raised, until both panels make contact with both steps.

In another embodiment, the level finding capability may be realized through a four-bar mechanism where two horizontal bars may be non-rotatably connected, at both ends, to support feet. The four bar mechanism may be connected, preferably near the center of the horizontal bars, to the main body of the mechanism, which is connected to the payload body. The horizontal bars may rotate about the connection point to the main body to raise or lower the front support feet until it makes contact with the next step.

In another embodiment, the level finding capability may be implemented using a toothed rotary pivot. As the step frame descends onto a step, its freedom of rotation allows a front leg and a lower leg to simultaneously contact the both of the next level surface and the current level surface respectively. When the main body descends further, a toothed wedge clamps onto the pivot, preventing any further rotation.

In other embodiment, the level finding capability is achieved by a front leg that is free to move vertically relative to the main frame body by means of a vertical channel, until a locking pin engages a toothed surface on the front leg. The locking pin is mechanically linked by a pivot to a lower leg. As the main frame body descends, the front leg makes contact with the next level first and when the lower leg eventually makes contact with the current level, the locking pin engages and makes contact with the toothed surface, locking the front leg into position.

Other embodiments of the above locking pin configuration may be implemented using an electro-mechanical switches and actuators to trigger the locking pin when all legs have made contact with their respective levels.

Multiple Steps

In another embodiment, the step frame may be able to traverse multiple stairs during one cyclical motion by having the overhanging portion extending from the main body of the step frame at a height that is at least greater than the height of a plurality of steps.

ALTERNATIVE EMBODIMENTS

The configuration of the payload body relative to the step frame and the mechanism may vary. In one embodiment, the stair traversing device employs a step frame consisting of two symmetric bodies on either side of the payload body.

In another embodiment, the stair traversing device may employ a step frame consisting of only one central body, whereby the payload body may be a three-sided frame with a mechanism attached to the two vertical interior surfaces of the payload body. A step frame, of sufficient width to support the weight of the device and any possible load, is attached, on both of its sides to the mechanisms such that at the highest point of the cyclical motion, the step frame would not be obstructed by the top of the payload body.

In another embodiment, the present invention may be human powered to either or both of the flat surface movement and the cyclical motion of the step frames.

In another embodiment, the movement support mechanism of the payload body may possess braking features which, upon detecting close proximity to the edge of a step, will prevent or resist further movement of the payload body towards the edge. These braking features may be mechanical or electro-mechanical in nature.

In another embodiment, the payload body may include additional auxiliary stability arms that react against features of the same step or a different step to maintain balance.

BRIEF DESCRIPTION OF THE DRAWINGS

Further aspects and advantages of the invention will appear from the following descriptions taken together with the accompanying drawings, in which:

Parts of the Device

FIG. 3b shows a perspective view of the payload body show in FIG. 3a carrying a load;

FIG. 3c shows a side view of the payload body carrying a load on steps;

FIG. 6b shows an exploded perspective view of the mechanism depicted in FIG. 6a.

Stair Traversing Method

Figure 1:
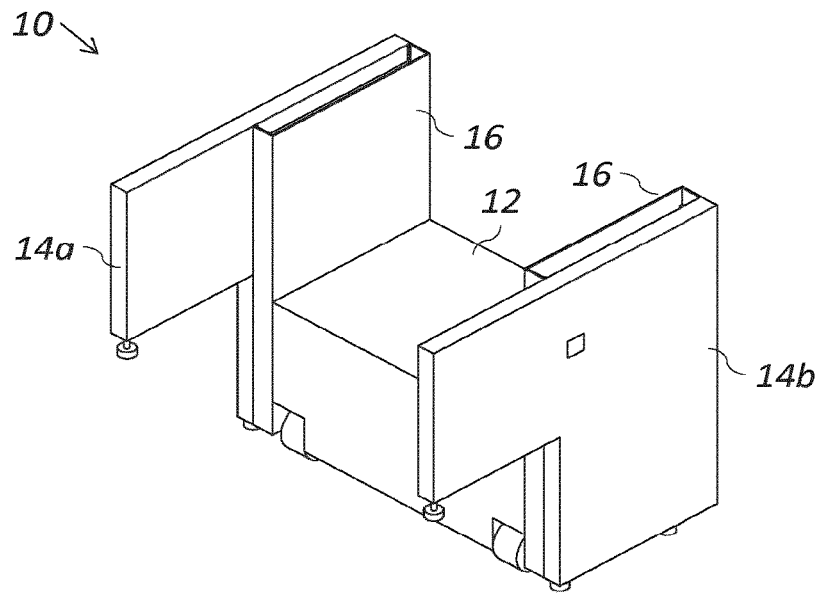
FIG. 1 shows a perspective view of a stair traversing device in accordance with one embodiment of the invention.
Figure 6A:
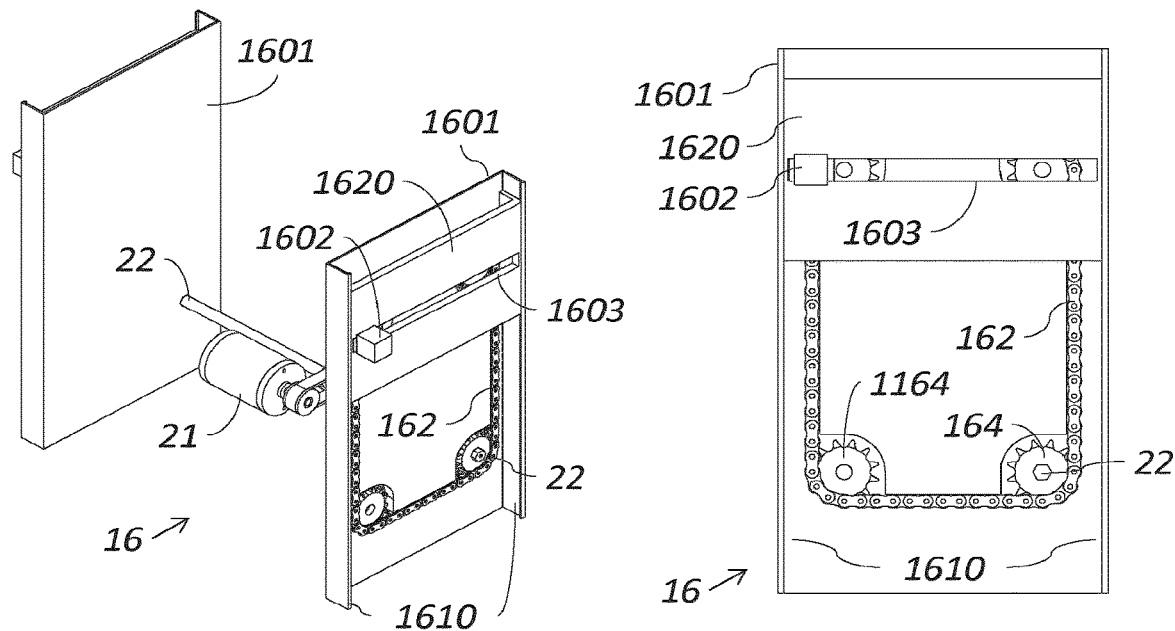
FIG. 6a shows a perspective and side views of one embodiment of the mechanism.
Figure 6B:
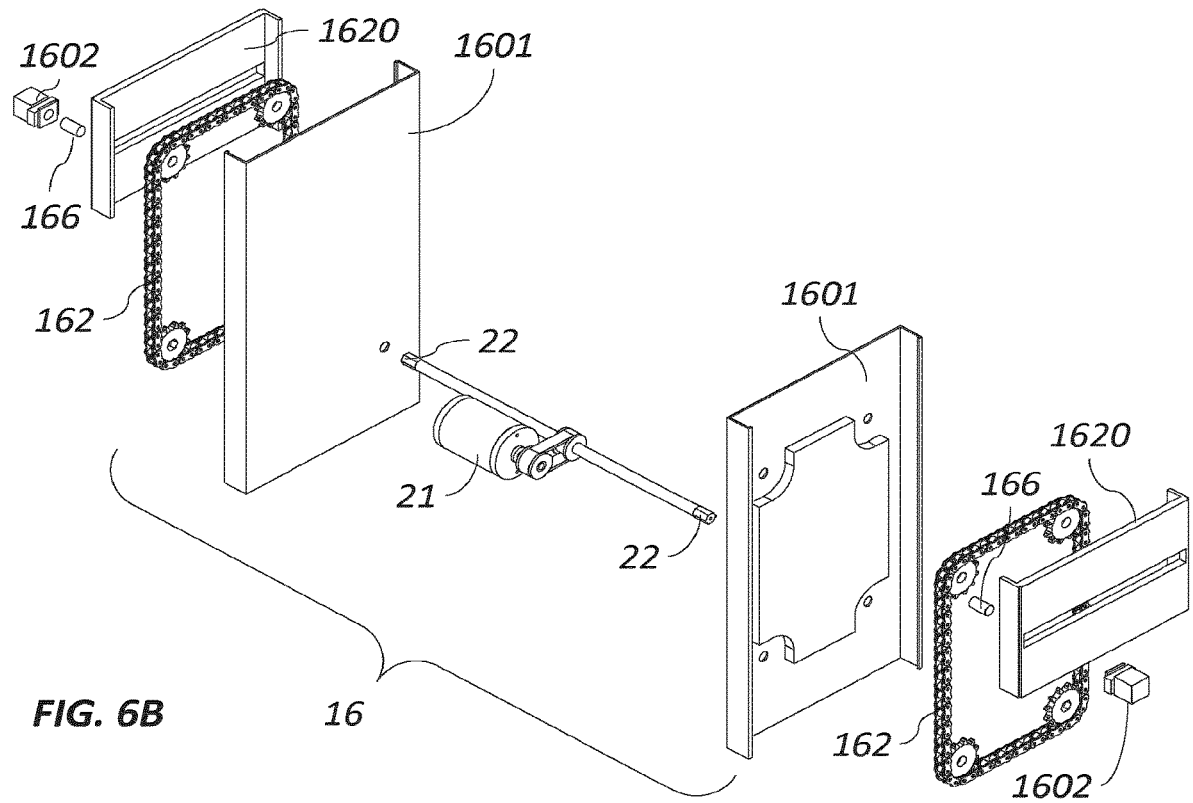
Figure 7A:
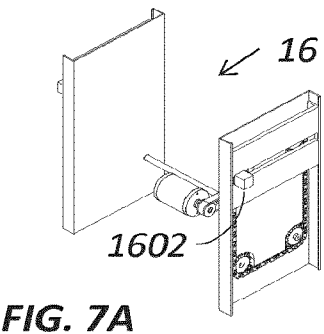
Figure 7A:
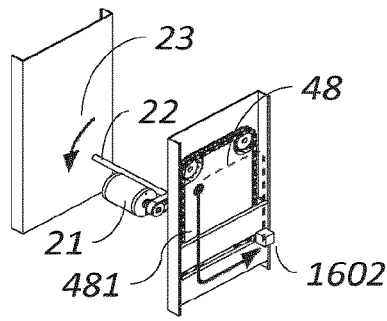
Figure 7A:
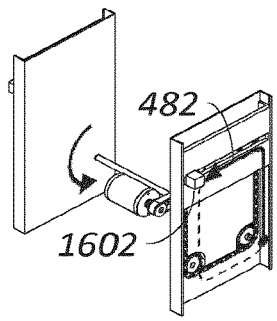
Figure 7B:
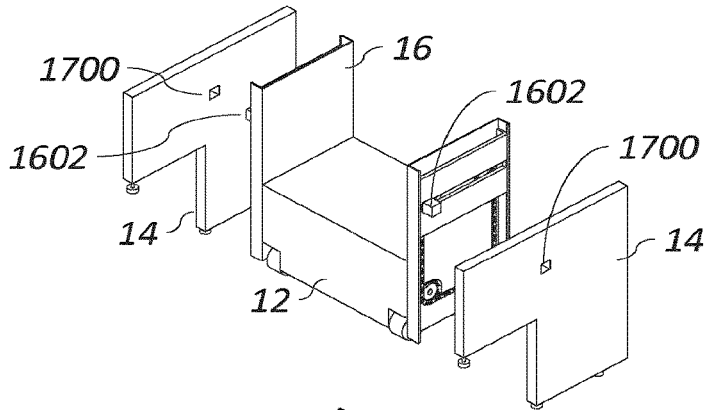
Figure 7C:
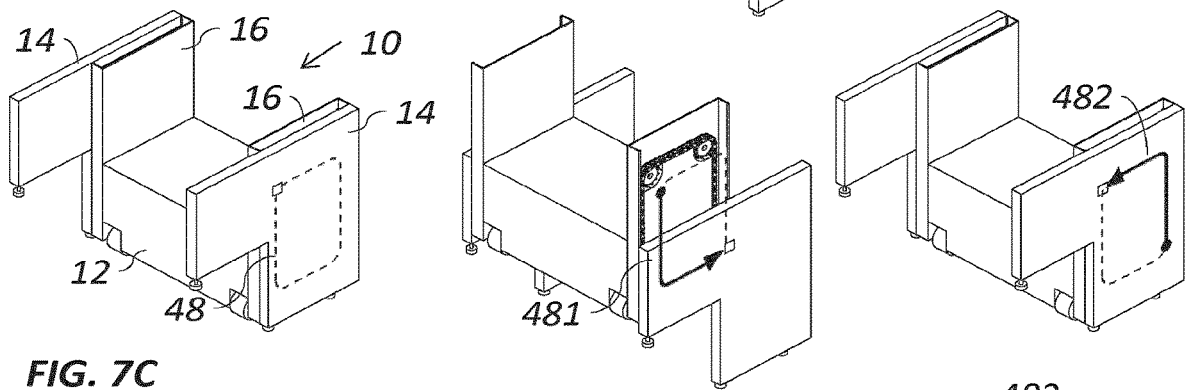
Figure 7D:
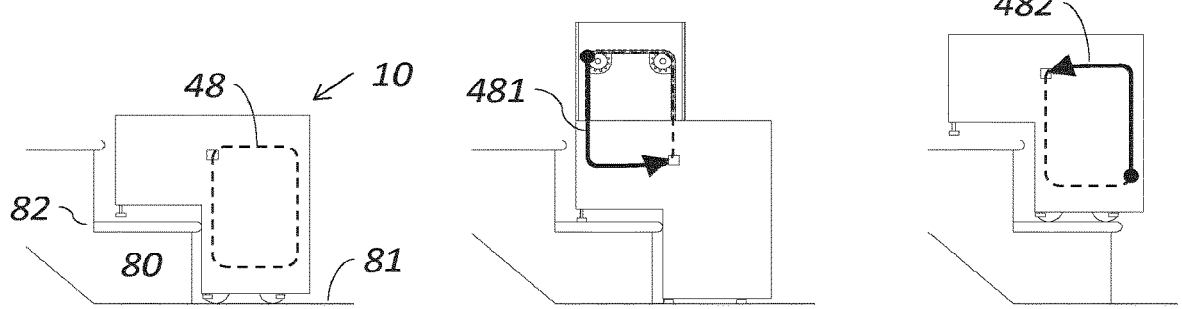

FIG. 7a shows a sequence of perspective views of the mechanism from FIG. 6 that illustrates the mechanism executing two segments of a cyclical motion path;

FIG. 7b shows a partially exploded view showing the mechanism from FIG. 7a attached to a payload body and a step frame;

FIG. 7c shows a sequence of perspective views of the step frame attached to the mechanism undergoing two segments of a cyclical motion path;

FIG. 7d depicts side views of the star traversing device climbing a step by using the cyclical motion shown in FIGS. 7a and 7c;

FIGS. 8a-8j show a side view of the embodiment of the stair traversing device shown in FIG. 1 traversing a step by illustrating successive positions of the payload body and the step frame during its cyclical climbing motion;

FIGS. 9a-9e show a side view of the embodiment of the stair traversing device shown in FIG. 1 illustrating the shifting of center of gravity of the stair traversing device during the cyclical climbing motion;

Mechanism Embodiments

Figure 10A:
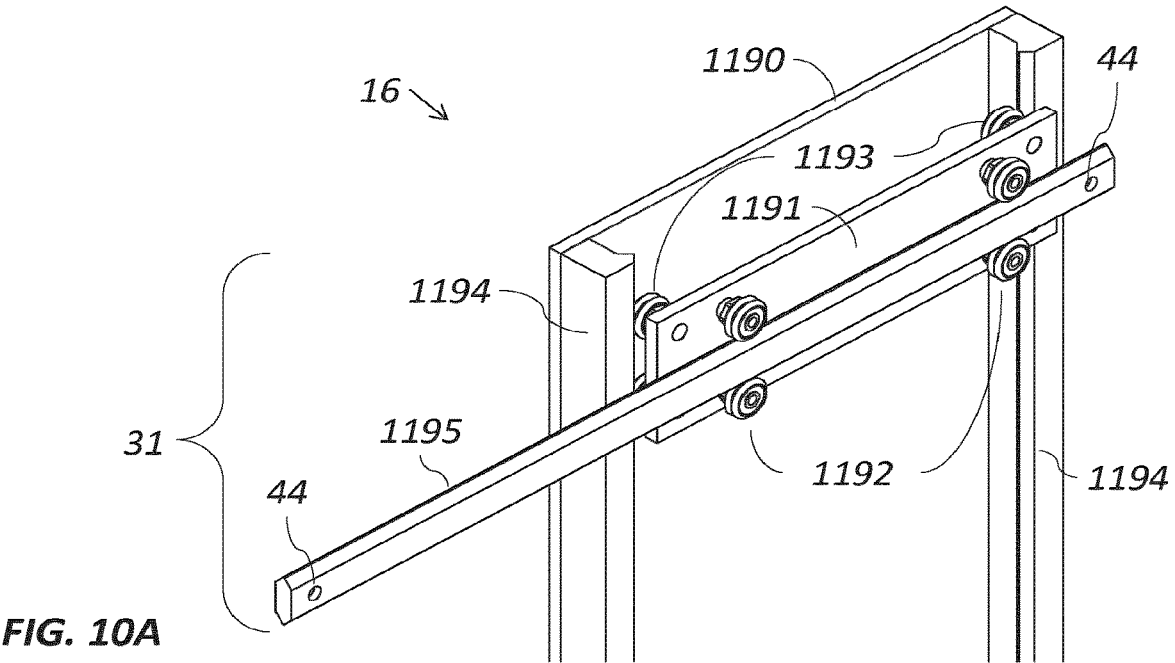
Figure 10B:
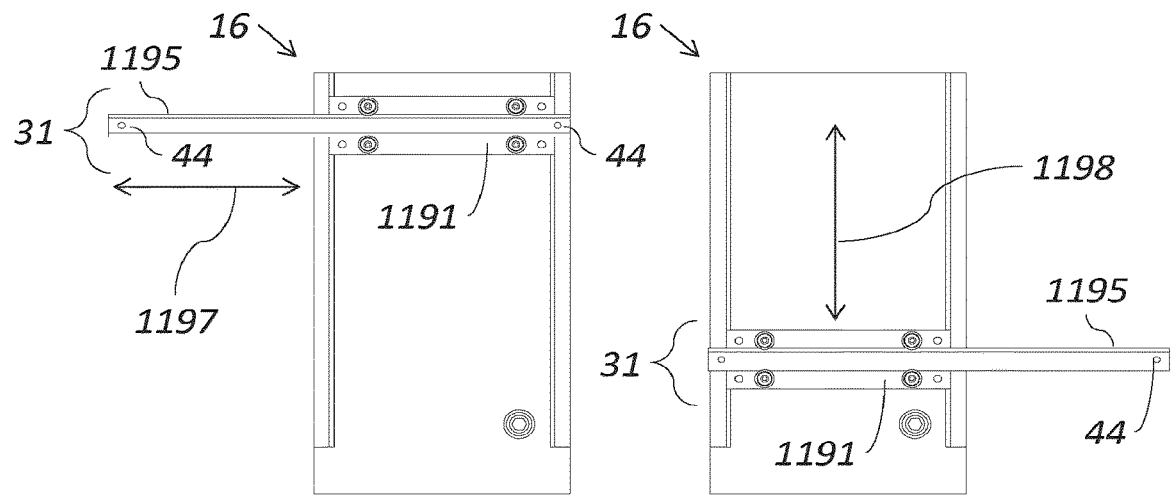
Figure 11A:
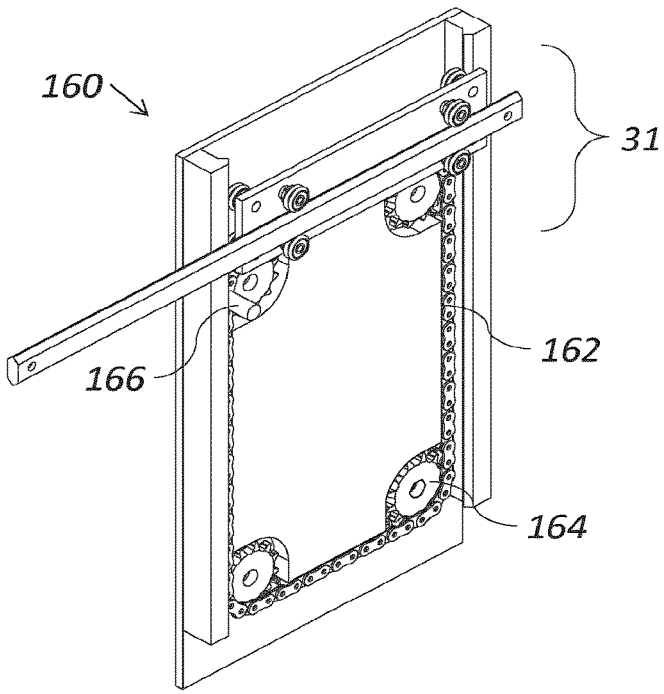
Figure 11B:
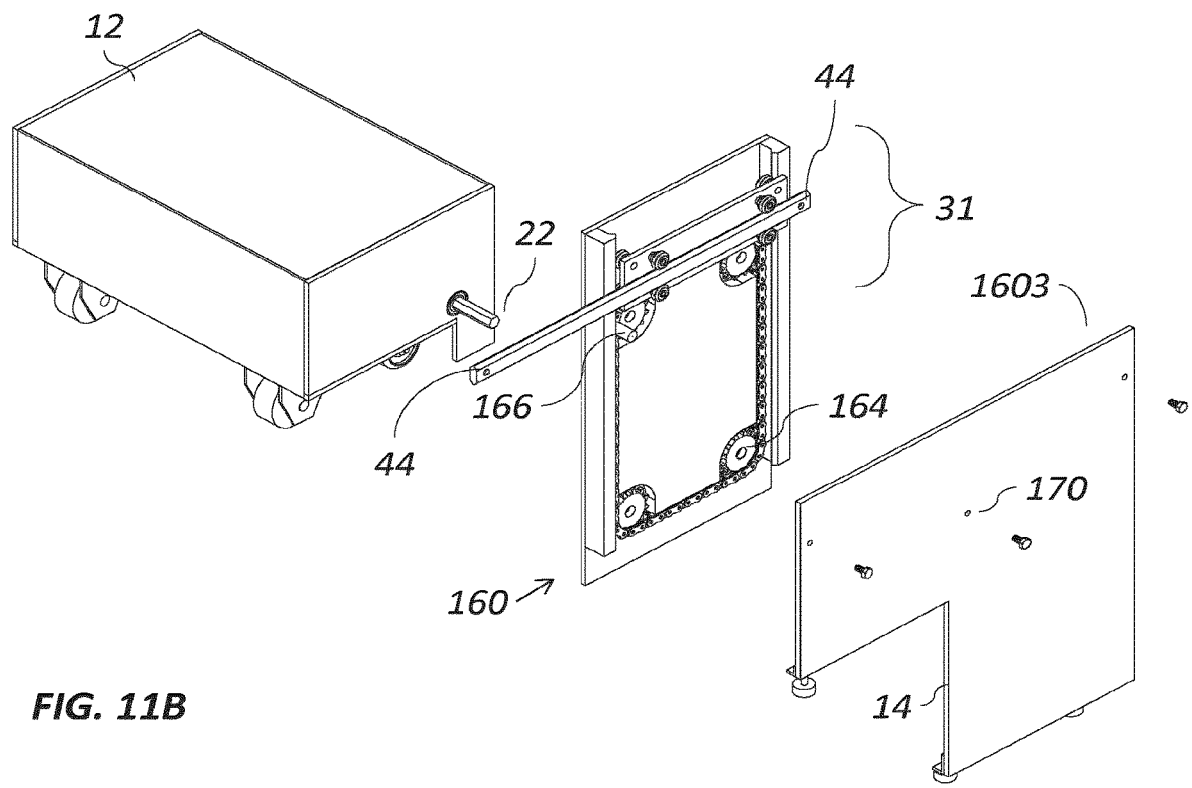
Figure 12A:
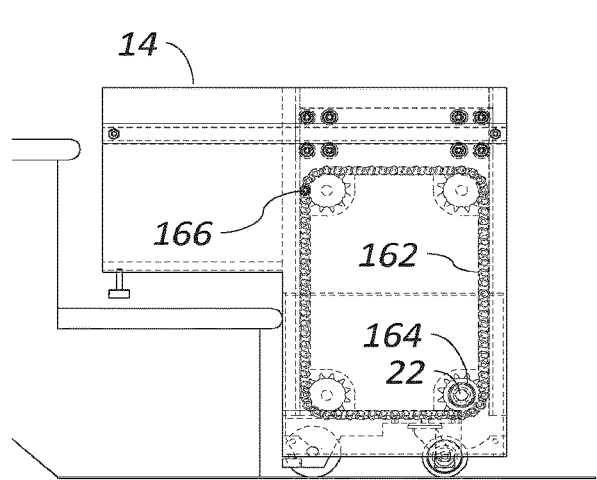
Figure 12B:
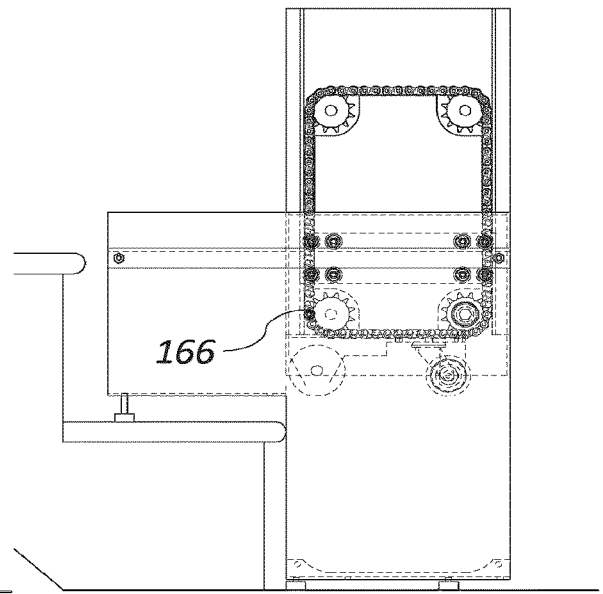
Figure 12C:
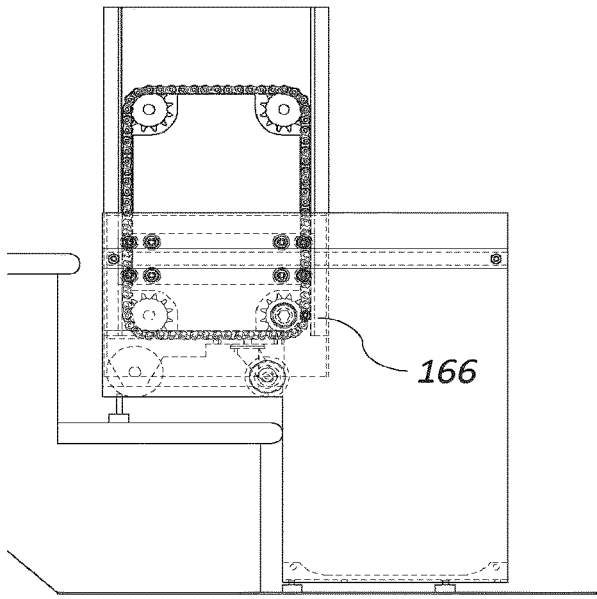
Figure 12D:
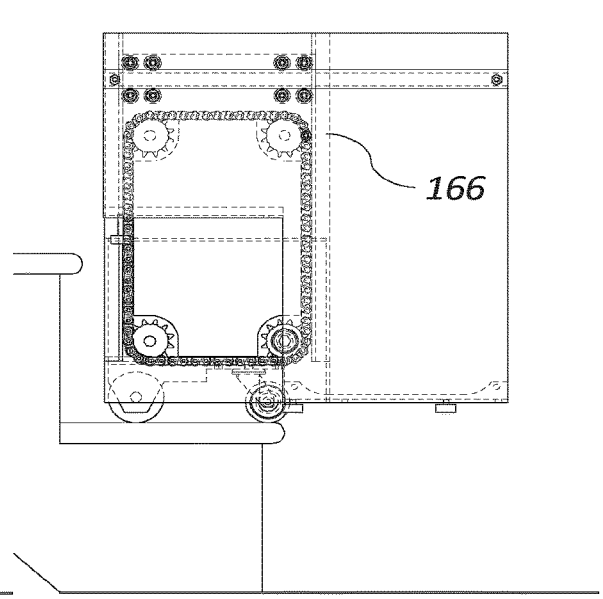
Figure 13:
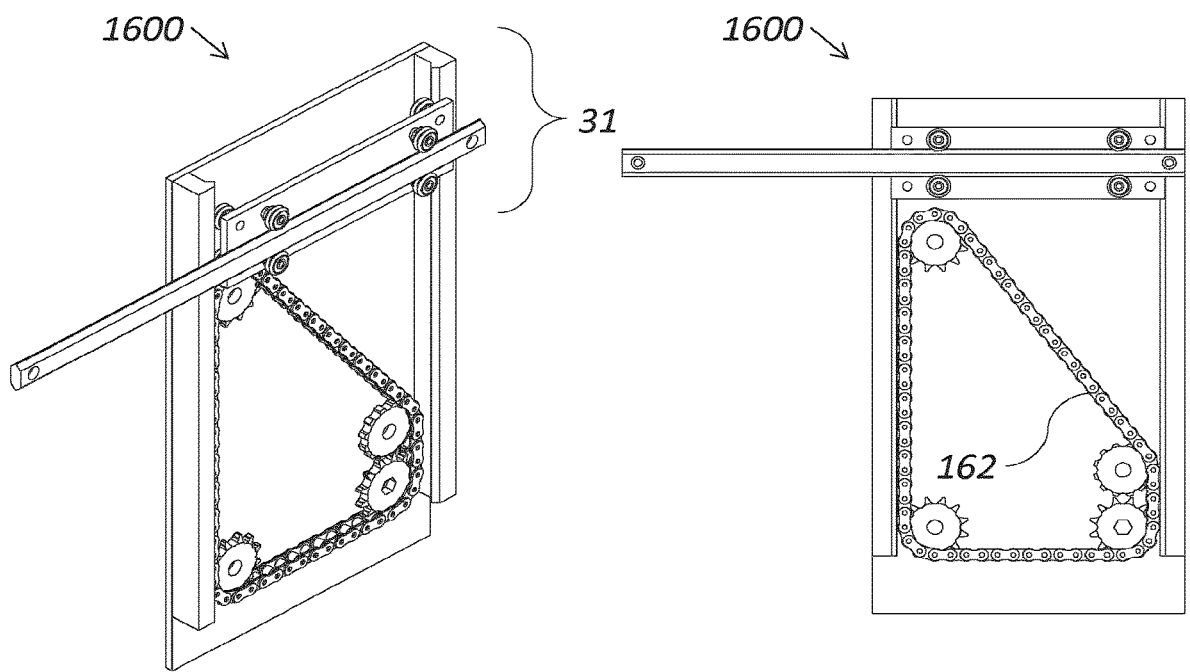

FIG. 10a depicts a perspective view of a preferred embodiment of the non-rotating connection as a non-rotating carriage assembly;

FIG. 10b shows a side view of the non-rotating carriage assembly from FIG. 10a as it moves through vertical and horizontal motions;

FIG. 11a shows a perspective view a preferred embodiment of the mechanism using a chain loop and four sprockets;

FIG. 11b shows an exploded view of the mechanism from FIG. 11a relative to the payload body and the step frame;

FIGS. 12a-12d show a partially transparent side view of the stair traversing device with the mechanism as shown in FIG. 11, illustrating the cyclical path motion resulting achieved using this mechanism;

FIG. 13 shows a perspective and side views of another embodiment of a mechanism using a chain and four sprockets that will produce a trapezoidal cyclical motion path.

Figure 14A:
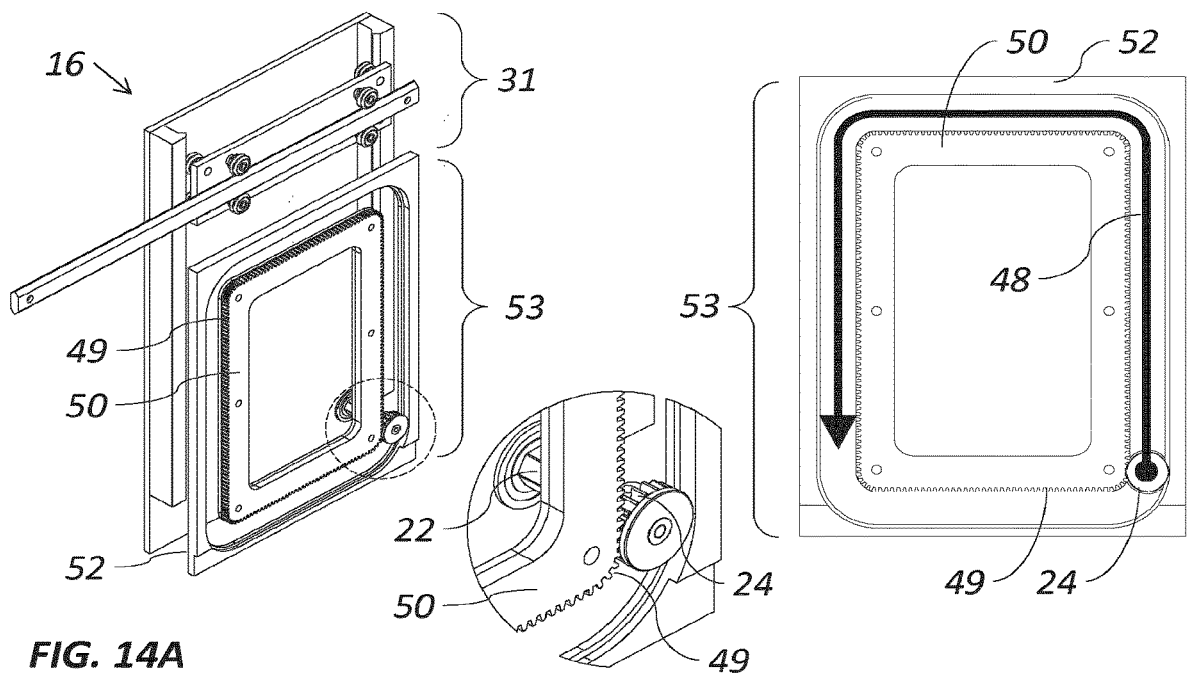
Figure 14B:
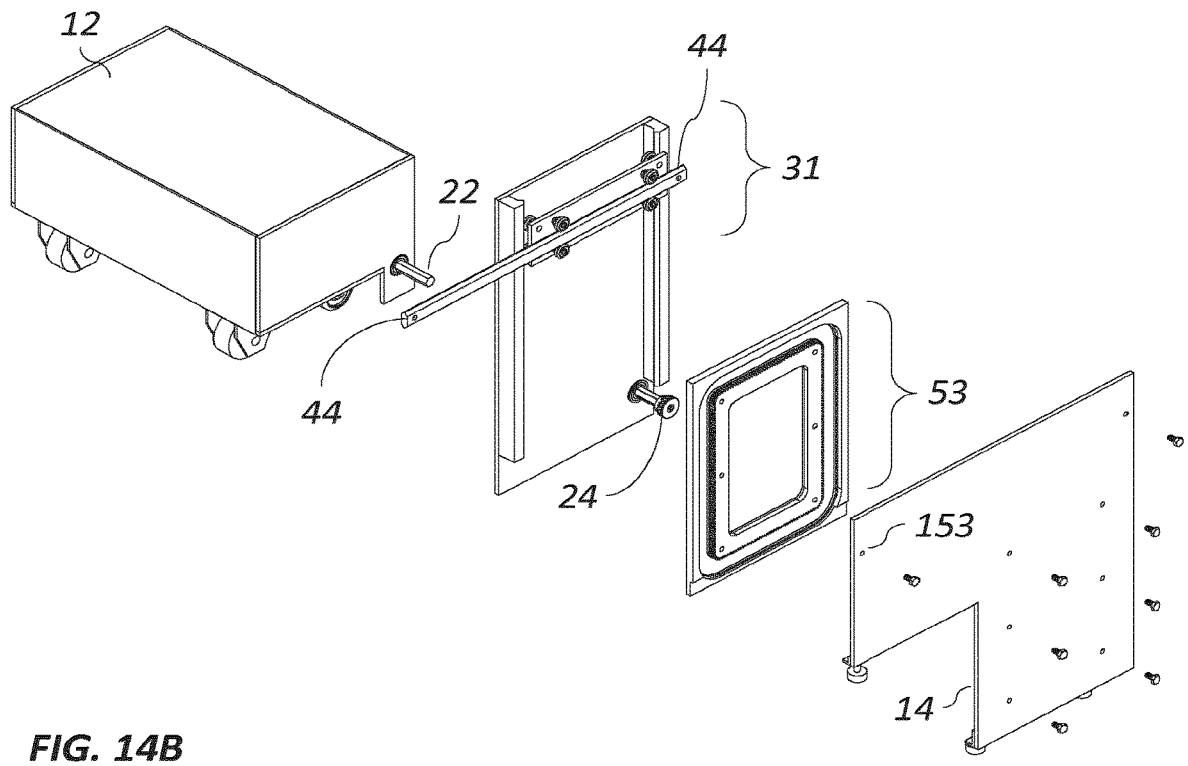
Figure 15A:
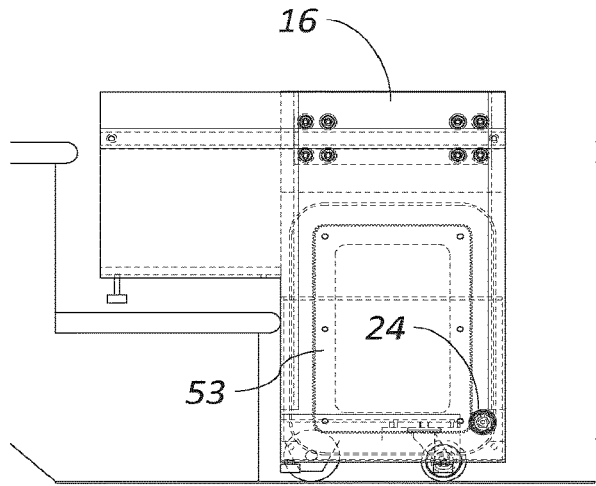
Figure 15B:
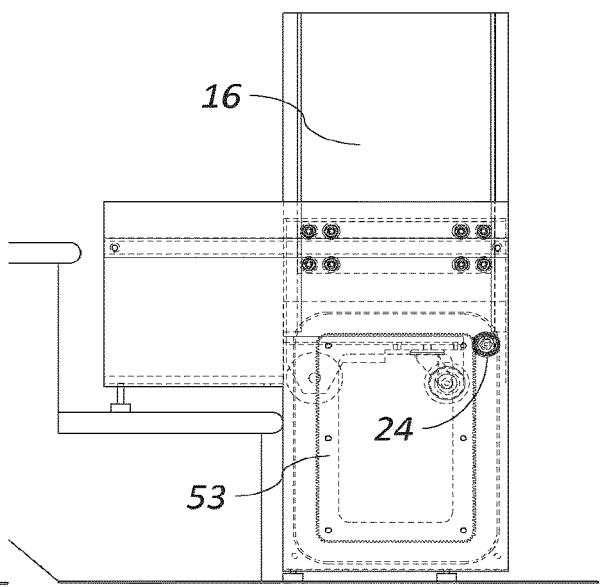
Figure 15C:
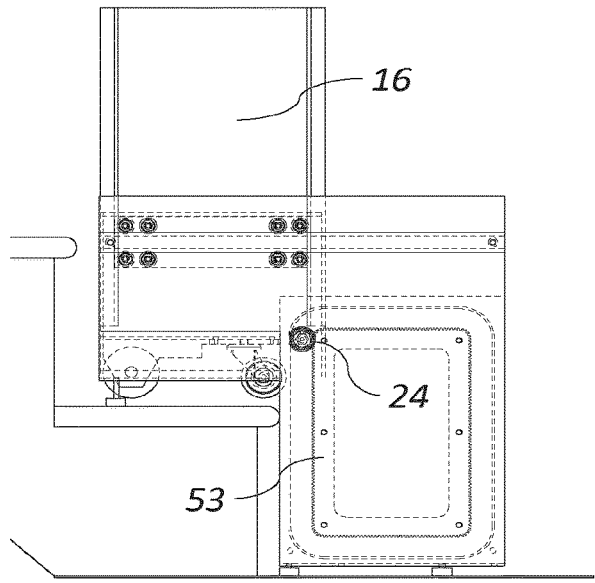
Figure 15D:
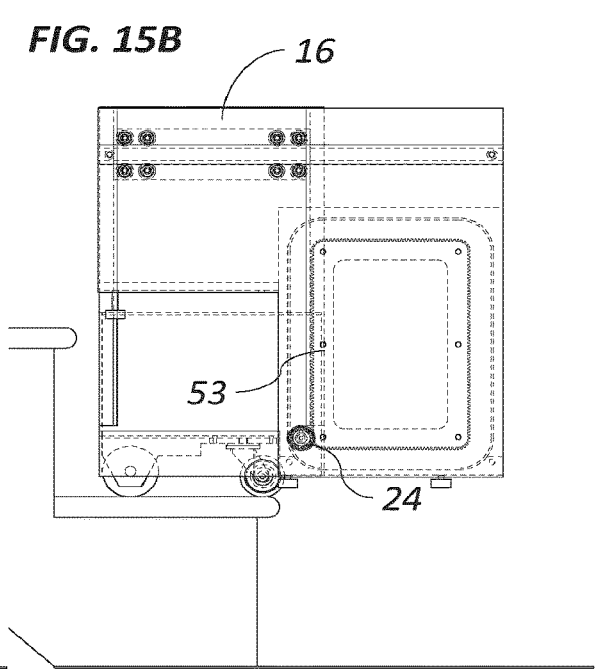
Figure 16:
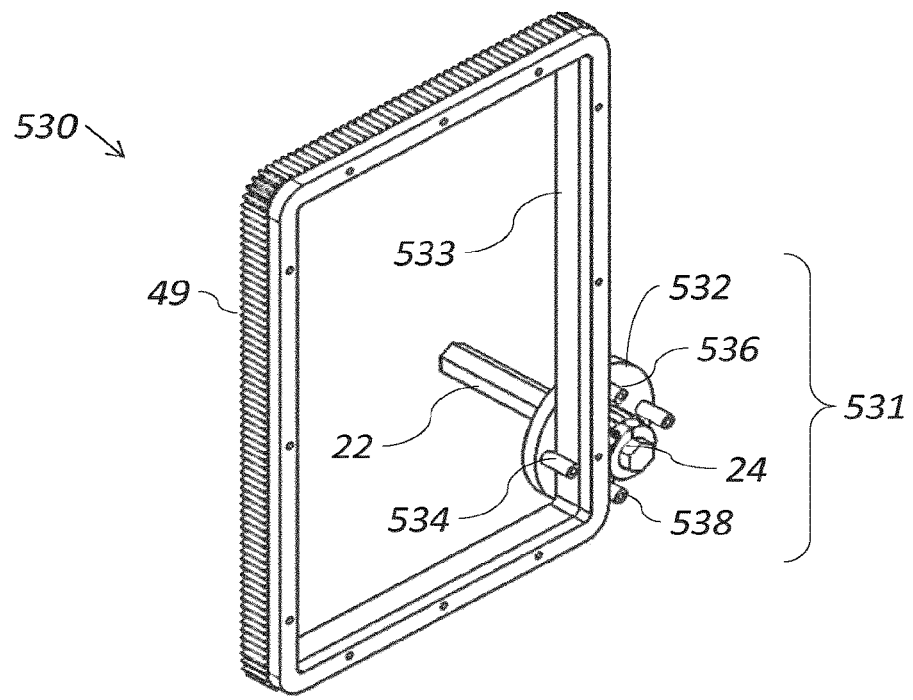
Figure 17:
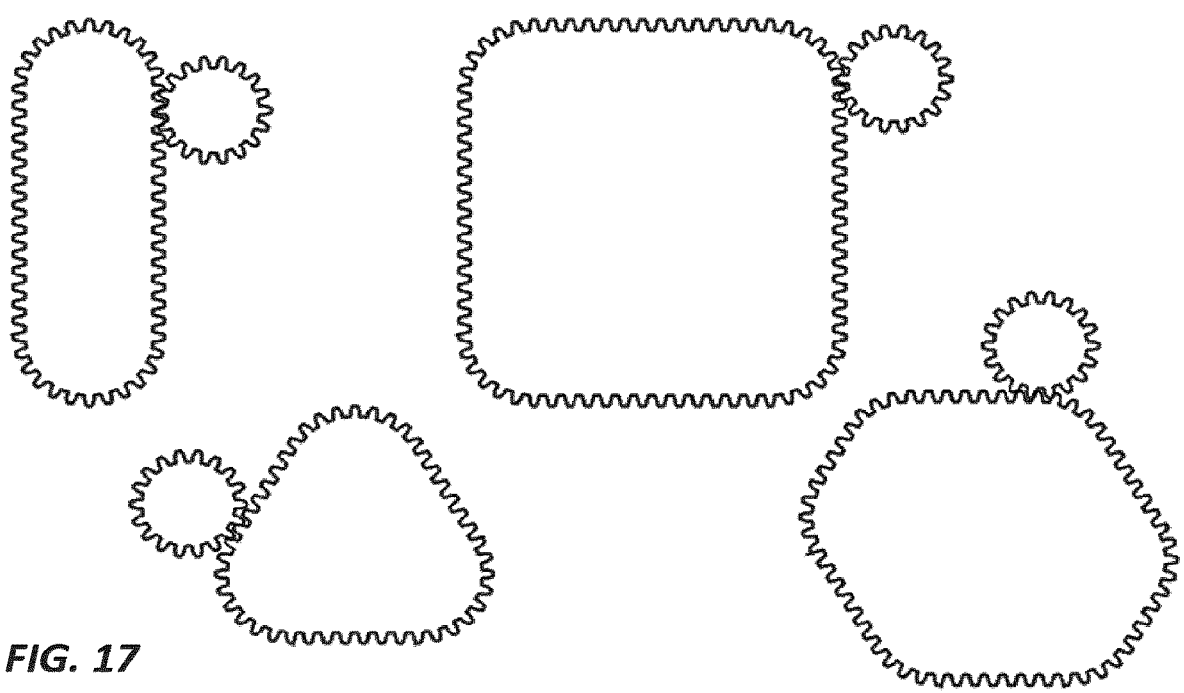
Figure 18A:
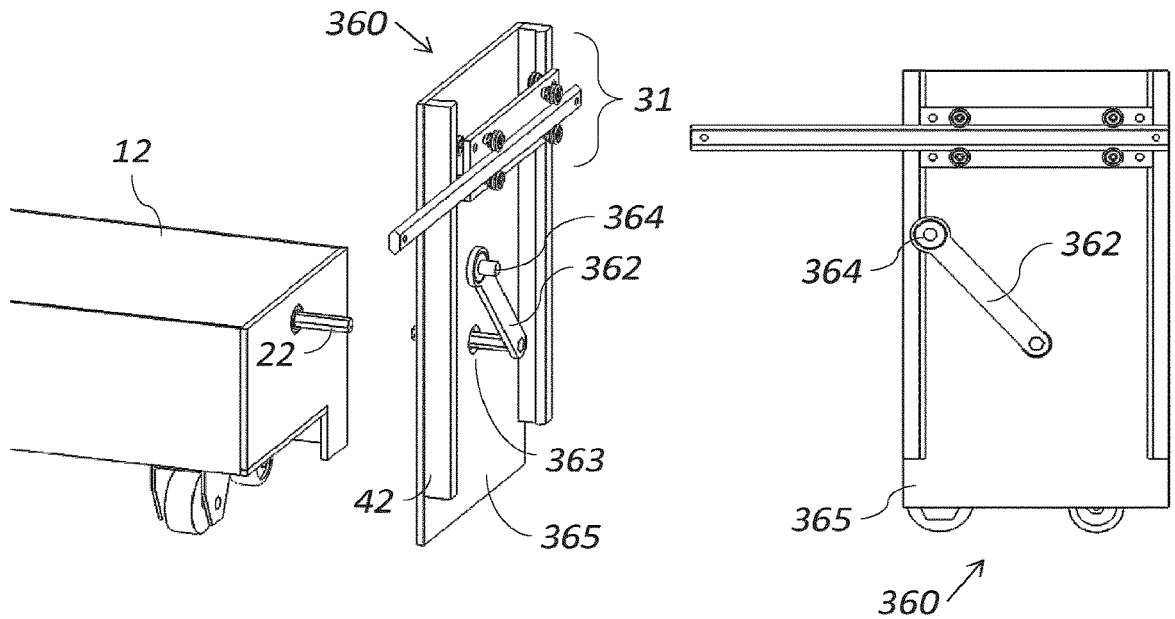
Figure 18B:
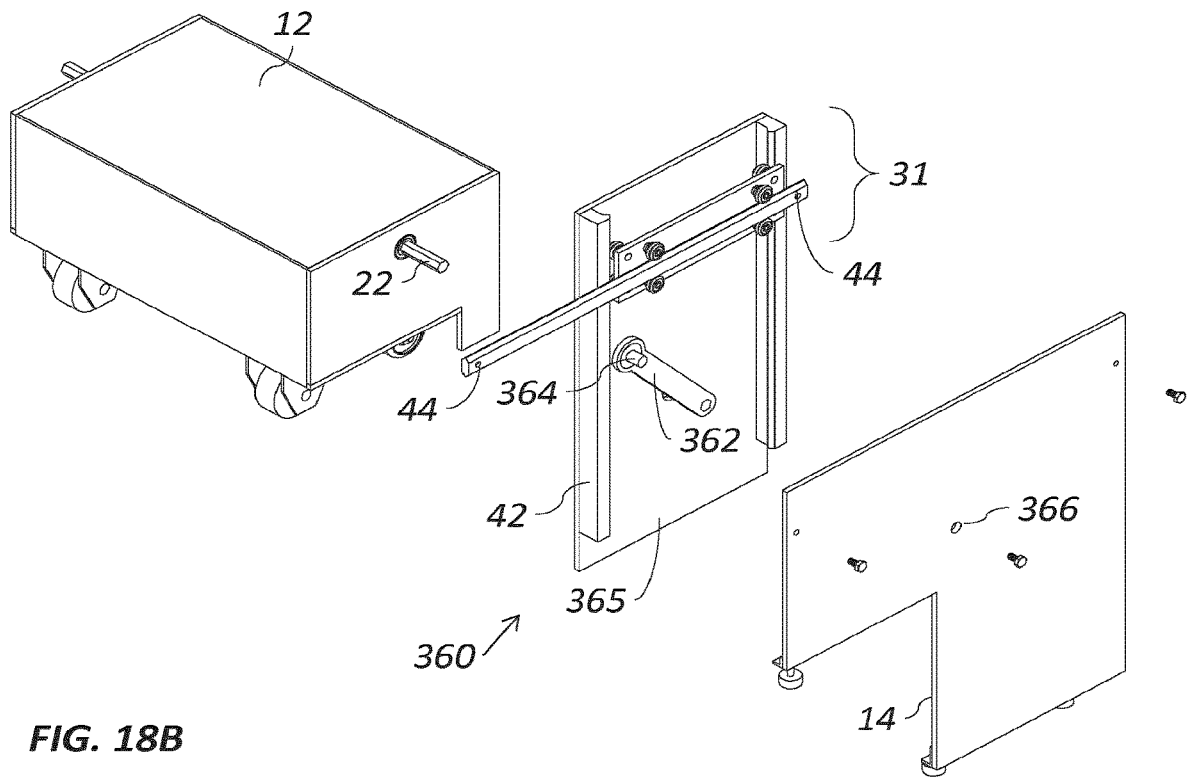
Figure 19A:
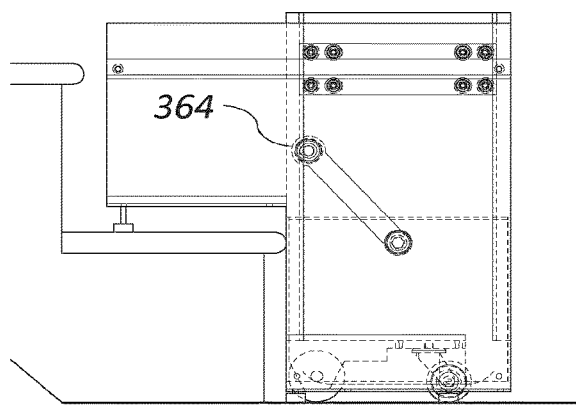
Figure 19B:
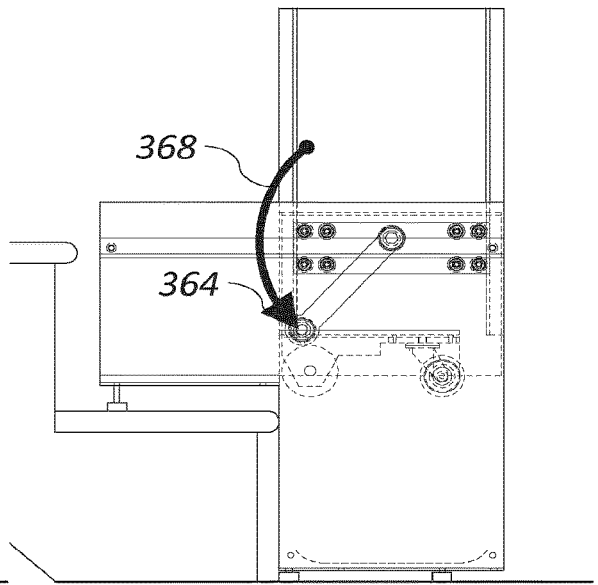
Figure 19C:
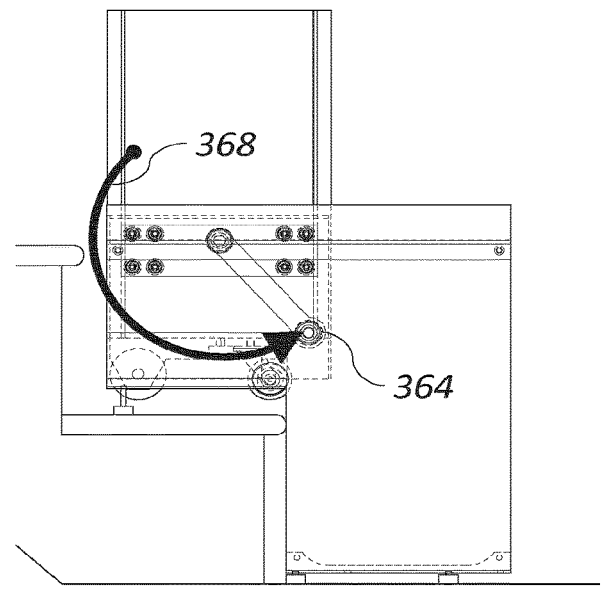
Figure 19D:
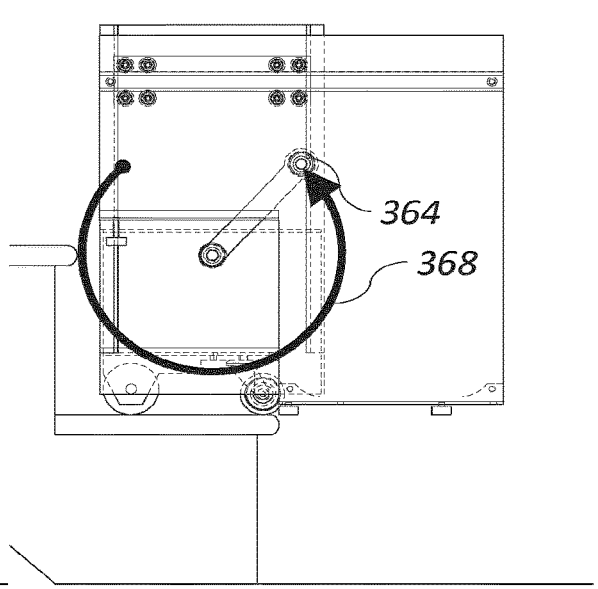
Figure 20A:
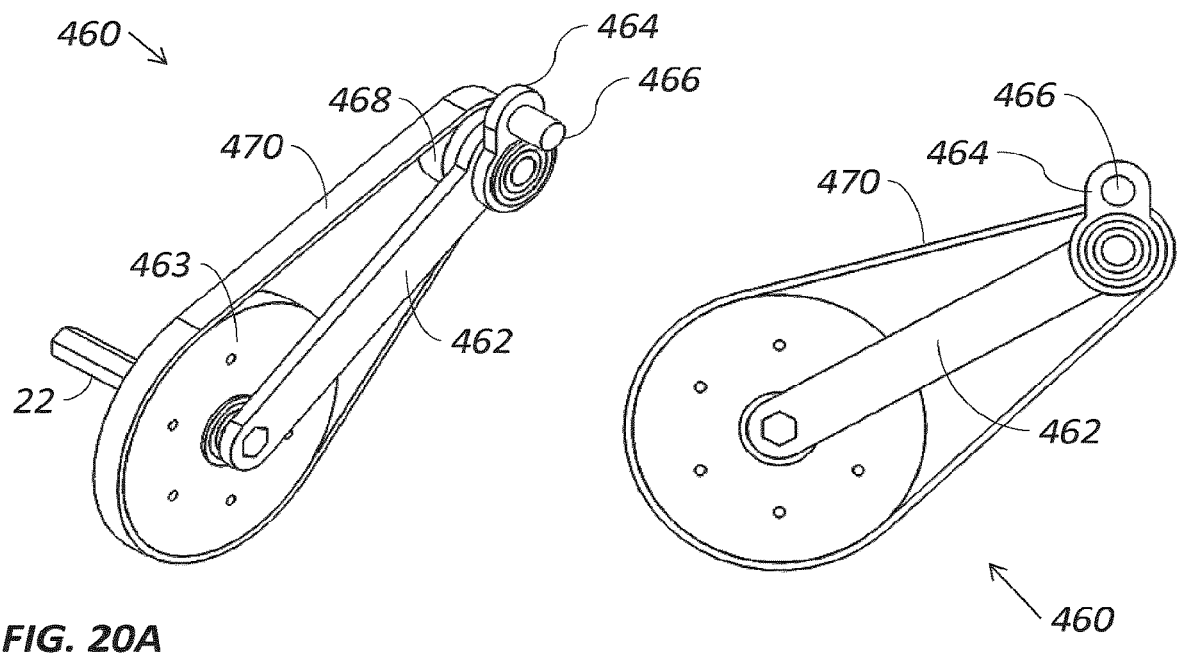
Figure 20B:
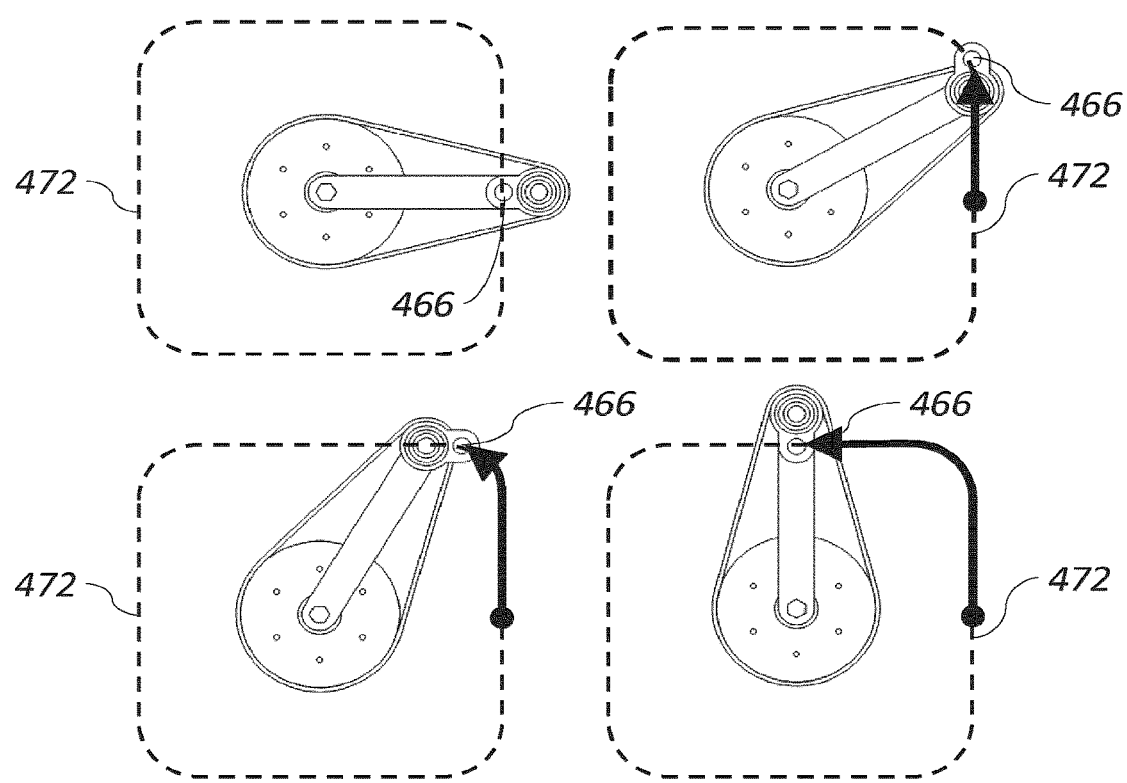
Figure 21A:
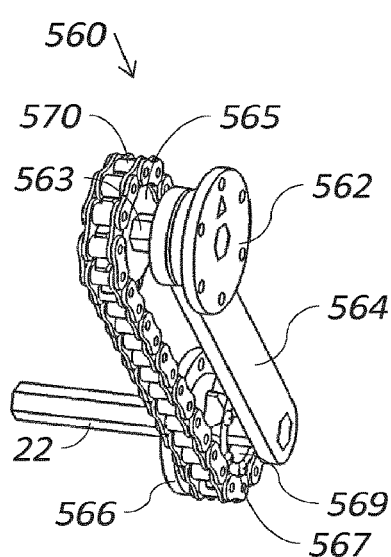
Figure 21B:
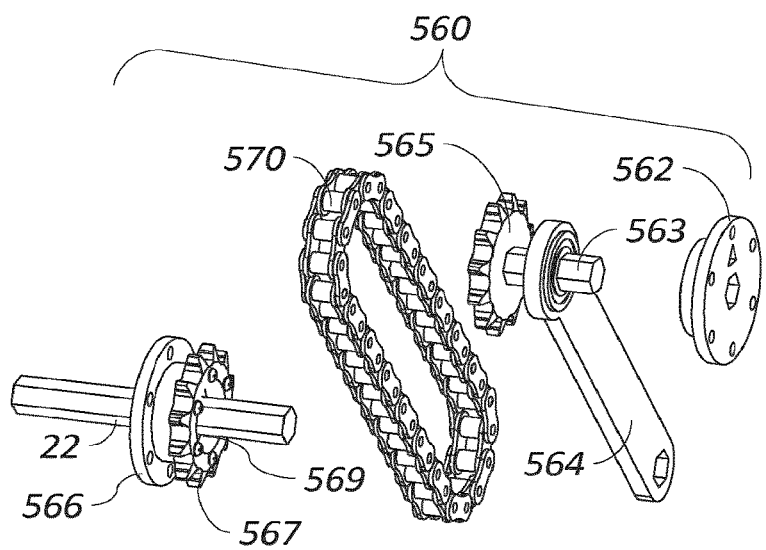

FIG. 14a shows a perspective and side views of a preferred embodiment of a looped rack-and-pinion mechanism, as well as a detailed view of the pinion engaging the looped rack;

FIG. 14b shows an exploded view of the mechanism from FIG. 14a in relation to the payload body and the step frame;

FIGS. 15a-15d show a partially transparent side view of a stair traversing device incorporating the looped rack-and-pinion mechanism shown in FIG. 14 as it climbs stairs using its cyclical motion;

FIG. 16 shows an perspective view of an alternative embodiment of the looped rack-and-pinion mechanism with a constraint mechanism using pins;

FIG. 17 shows a side view of other possible configurations of the loop rack as shown in FIG. 14 and FIG. 16;

FIG. 18a shows a perspective view and a side view of another embodiment of the mechanism using a crank arm;

FIG. 18b shows an exploded view shows the crank arm mechanism from FIG. 18a relative to the payload body and a step frame;

FIGS. 19a-19d show a partially transparent side view of the stair traversing device with mechanism as shown in FIG. 18 illustrating the cyclical climbing motion achieved through the mechanism;

FIG. 20a shows a perspective and a side view of a double crank arm cyclical path mechanism;

FIG. 20b shows a side view of the hypotrochoid cyclical path achieved by the double crank arm cyclical path mechanism shown in FIG. 20a;

FIG. 21a shows a perspective view of a preferred embodiment of a combined mechanism based on a set of non-rotation hubs;

FIG. 21b shows an exploded perspective view of the mechanism from FIG. 21a.

Figure 21C:
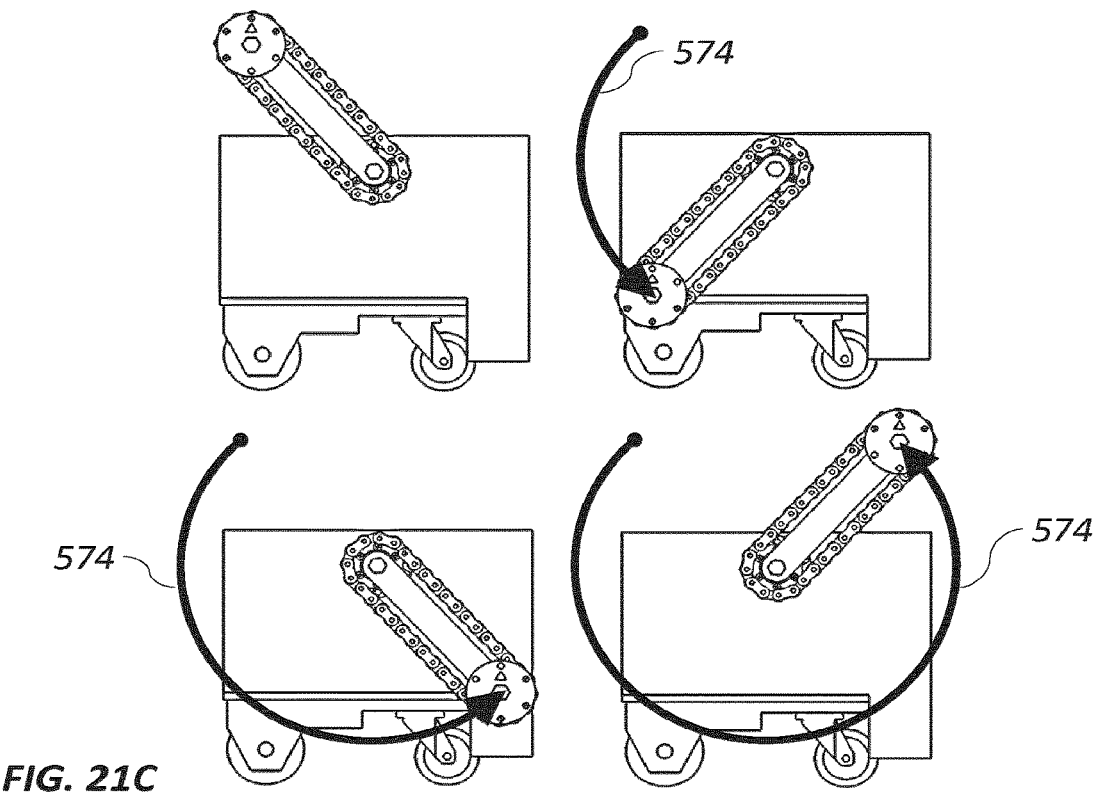
Figure 22A:
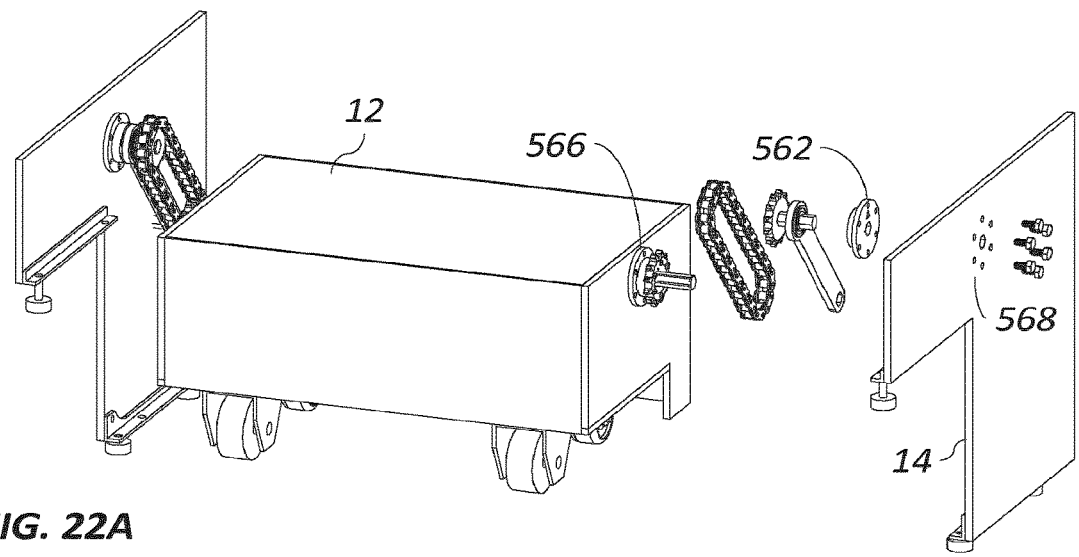

FIG. 21c shows a side view of a sequence of motions by the combined mechanism shown in FIG. 21a in execution of a circular cyclical motion;

FIG. 22a shows perspective views of the combined mechanism depicted in FIG. 21 in relation to the payload body and the step frame;

FIGS. 22b-22j show a side view of the cyclical motion executed by a stair traversing device using the mechanism as shown in FIG. 22a.

FIG. 23a shows a perspective view of one embodiment of the non-rotating hub mechanism using gears instead of a chain loop;

FIG. 23b shows an exploded perspective view of the mechanism from FIG. 23A.

Figure 23C:
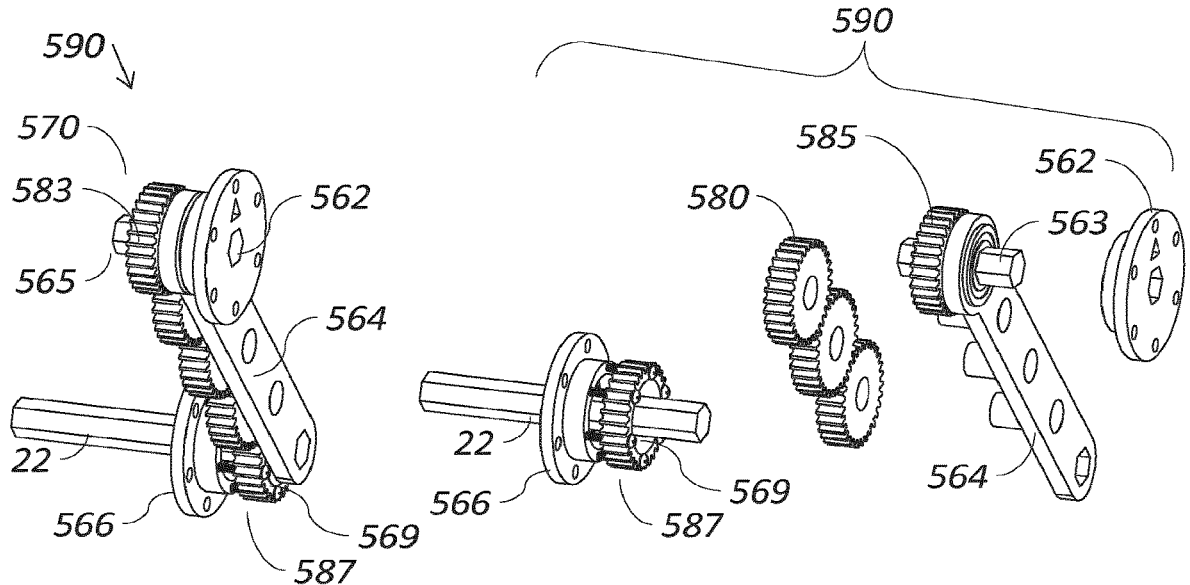
Figure 23C:
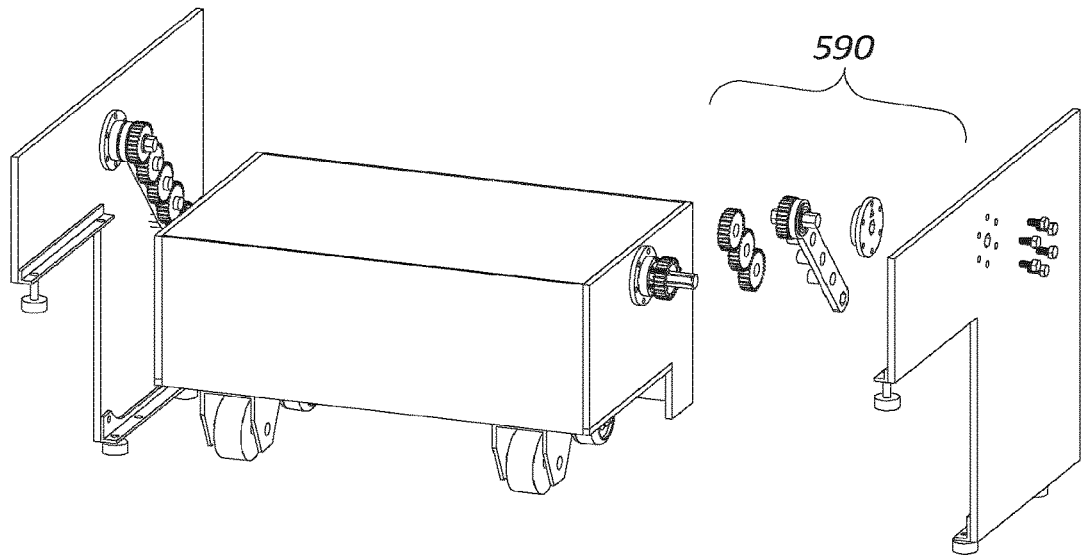
Figure 24:
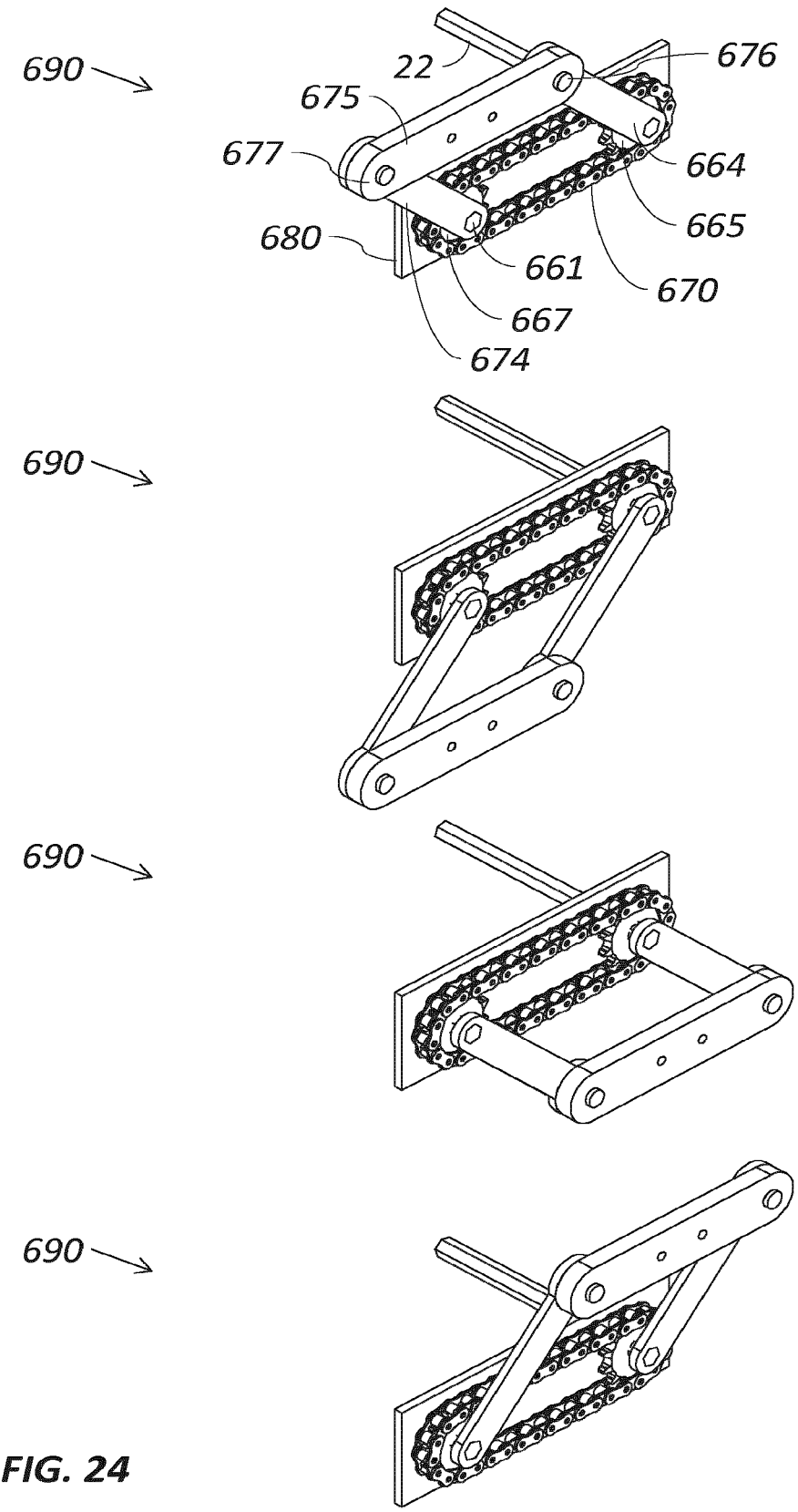
Figure 25:
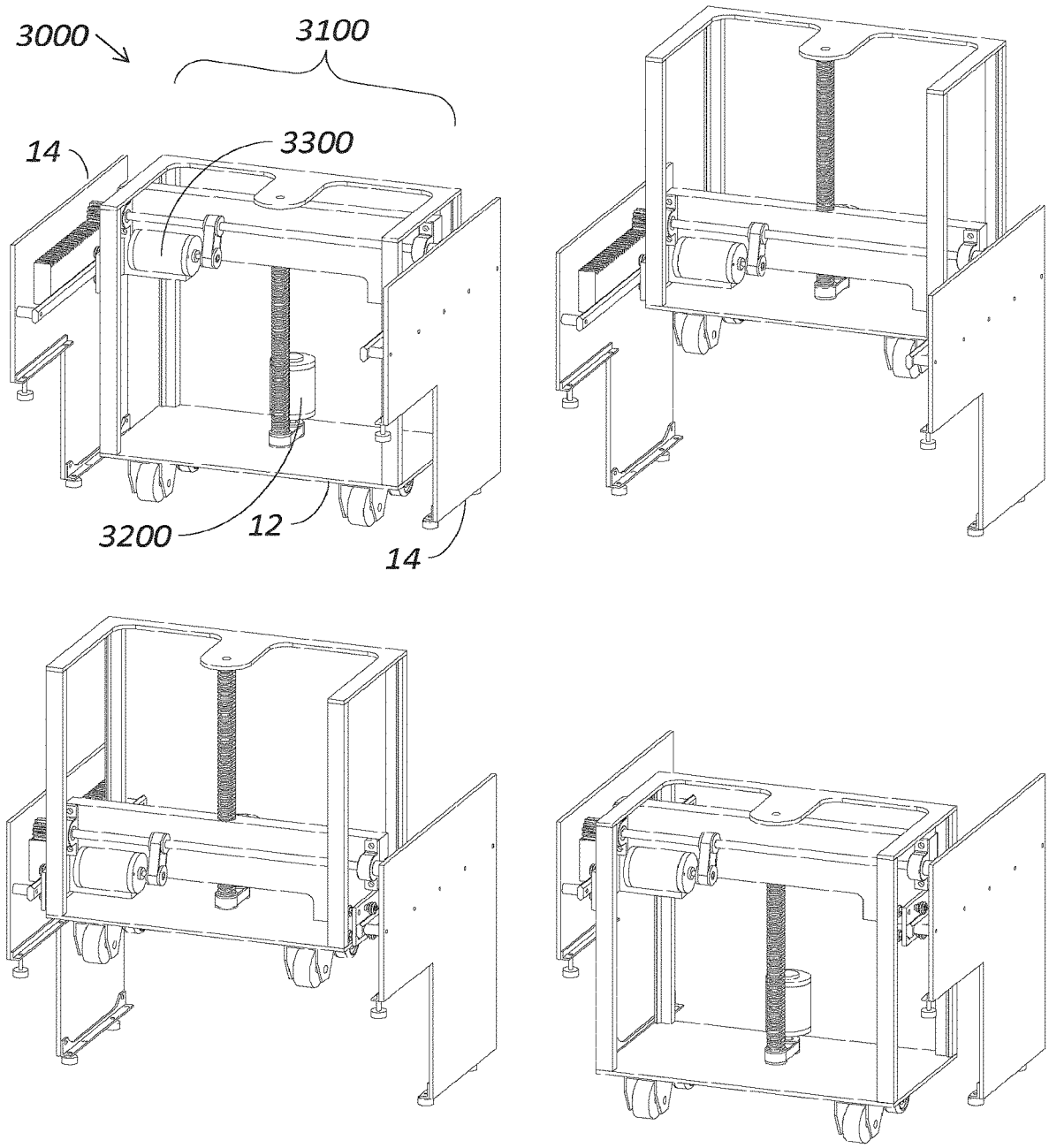

FIG. 23c shows a perspective view of the mechanism from FIG. 23A in relation to the payload body and the step frame;

FIG. 24 shows another embodiment of a mechanism that produces a circular motion path, which uses a four-bar linkage driven by a chain loop;

FIG. 25 shows perspective views of a preferred embodiment of the stair traversing device at four points in its cyclical motion, where the mechanism is divided into two separate stages, one vertical and one horizontal, each driven by its own actuator;

Step Frame Embodiments

Figure 26A:
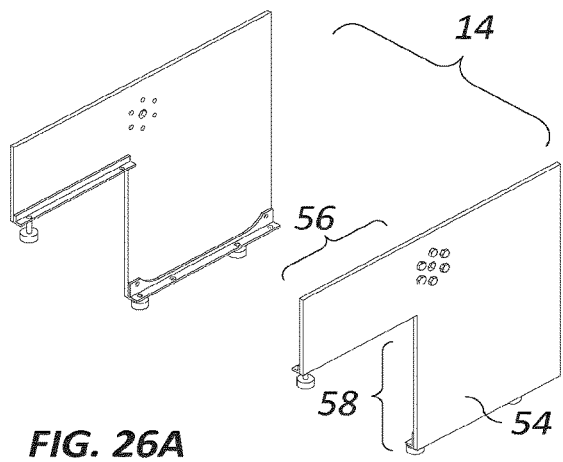
Figure 26B:
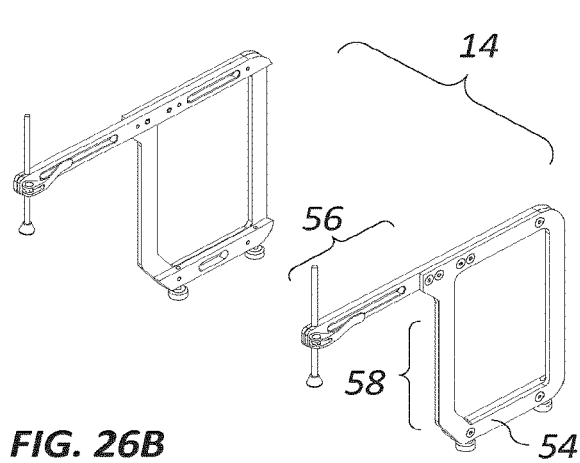
Figure 26C:
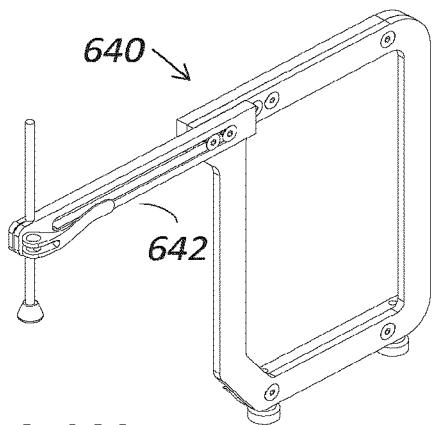
Figure 26D:
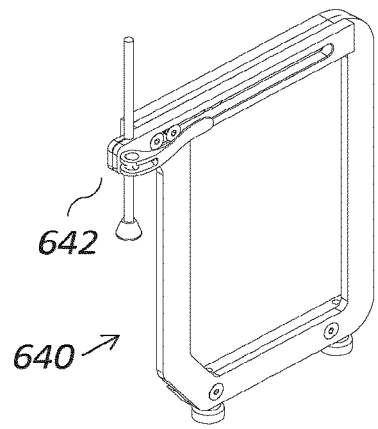
Figure 26D:
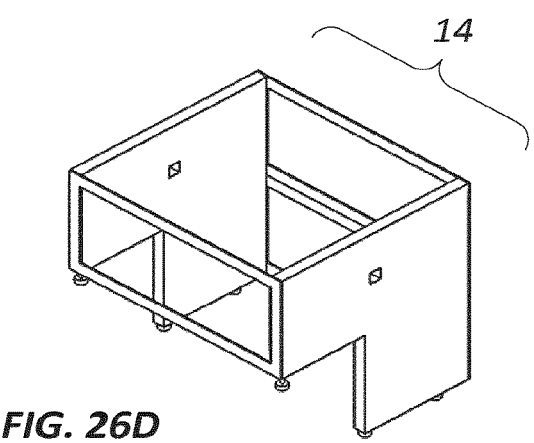
Figure 26E:
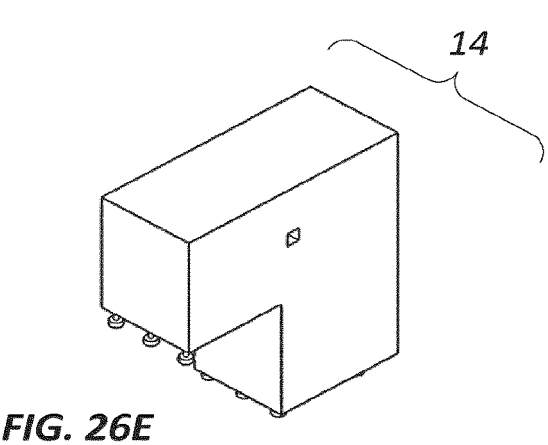
Figure 27A:
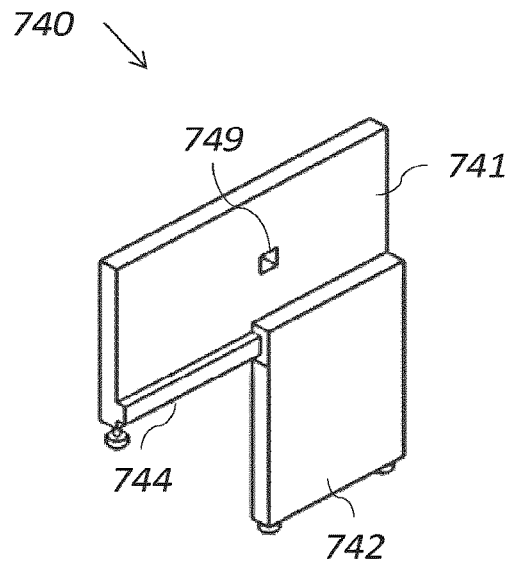
Figure 27B:
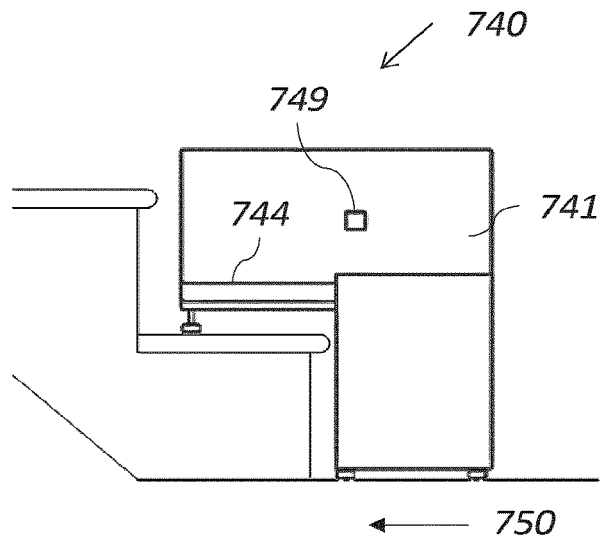
Figure 27C:
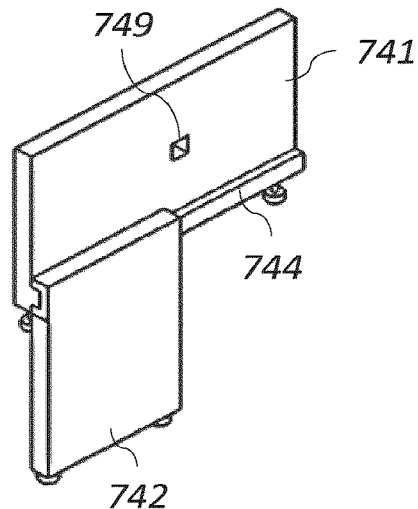
Figure 27D:
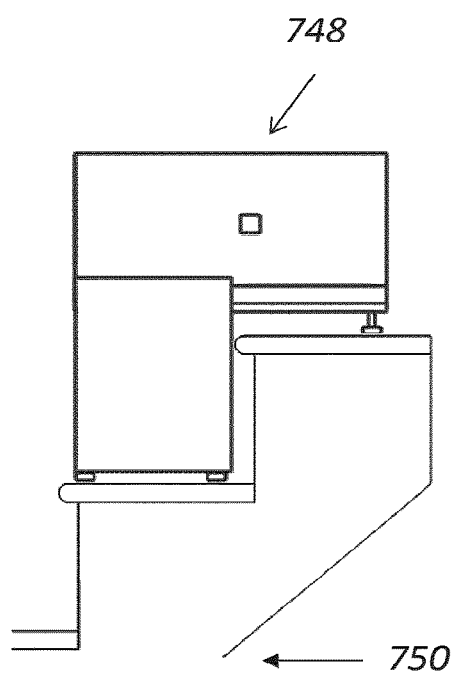
Figure 29A:
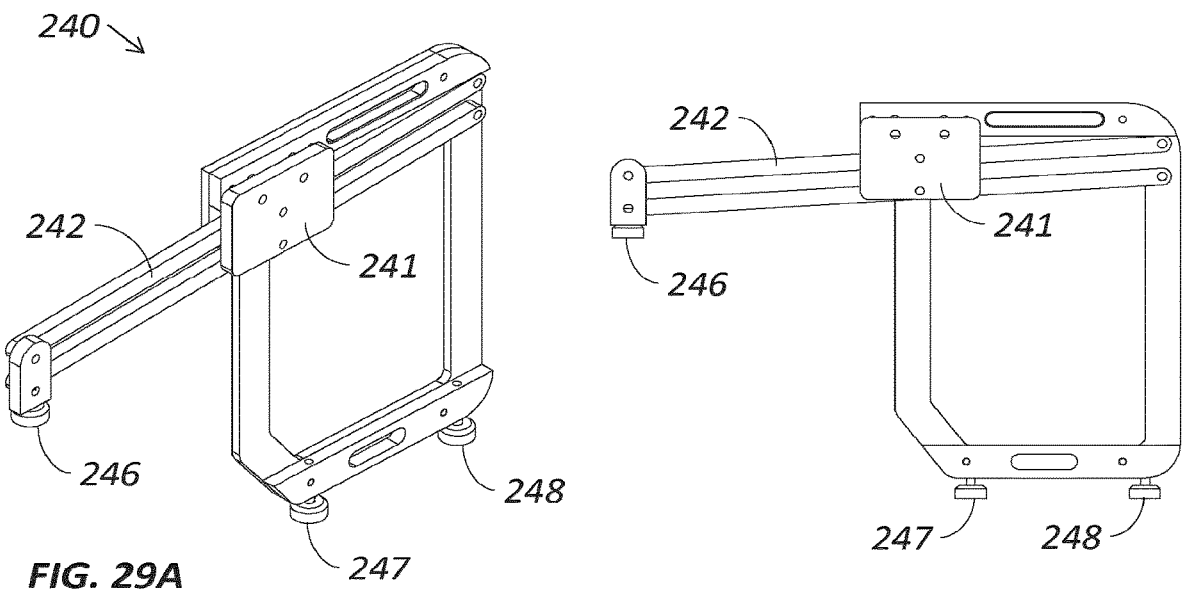
Figure 29B:
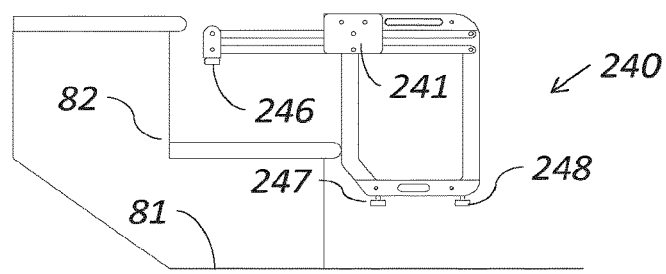
Figure 29B:
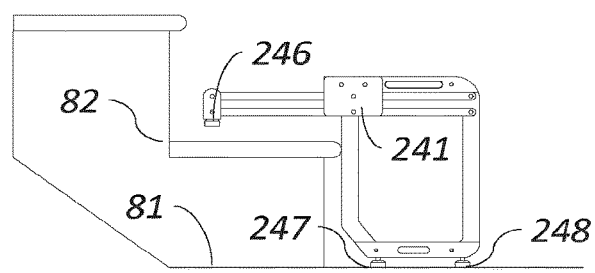
Figure 29B:
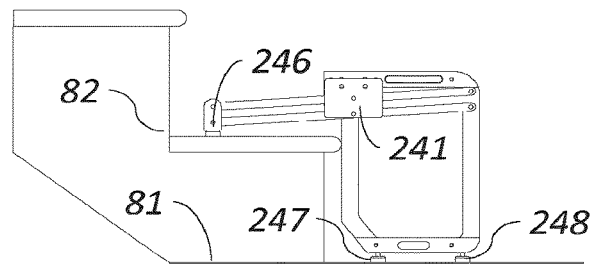
Figure 30A:
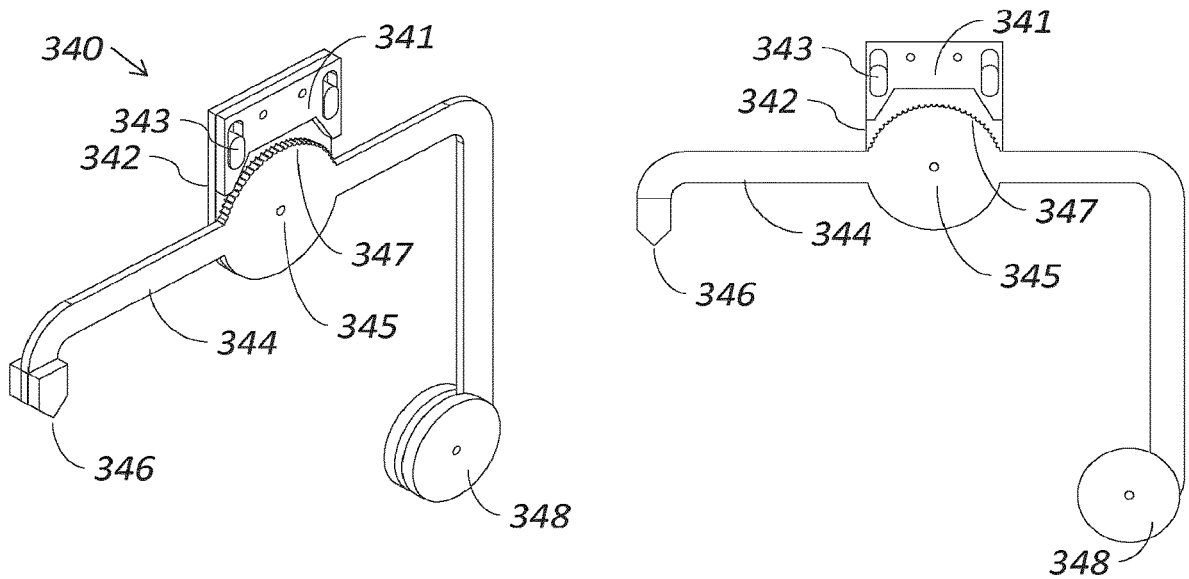
Figure 30B:
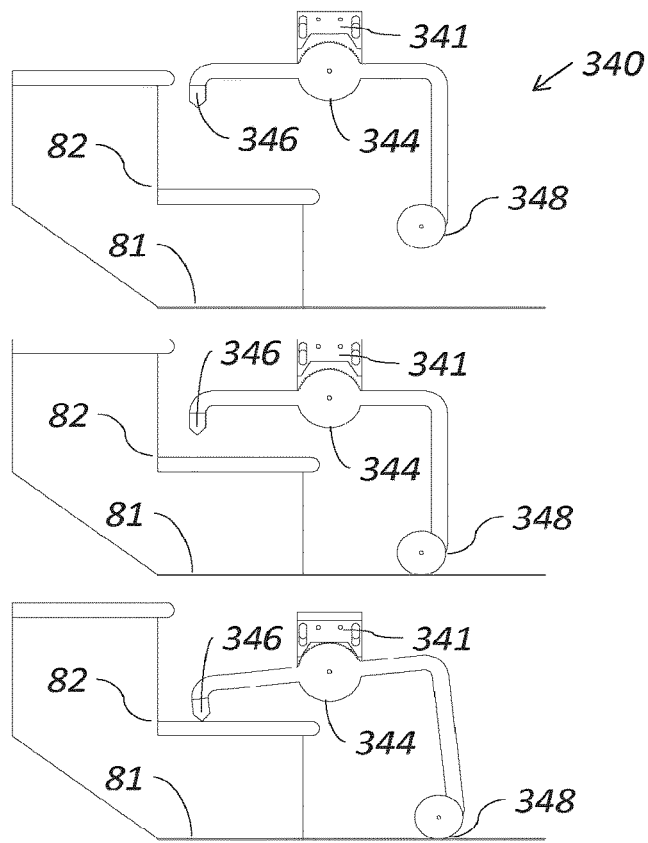
Figures 31A, 31B:
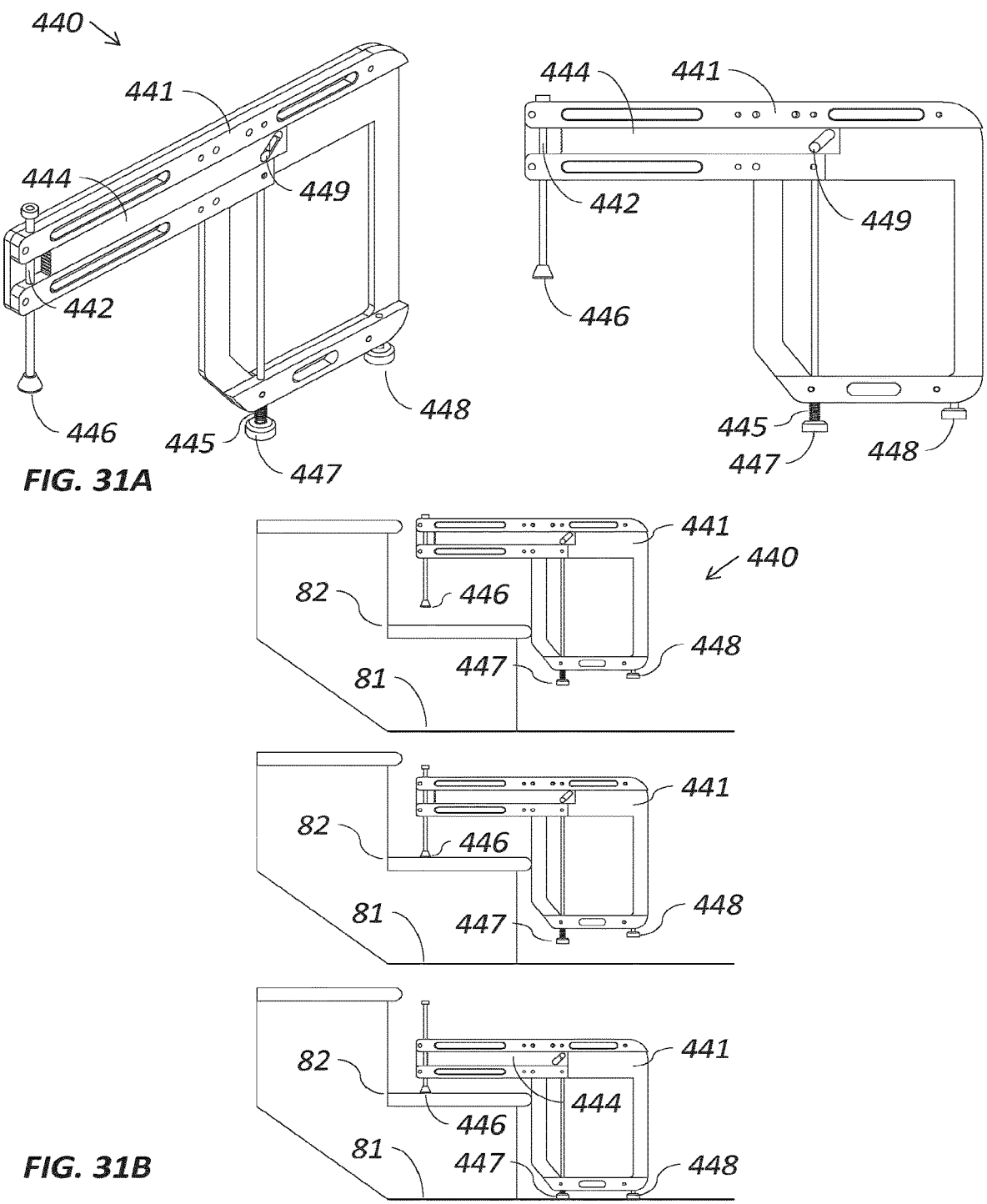
Figures 32A, 32B:
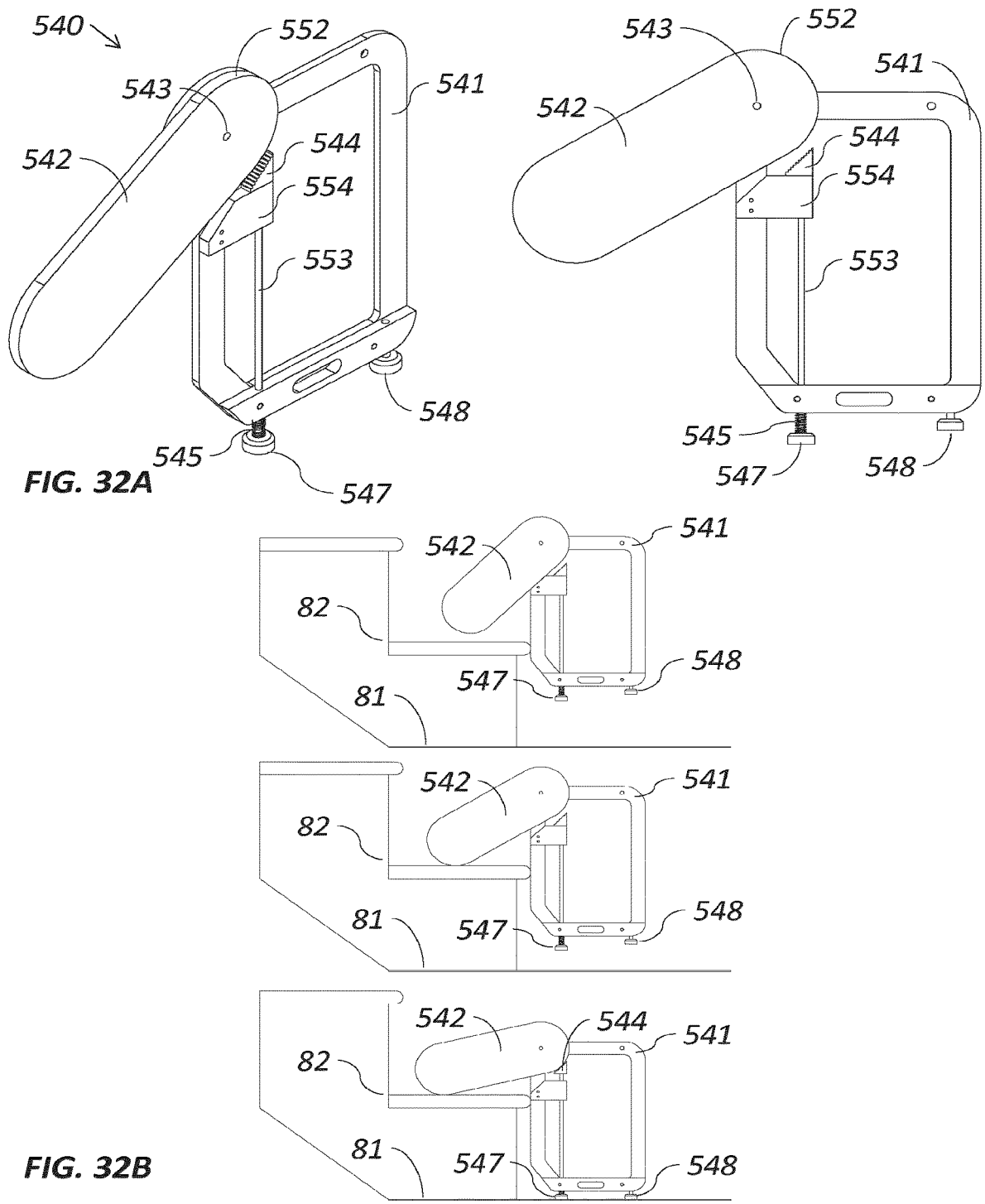
Figure 33A:
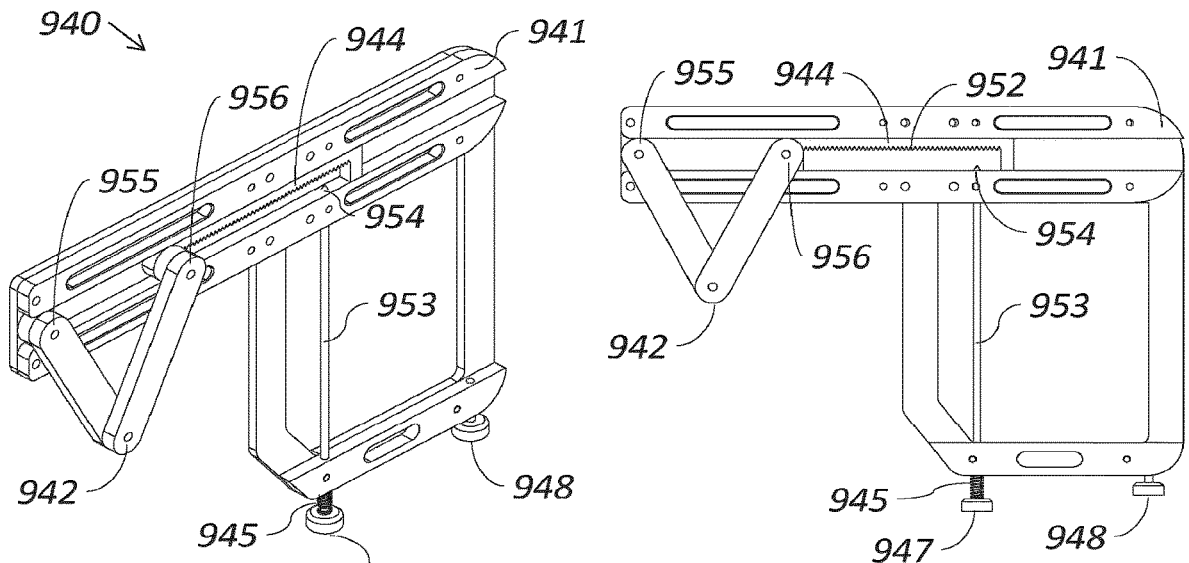
Figure 33B:
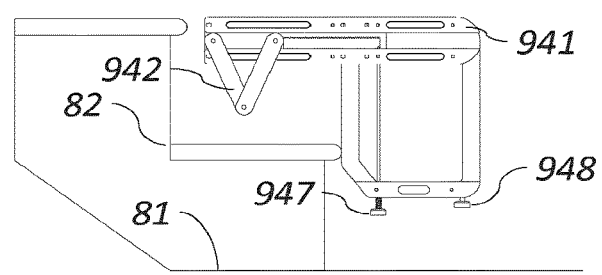
Figure 33B:
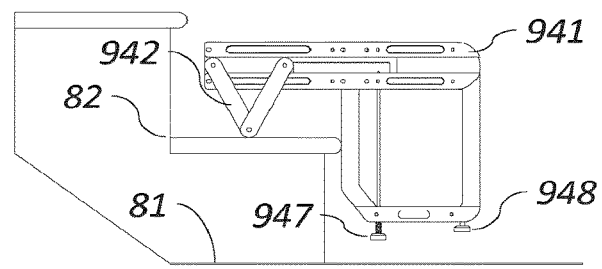
Figure 33B:
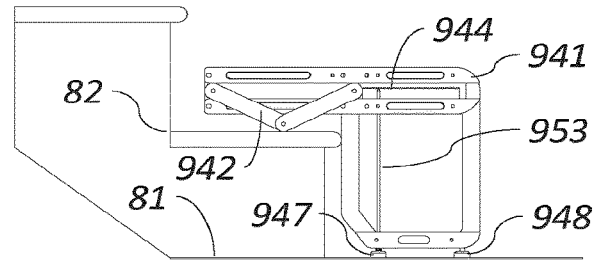
Figure 34A:
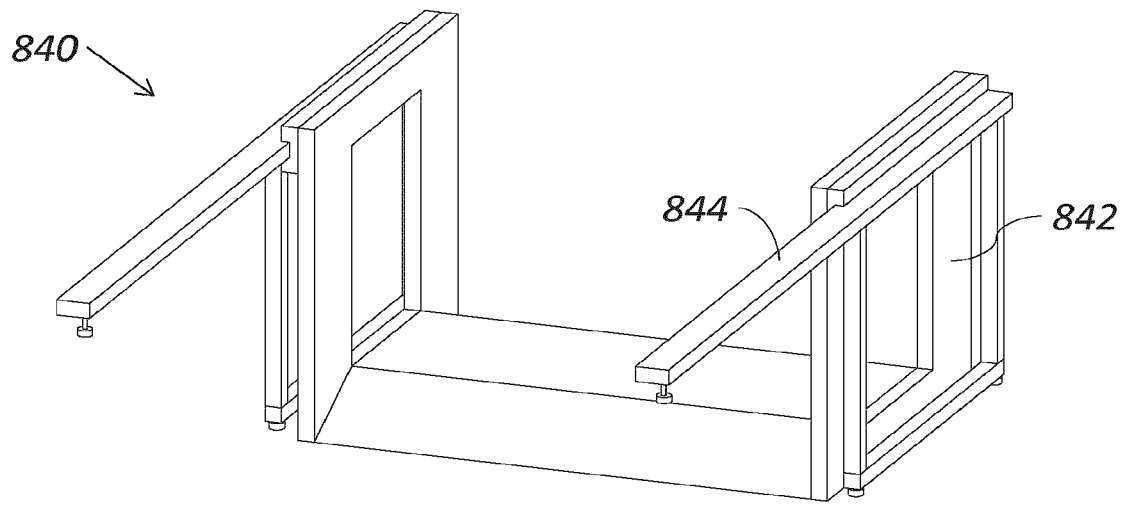
Figure 34B:
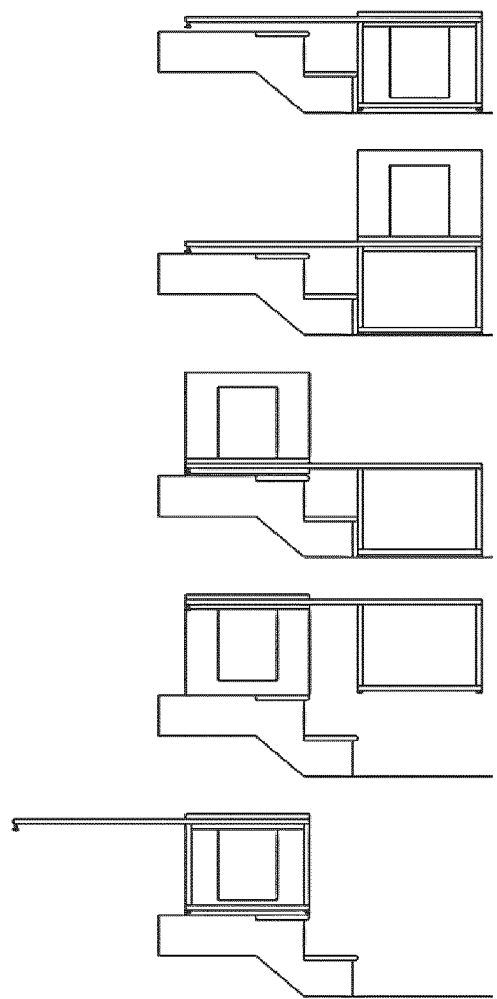

FIG. 26a shows a preferred embodiment of the step frame consisting of multiple fixed geometry bodies moving in unison;

FIG. 26b shows another preferred embodiment of a multi-body step frame with a fixed geometry consisting of lightweight frames;

FIG. 26c shows an embodiment of one step frame body from FIG. 26b with a variable geometry, in this case a slide-away overhanging portion, shown in both released and stowed configurations;

FIG. 26d shows how embodiments of the step frame may consist of multiple bodies connected by a structure;

FIG. 26e shows how embodiments of the step frame may also consist of a single central body;

FIG. 27 shows perspective and side views of another variable geometry embodiment of the step frame with a lower portion that slidingly engages to an upper portion on a rail, allowing it to be configured for either ascending or descending;

FIG. 28a shows a perspective view and a side view of one embodiment of the step frame with a level finding capability by using two oppositely sliding panels;

FIG. 28b shows the level finding step frame from FIG. 28a adjusting to a step with a high riser;

FIG. 28c shows the level finding step frame from FIG. 28a adjusting to a step with a low riser;

FIG. 29a shows a perspective view and a side view of another embodiment of the step frame with level finding capability by using a four-bar mechanism;

FIG. 29b shows the level finding step frame from FIG. 29a adjusting to a step with an arbitrary riser height;

FIG. 30a shows a perspective view and a side view of another embodiment of the step frame with level finding capability by using a toothed pivot;

FIG. 30b shows the level finding step frame from FIG. 30a adjusting to a step with an arbitrary riser height;

FIG. 31a shows a perspective view and a side view of another embodiment of the step frame with level finding capability by using a lockable front leg;

FIG. 31b shows the level finding step frame from FIG. 31a adjusting to a step with an arbitrary riser height;

FIG. 32a shows a perspective view and a side view of another embodiment of the step frame with level finding capability by using a rotating and locking overhanging portion;

FIG. 32b shows the level finding step frame from FIG. 32a adjusting to a step with an arbitrary riser height;

FIG. 33a shows a perspective view and a side view of another embodiment of the step frame with level finding capability by using a front leg consisting of a variable linkage;

FIG. 33b shows the level finding step frame from FIG. 33b adjusting to a step with an arbitrary riser height;

FIG. 34a shows a perspective view of one embodiment of the stair traversing device that is capable of traversing multiple steps;

FIG. 34b shows a side view of the stair traversing device depicted in FIG. 34a executing a cyclical motion to traverse two stair steps;

Payload Body Embodiments

Figure 35A:
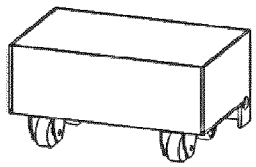
Figure 35A:
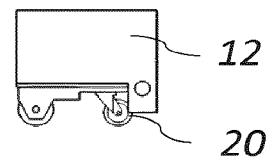
Figure 35B:
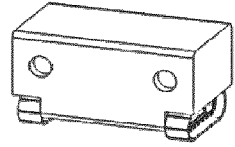
Figure 35B:
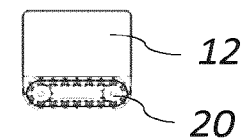
Figure 35C:
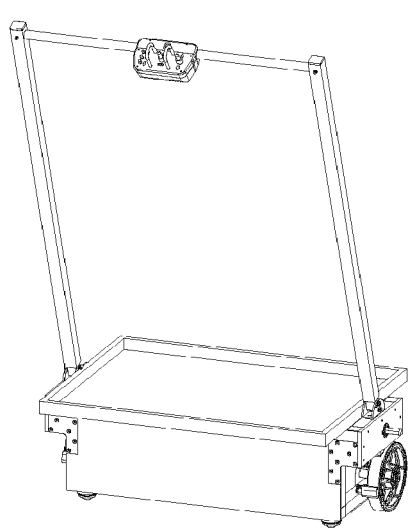
Figure 35C:
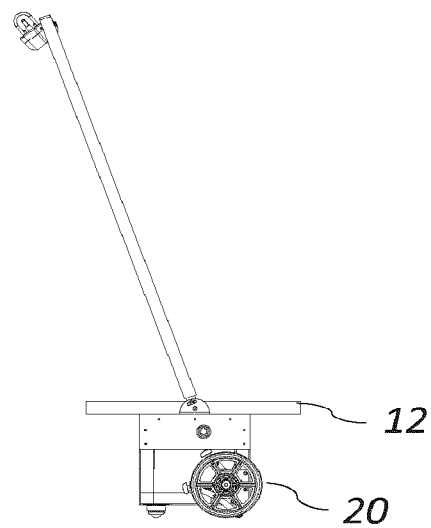
Figure 35D:
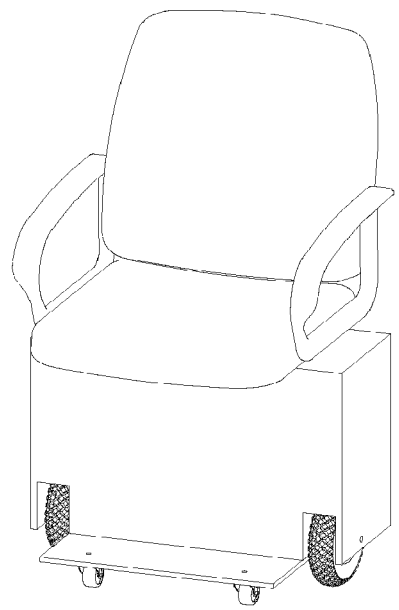
Figure 35D:
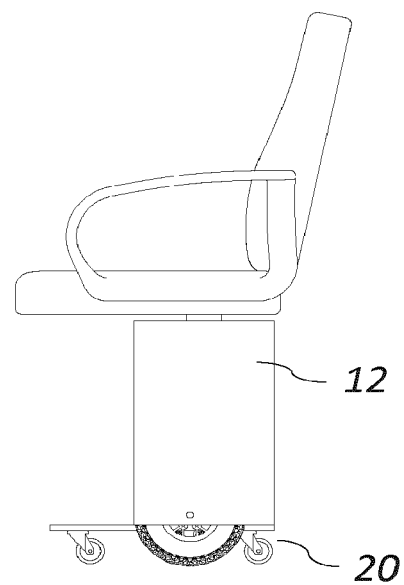

FIG. 35a shows a perspective and side view of a preferred embodiment of the payload body as a motorized robot;

FIG. 35b shows a perspective and side view of one embodiment of the payload body as a teleoperated vehicle;

FIG. 35c shows a perspective and side view of one embodiment of the payload body as a manually steered hand cart;

FIG. 35d shows a perspective and side view of one embodiment of the payload body as a wheelchair;

FIG. 36a shows a side view and perspective view of the payload body from FIG. 35a, depicting a wheel configuration consisting of a combination of fixed wheels and casters of similar size;

FIG. 36b shows a side view and perspective view of the payload body from FIG. 35c, depicting a wheel configuration consisting of a combination of fixed wheels and casters of dissimilar size.

Figure 37A:
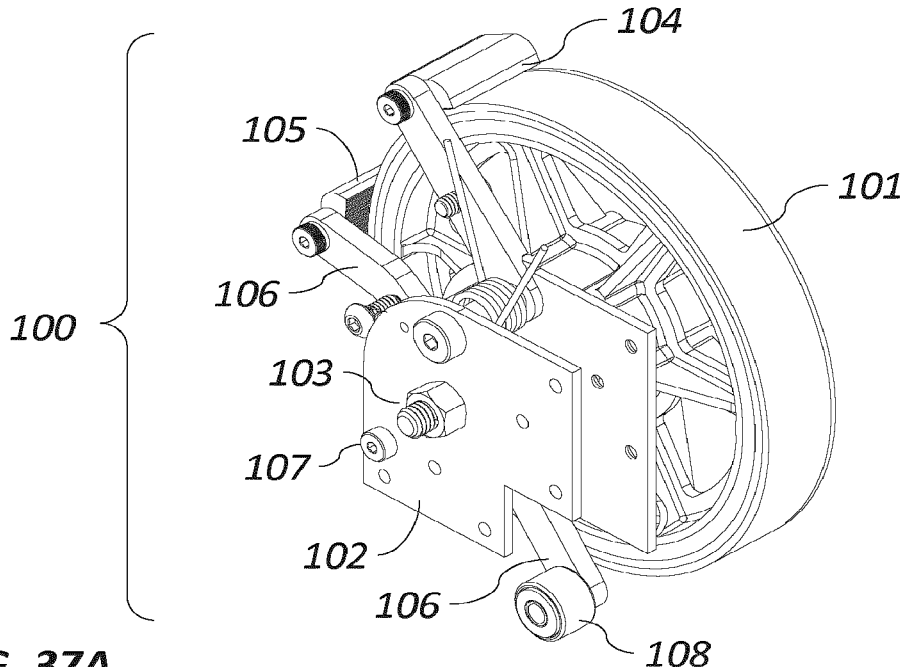
Figure 37B:
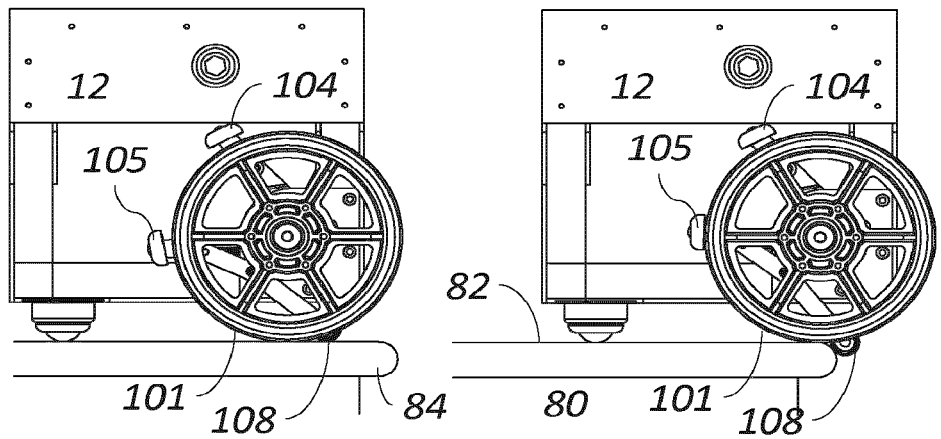
Figure 37C:
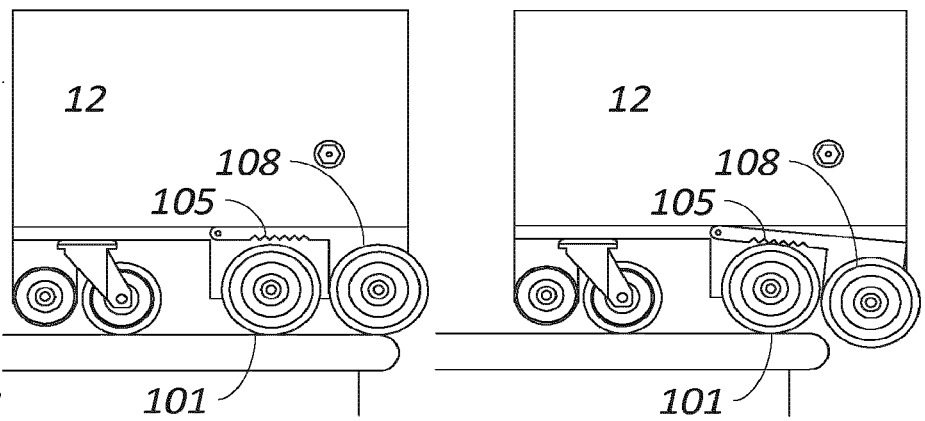

FIG. 36c shows a side view and perspective view of the payload body depicting a wheel configuration with auxiliary stabilizing wheels that may also be used as part of an edge detection braking system;

FIG. 36d shows a side view of the payload body from FIG. 36c when it is on the floor as well as when it is on a step;

FIG. 37a shows a perspective view of an edge detection braking feature;

FIG. 37b shows a side view of the braking feature depicted in FIG. 37a in both its disengaged and engaged form upon detection of the edge of a step;

FIG. 37c shows a side view of the braking feature depicted in FIG. 35c in both its disengaged and engaged form upon detection of the edge of a step;

Preferred and Alternative Embodiments of the Device

Figure 38:
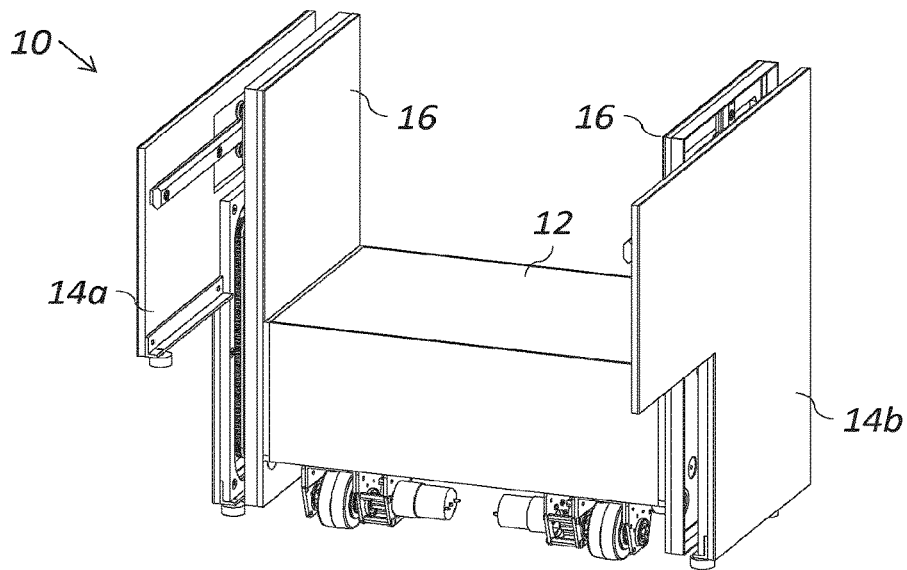
Figure 38:
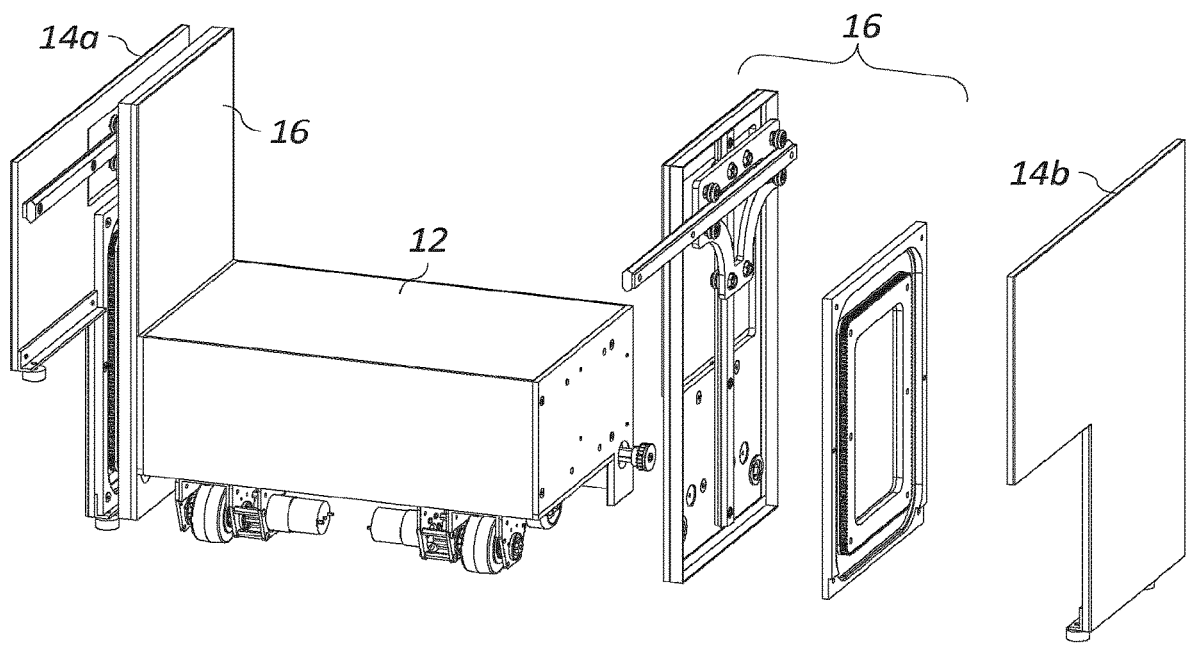

FIG. 38 shows a perspective and exploded perspective view of a preferred embodiment of a stair traversing device in the form of a service robot.

Figure 39:
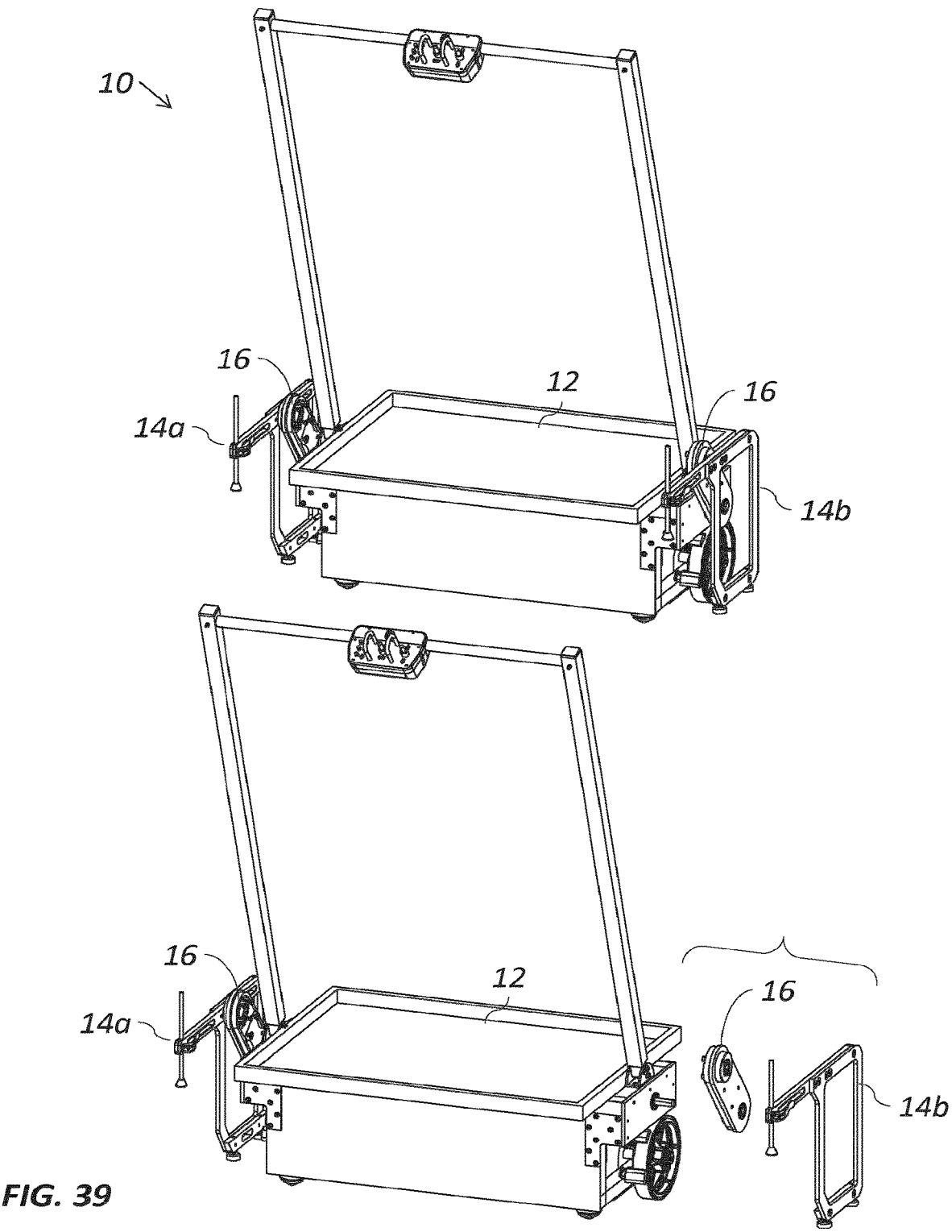
Figure 40:
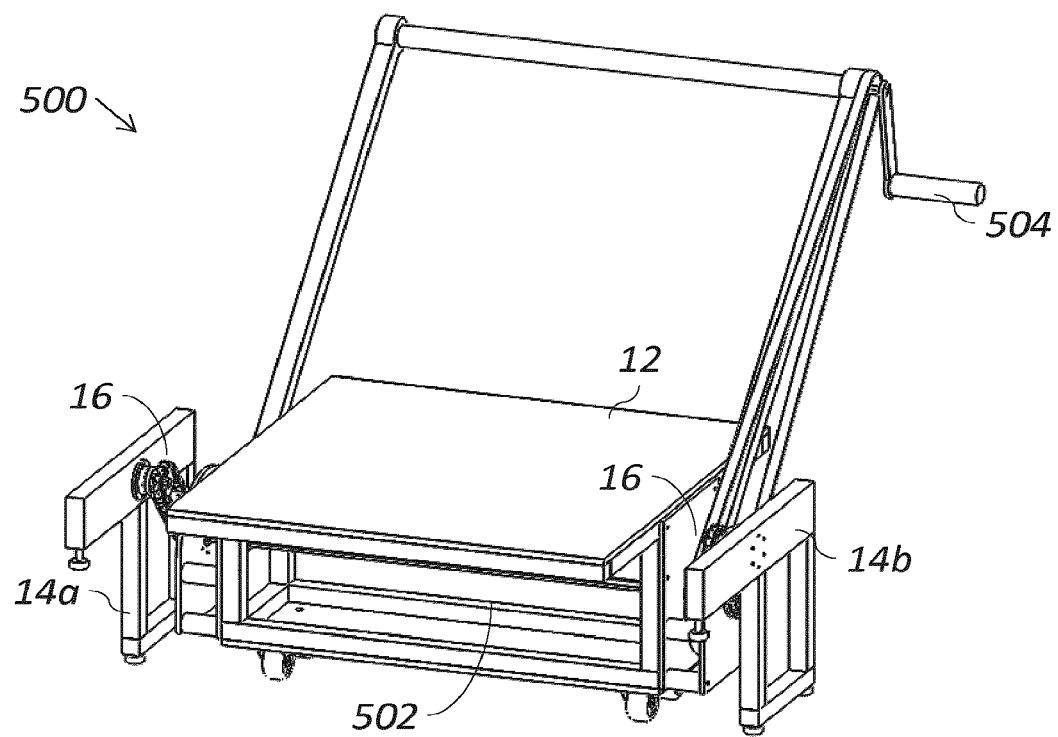

FIG. 39 shows a perspective and exploded view of a preferred embodiment of manually steered stair traversing device in the form of a hand cart;

FIG. 40 shows a perspective view of a manually powered version of the hand cart depicted in FIG. 39.

Figure 41:
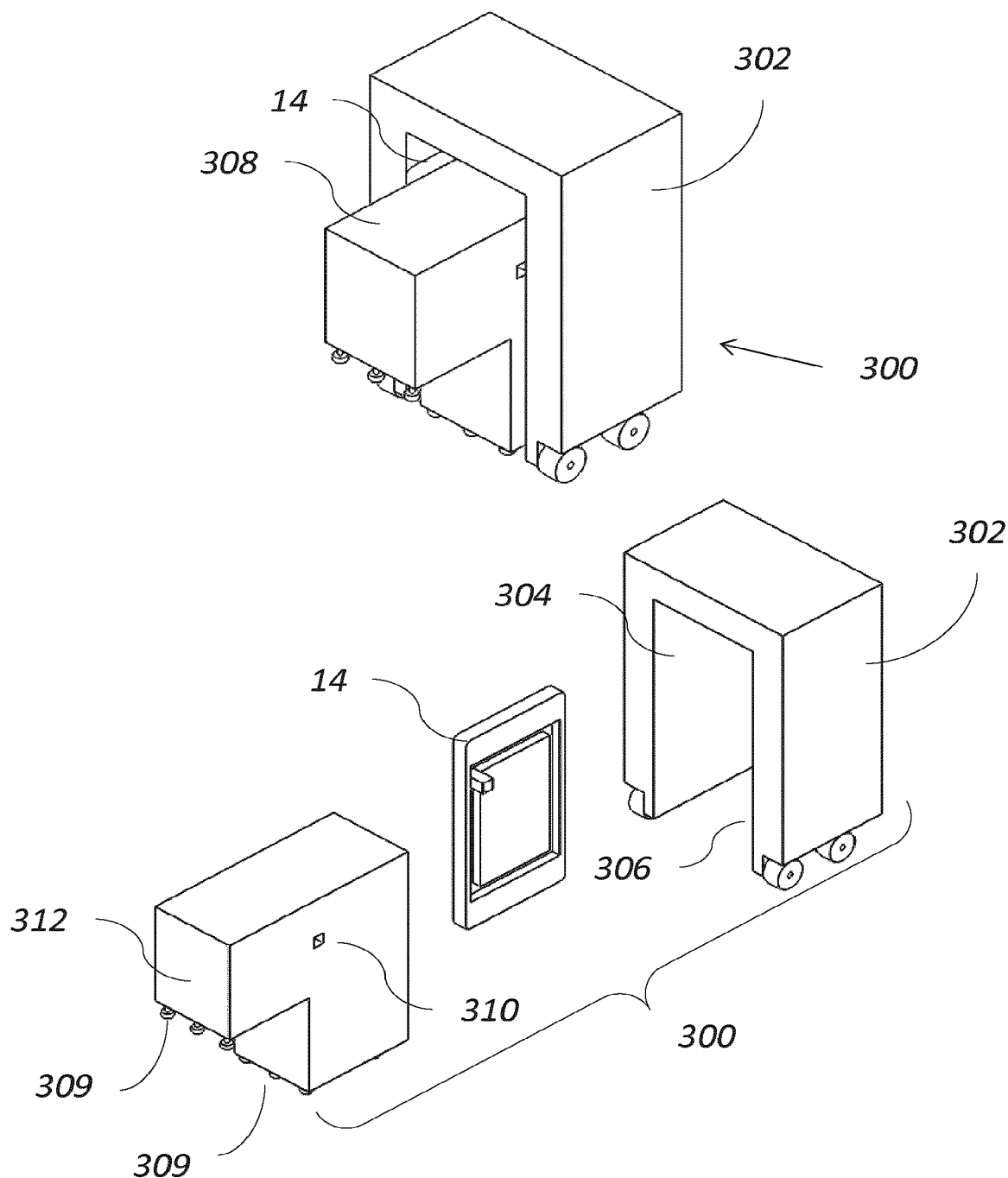

FIG. 41 shows a perspective and exploded view of one embodiment of the stair traversing device utilizing a climbing frame assembly consisting of a single central body.

DETAILED DESCRIPTION OF THE DRAWINGS

In the following description, like numerals refer to like components.

Parts of the Device

Entire Device

As depicted in FIG. 1, the stair traversing device 10 is in accordance with one embodiment of the present invention. The stair traversing device 10 comprises a payload body 12 capable of carrying loads in an essentially level orientation. A uniquely shaped step frame 14, consisting of two instances of similar co-moving bodies 14a and 14b in this embodiment, are connected, each via a mechanism 16, to two opposing sides of the payload body 12.

Figure 2:
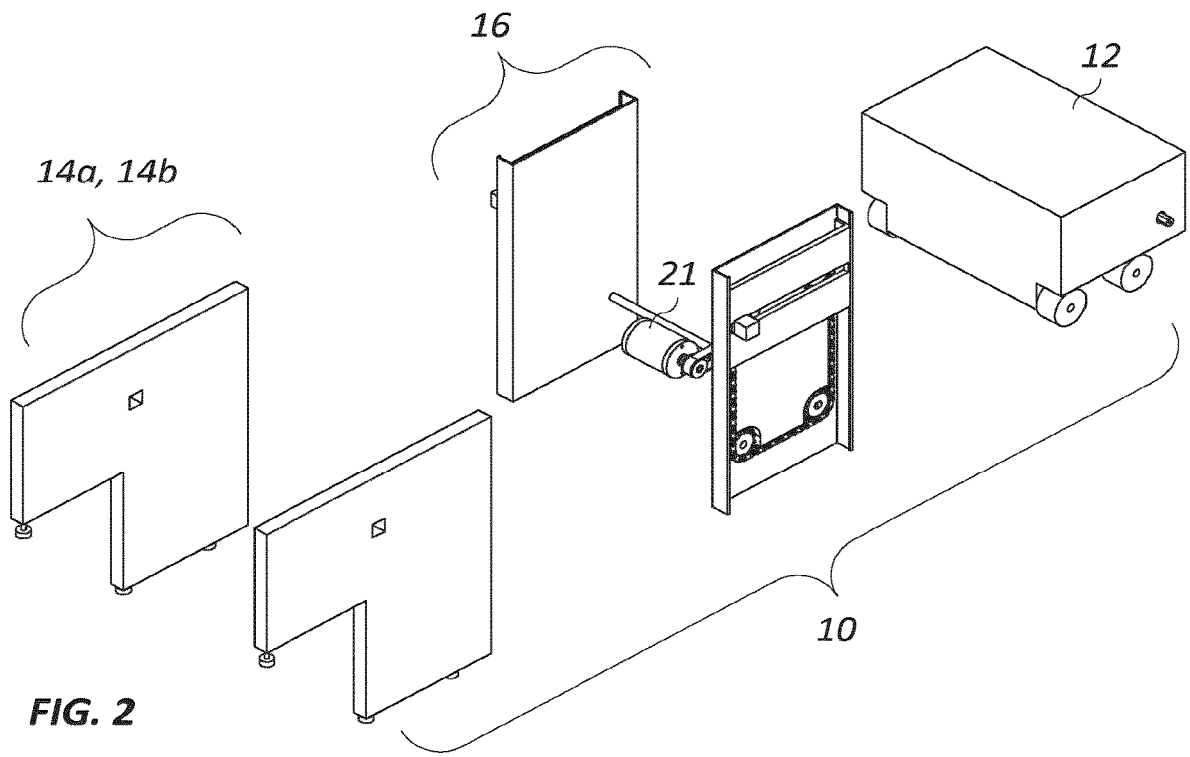
FIG. 2 shows an exploded perspective view of the stair traversing device shown in FIG. 1.

FIG. 2 shows an exploded view of the embodiment of the stair traversing device 10 shown in FIG. 1. The actuator 21 that drives the mechanism 16 is preferably housed within the payload body 12.

Payload Body

Figure 3A:
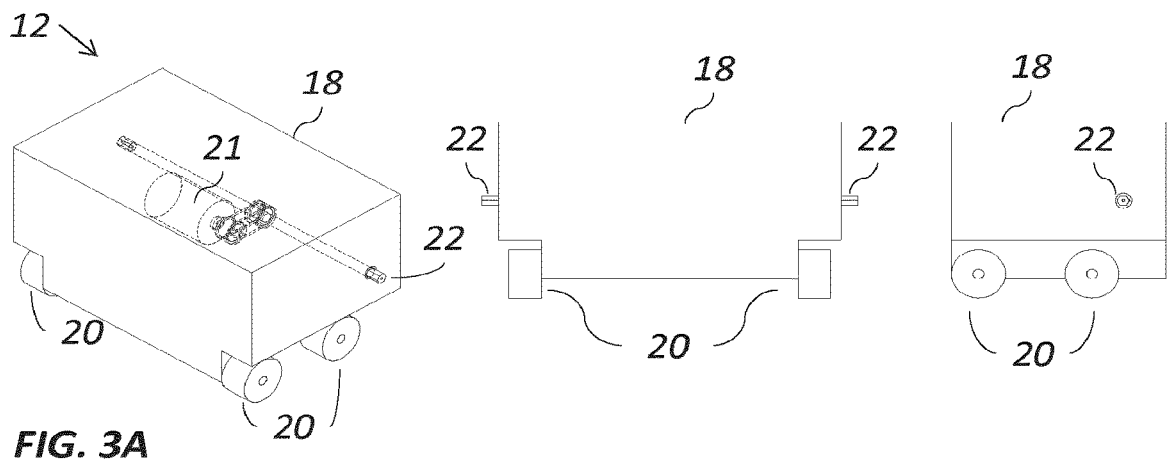
FIG. 3a shows a front, side, and perspective view of one embodiment of the payload body.

FIG. 3a illustrates one embodiment of the payload body 12. In the embodiment shown, the payload body 12 comprises a rigid casing 18 with movement supports 20 in the form of wheels. Other types of possible movement supports are tracks, treads, legs, feet, or any other suitable means to facilitate horizontal movement. The payload body 12 further comprises a drive shaft 22. In this embodiment, the drive shaft 22 is driven by a motorized actuator 21 situated inside the casing 18. In other embodiments, the drive shaft 22 may be driven manually via an external crank. As will be discussed in detail below, the drive shaft 22 will drive the mechanism in facilitating the movement of the step frame 14 relative to the payload body 12. All necessary control logic circuitry or power sources may be housed within the casing 18.

As depicted in FIG. 3b, the casing 18 further comprises a load carrying surface 26.

FIG. 3c shows how the movement supports 20 on the payload body 12 are arranged to allow it to carry a load 28 in a nominally level orientation either on a step 80 or on the floor 90.

Figure 3D:
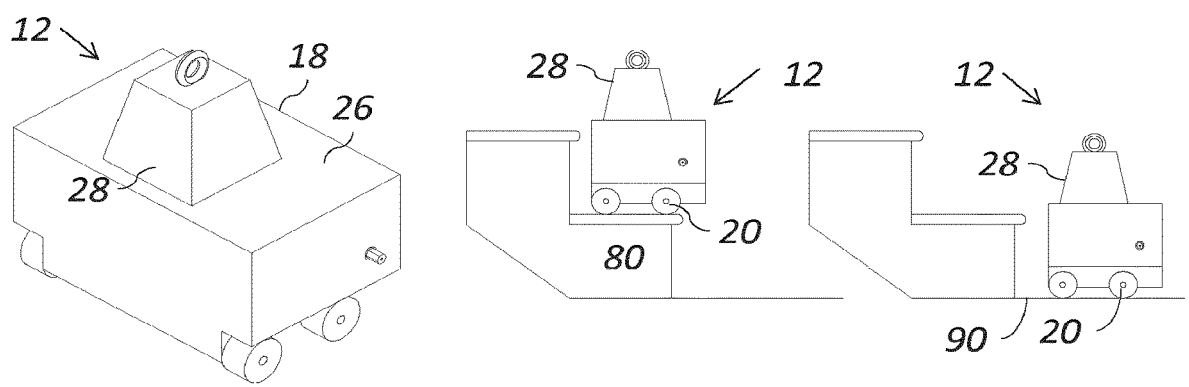
FIG. 3d shows a side view of the payload body having auxiliary stabilizing means that react to features of the steps.
Figure 3D:
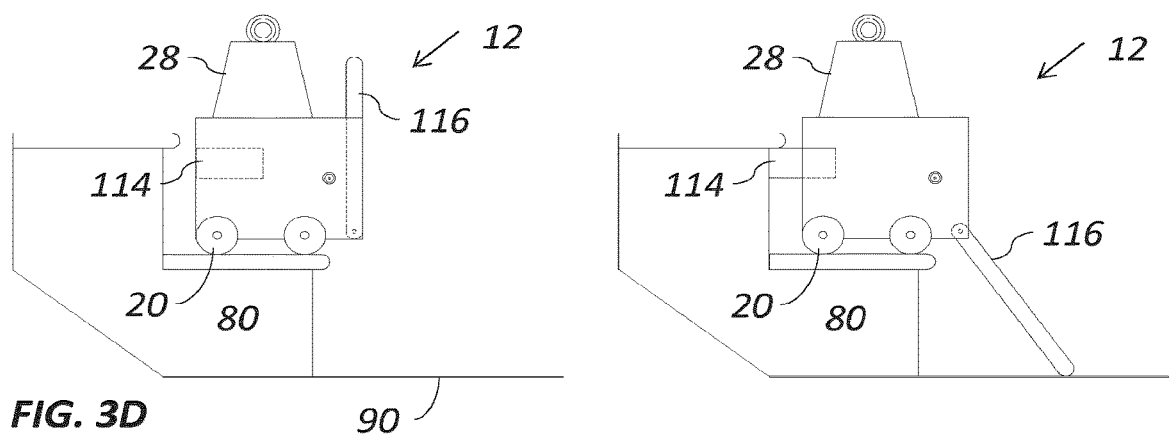

FIG. 3d shows how the payload body 12 carrying load 28 may also remain level and stable on a step 80 through a combination of movement supports 20 (shown as wheels) and auxiliary stabilizing arms 114 and 116 that react against features on the same step or a different step, respectively.

Step Frame

Figure 4:
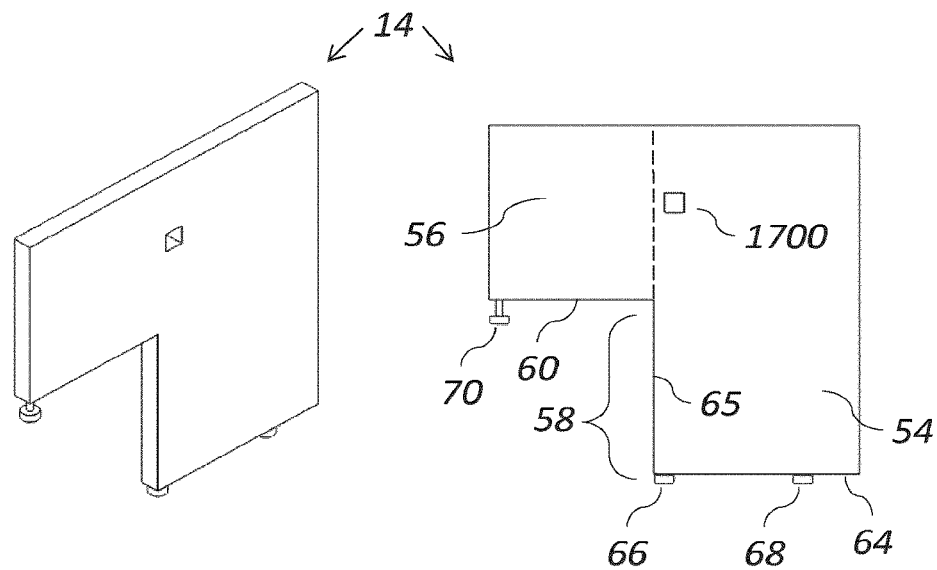
FIG. 4 shows a perspective and side views of one embodiment of the step frame.

With reference to FIG. 4, this embodiment of the step frame 14 comprises a main body portion 54 and an overhanging portion 56, as separated by the imaginary dotted line. The essentially horizontal overhanging portion 56 is at a height 58 above from the bottom of main body 54. Height 58 is at least greater than the height of a single stair step. The elevated overhanging portion 56 makes the step frame essentially conform to the shape of a stair step. The main body portion 54 has a bottom surface 64 comprising support features 66, 68. In this embodiment, the main body portion 54 also has an essentially vertical surface 65. Additional support features 70 are located on surface 60. Surfaces 60, 64, 65 and support features 66, 68, 70 are designed for contacting with and reacting against one or more surfaces or features of a step to ensure that the stair traversing device 10 remains in static equilibrium while ascending or descending the step.

Figure 5A:
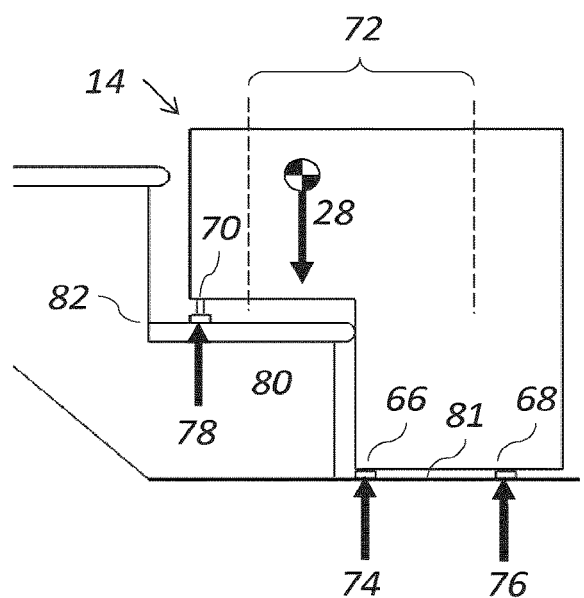
FIG. 5a shows a side view of the embodiment of the step frame shown in FIG. 4 illustrating the forces acting on the frame assembly for a range of load positions.
Figure 5B:
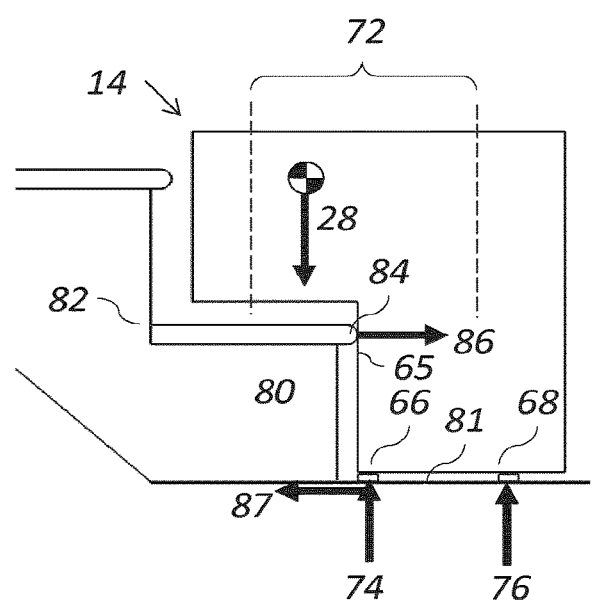
FIG. 5b shows a side view of the embodiment of the step frame shown in FIG. 4 and the forces acting on the frame assembly for a range of load positions while the frame assembly is cantilevered against a step.

FIGS. 5a and 5b show how the step frame 14 can support a predominantly downward vertical load 28 at various positions over a horizontal range 72 while maintaining static equilibrium.

In FIG. 5a, the supporting features 66, 68, and 70 provide vertical reaction forces 74, 76, and 78, respectively, against surfaces 81 and 82 of step 80 to balance the weight of the load 28 over its entire range of motion 72.

In FIG. 5b, where the upper section of the step frame 14 is cantilevered over the step 80 (with support feature 70 removed), the load 28 is balanced by vertical reaction forces 74, 76 against surface 81, a horizontal reaction 86 on surface 65 at the nose of the tread 84, and a horizontal frictional component 87 at the fore-most support feature 74.

Mechanism

FIG. 6 shows one embodiment of the mechanism 16 which comprises a main body portion 1601 which, in this embodiment, is rigidly attached to the payload body 12. In other possible alternative embodiments, the main body portion 1601 may be rigidly attached to the step frame. The main body portion 1601 has vertical rails 1610. A carriage 1620 slidingly engages the vertical rails 1610. In this embodiment, a non-rotating connection consists of a square lug 1602 that slidingly engages the parallel sides of a rectangular guide slot 1603 within the carriage 1620, which prevents the lug 1602 from rotating as it moves along the guide slot 1603, and as the carriage 1620 moves along the rails 1610. The cyclical motion mechanism is implemented by way of three idle sprockets 1164 and one driven sprocket 164 connected by a chain loop 162. The climbing drive shaft 22, driven by actuator 21, engages with sprocket 164, causing the chain loop to move. The lug 1602 is rotatably attached to one link in the chain loop 162 by means of a pin 166, such that the lug moves with the chain loop. The lug is attached to a corresponding feature 1700 in the step frame 14.

Stair Traversing Method

FIG. 7 illustrates how the cyclical motion produced by the mechanism 16 results in stair traversing motion when the mechanism is attached to the step frame 14.

FIG. 7a shows the mechanism 16 in a sequence of states. First, the non-rotating connection 1602 is in its initial position. Then, when the actuator 21 is activated, drive shaft 22 turns in direction 23, causing connection 1602 to move along the first segment 481 of a rectangular-shaped cyclical path 48 that corresponds to the shape of the chain loop 162 shown in FIG. 6B. Finally, the connection 1602 moves along the second segment 482 of the cyclical path, returning to its initial position.

When executed in a counter-clockwise direction 23 as shown, the first path segment 481 consists of a downward vertical stroke and a rearward horizontal stroke, while the second path segment 482 consists of an upward vertical stroke and a forward horizontal stroke. These sequences may be reversed by changing the direction 23 from counter-clockwise to clockwise.

FIG. 7b is a partially exploded view showing the mechanism 16 attached to the payload body 12 and the step frame 14. The step frame 14 is attached to the non-rotating connection 1602 by means of a corresponding feature 1700. Hence, the step frame 14 moves with the non-rotating connection 1602.

FIG. 7c shows the same sequence illustrated in FIG. 7a, now with the fully assembled stair-traversing device 10. The mechanism 16 moves move the step frame 14 with regards to the payload body 12 along a cyclical path 48. The step frame 12 moves from a retracted configuration to an extended configuration relative to the payload body 12 along the first segment 481 of the cyclical path 48, then from the extended configuration back to the retracted configuration along the second segment 482.

FIG. 7d shows the same sequence as FIG. 7c with the stair-traversing device 10 placed on the first level 81 of step 80. In the retracted configuration, both the payload body 12 and the step frame 14 are on the first level 81. When the frame is driven along first segment of the cyclical path 481, the device 10 is in an extended configuration where payload body 12 and frame 14 are on different levels 81 and 82, respectively. Finally, the frame is driven along second segment of the cyclical path 482, returning the device 10 to its retracted configuration, with the payload body 12 and frame 14 on the same level 82.

The sequence shown in FIG. 7 corresponds to an ascending motion. By reversing direction 23, an equivalent descending motion may be achieved.

FIG. 8 illustrates in more detail how the embodiment of the stair traversing device 10 as shown in FIG. 1 uses a cyclical motion of the step frame 14, as illustrated in FIG. 7, to ascend a staircase.

Figure 8A:
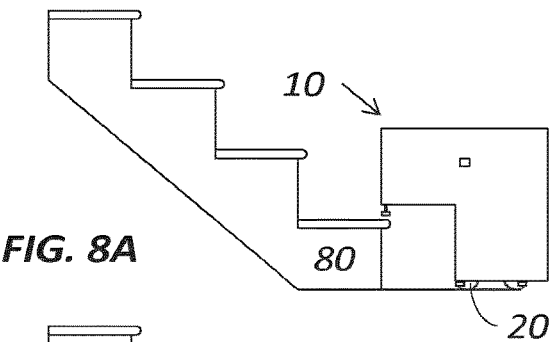

FIG. 8a shows the stair traversing device 10 approaching step 80. The weight of the device and its payload is fully supported by the movement features 20 of the payload body.

Figure 8B:
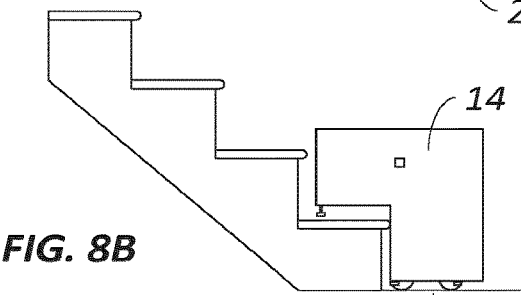

In FIG. 8b, the stair traversing device 10 is in an initial retracted configuration on the first step 80. Both the payload body and the step frame 14 are on level 81.

Figure 8C:
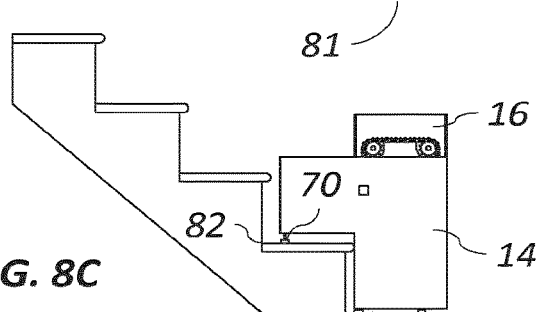

In FIG. 8c, the cyclical motion has commenced. The weight of the device 10 has been transferred from the payload body (hidden) to the step frame 14. Preferably, support features 66, 68 make contact with the lower level 81 and support feature 70 makes contact with the step surface 82. The mechanism 16 (with payload body 12, hidden) is ascending.

Figure 8D:
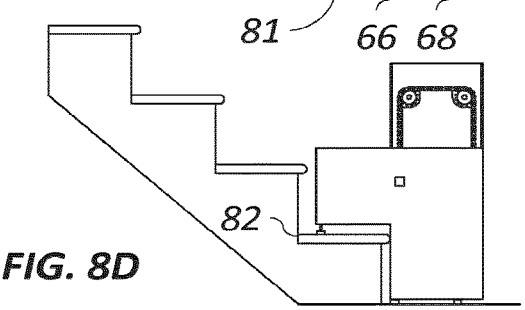

In FIG. 8d, the downward vertical stroke of the cyclical motion mechanism allows the payload body 12 (hidden) to ascend to a height that clears the level of the step 82.

Figure 8E:
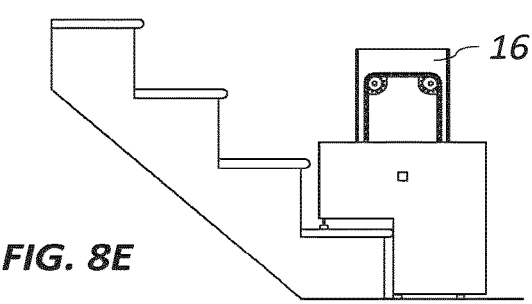

In FIG. 8e, the rearward horizontal stroke of the cyclical motion mechanism drives the payload body (hidden) and mechanism 16 to advance horizontally.

Figure 8F:
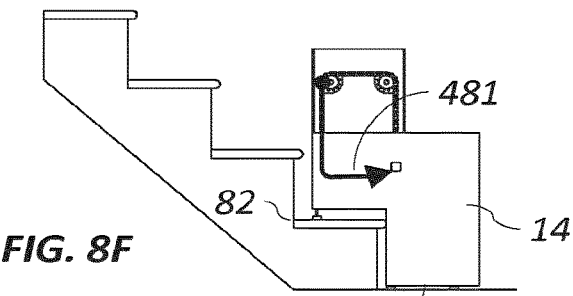

In FIG. 8f, the first segment of the cyclical path 481 is complete. The device 10 is now in an extended configuration with step frame on level 81 and payload body on level 82.

Figure 8G:
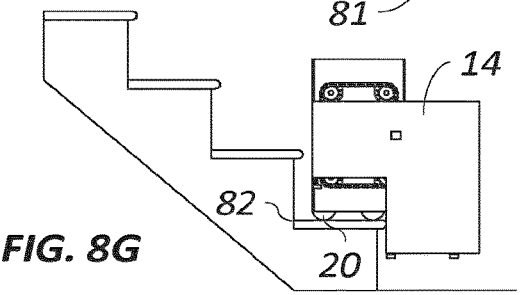

In FIG. 8g, the weight has been transferred back from the step frame 14 to the payload body's movement features 20 and the device 10 is now supported on surface 82. Cyclical motion continues as the step frame 14 is now lifted.

Figure 8H:
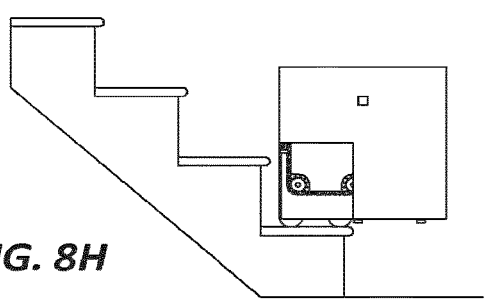

In FIG. 8h, at the apex of the upward vertical stroke, the step frame 14 is at a height that is sufficient to clear the first step 82.

Figure 8I:
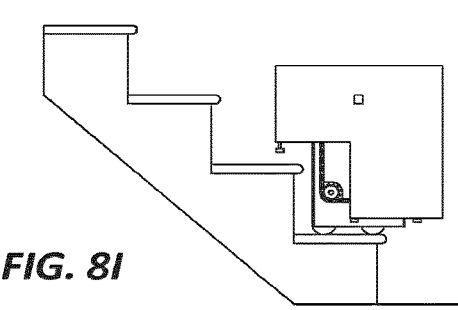

In FIG. 8i, the forward horizontal stroke of the cyclical path moves the step frame 14 towards its original state relative to the payload body 12.

Figure 8J:
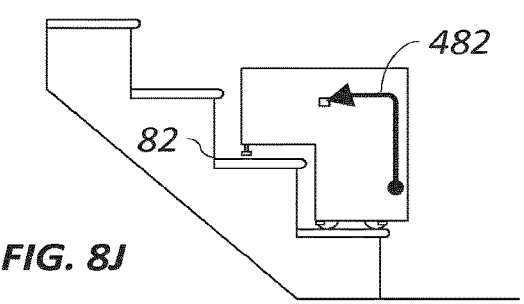

Finally, in FIG. 8j, the second segment of the cyclical path 482 is now complete, and the stair traversing device 10 is back in a retracted configuration on surface 82.

FIG. 9 illustrates the shifting of center of gravity 92 of the stair traversing device 10 and payload (hidden) during the cyclical motion described above. It is to be noted that the device 10, with or without payload, remains statically stable throughout the stair traversing sequence.

Figure 9A:
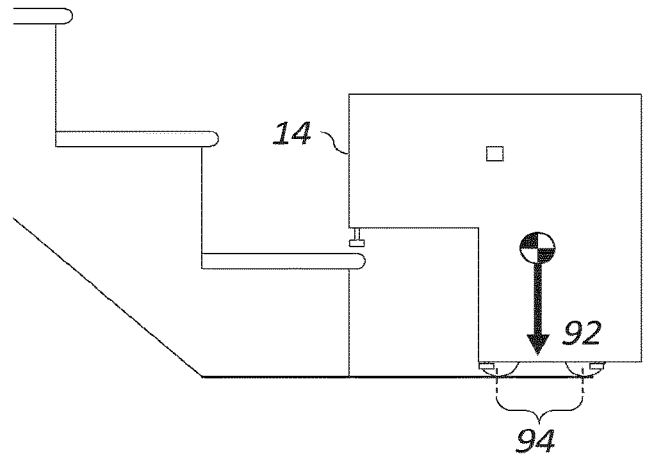

In FIG. 9a, the centre of gravity 92 rests with the payload body above the ground and would be well supported over the entire range of positions 94.

Figure 9B:
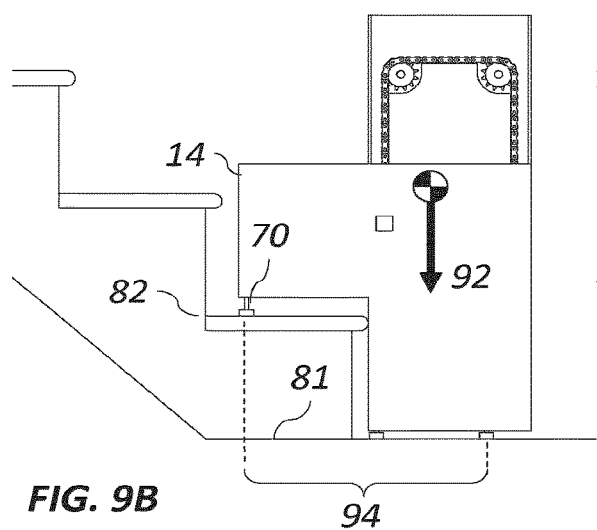
Figure 9C:
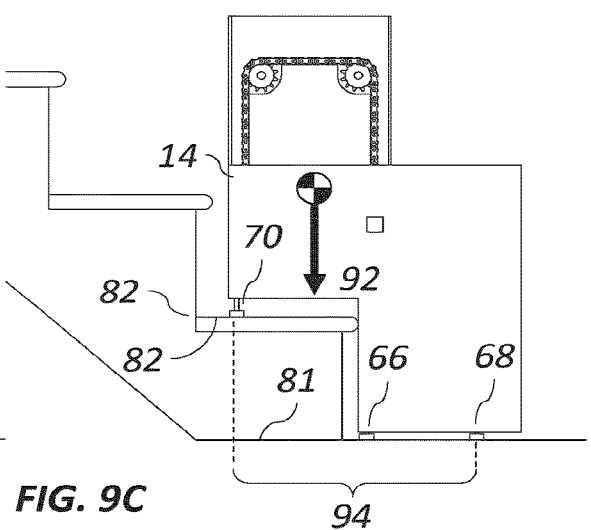

As shown in FIGS. 9b and 9c, support of the centre of gravity 92 shifts to the step frame 14 as the payload body, with or without load, ascends to clear the height of the first step 82. As mentioned above, preferably, the support features 66, 68, and 70 make contact with surface 81 and surface 82 so that the payload body 12, with or without load, is fully supported over the entire range of positions 94.

Figure 9D:
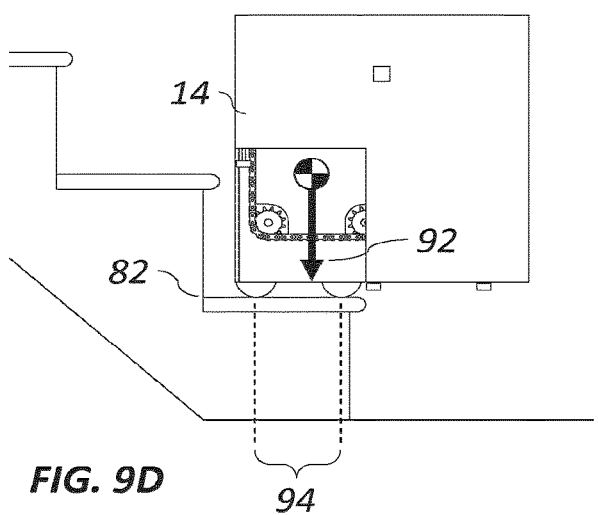
Figure 9E:
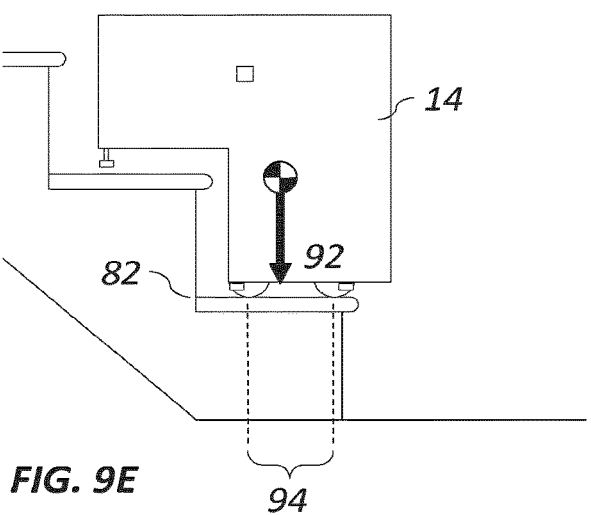

In FIGS. 9d and 9e, when the weight of the device 10 is transferred back onto the payload body 12, the centre of gravity 92 shifts to reside fully within the payload body 12 again. Since the step frame 14 is light-weight compared to the payload body 12, changes in its horizontal position have a comparatively small impact on the position of the center of mass 92 over the range of positions 94.

Mechanism Embodiments

Non-Rotating Carriage Assembly

FIG. 10 shows a preferred embodiment of a non-rotating connection within a mechanism 16 which takes the form of a non-rotating carriage assembly 31.

In FIG. 10a, the non-rotating carriage assembly 31 comprises a back panel 1190 which is rigidly attached to both sides of the payload body 12 for moving integrally therewith. Two vertical rails 1194 are attached to the back panel 1190 near its outer two vertical edges. A carriage 1191 contains, on a first surface, two sets of vertical rollers 1193 capable of rolling freely on the surface of the vertical rails rail 1194. On a second surface, opposite to first surface, two sets of horizontal rollers 1192 are positioned for rolling freely on the surface of a horizontal rail 1195. As shown, two attachment points 44 are located near both the distal and proximal ends of the horizontal rail 1195 respectively for attaching to the frame assembly 14 (not shown). The horizontal rail thereby moves integrally with the step frame. In another embodiment, the horizontal rail may be integrally formed with the step frame.

FIG. 10b illustrates how the non-rotating carriage assembly 31 permits the translational motion of the horizontal rail 1195 in both the horizontal direction 1197 and the vertical direction 1198. When connected to the step frame 14 (not shown) by means of attachment points 44, the same twodimensional translation freedom is imported to the step frame relative to the mechanism 16, and therefore the payload body 12 (not shown). At the same time, the non-rotating carriage assembly prevents the frame 14 from rotating relative to the payload body 12.

Chain Loop Mechanism

A preferred embodiment of the mechanism 160 that executes a rectilinear cyclical path utilizing a chain-loop is illustrated in FIG. 11.

In this embodiment, the mechanism 160 contains a non-rotating connection in the form of a non-rotating carriage assembly 31 similar to the one shown in FIG. 4a. The cyclical motion mechanism is embodied as a chain-loop 162 that is actuated by a drive shaft 22 originating in the payload body 12. As discussed above, the drive shaft 22 may be motorized or human-powered. The drive shaft 22 turns one of the four sprockets 164, which causes the chain loop 162 to advance around all four sprockets 164 as shown. A step frame 14 is attached to the mechanism 160 by attachments points 44. A connection pin 166, attached to a specialized link (not shown) in the chain loop 162, is attached to a corresponding bore 170 on the step frame 14. As any person skilled in the art may appreciate, in the above embodiment, the sprockets 164 and chain loop 162 may be replaced by similar or equivalent means such as timing belts, belt loops, rack-and pinion, lead screws, and pulleys to achieve equivalent results.

The corresponding stair traversing sequence for the above embodiment is depicted in FIGS. 12a to 12d. As the drive shaft 22 turns one of the sprockets 164, chain-loop 162 rotates around the other sprockets. In turn, the connection pin 166 moves the step frame 14 along the chain-loop 162 in a rectilinear cyclical path. This allows the step frame to execute the cyclical climbing motion similar to that discussed above.

As can be appreciated by a person skilled in the art, the above embodiment shown in FIG. 11 shows a chain-loop 162 driven by a single actuator.

FIG. 13 shows an alternative embodiment of a chain loop mechanism 1600 in which the chain loop 162 is arranged in a trapezoidal shape. Coupled with an appropriately shaped step frame, the trapezoidal chain loop 162 will move such a step frame in predominantly diagonal fashion past the step to minimize cycle time.

Looped Rack Mechanism

In another preferred embodiment, the mechanism 16 may include a cyclical motion mechanism comprising a driven toothed pinion gear configured to traverse a toothed rack gear forming a planar rectilinear cyclical path.

As shown in FIG. 14a, this embodiment of the mechanism comprises a non-rotating connection in the form of a non-rotating carriage assembly 31 and a cyclical motion mechanism 53 that consists of an inner track 50 and an outer track 52. The inner track 50 fits within the hollowed center of outer track 52. When assembled, the inner track 50 and outer track 52 form a rigid structure, such that the gap between tracks remains fixed. The outer circumference of the inner track 50 is lined with toothed rack gear 49, forming a closed rectilinear loop.

A toothed pinion gear 24, corresponding to the toothed rack gear 49, is affixed to the drive shaft 22, which in turn is driven by an actuator in the payload body 12. The actuator may be motorized or human-powered. As any person skilled in the art may appreciate, the embodiment requires only one actuator to drive the drive draft 22.

As shown in the detail, the toothed pinion gear 24 is constrained to follow and remain in engagement with toothed rack gear 49 over the entire loop. In this embodiment, the constraint is provided by the outer track 52, such that the toothed pinion gear 24 always remains within the gap between tracks 50 and 52. The center of the pinion 24 follows a locus defined by the centerline 48 between tracks 50 and 52.

The assembly comprising inner track 50, toothed rack gear 49, outer track 52, together with the toothed pinion gear 24, form the cyclical motion mechanism 53.

Rotating the pinion gear 24 causes the cyclical motion mechanism 53 to move in a rectilinear fashion relative to the mechanism 16 with a path shape corresponding to the centerline 48. Reversing the rotation of the pinion gear 24 reverses the motion of the cyclical motion mechanism 53 along the same centerline 48.

As shown in the exploded view in FIG. 14b, the cyclical motion mechanism 53 is fixedly attached to the frame assembly 14 by means of attachment points 153. Since the frame assembly 14 is also fixedly attached to the attachment points 44 on the non-rotating carriage assembly 31, both the frame assembly 14 and the cyclical motion mechanism 53 are prevented from rotating relative to the payload body 12 and are only permitted to translate by the rectilinear motion of cyclical motion mechanism 53 as it is advanced by the pinion gear 24. The shape of the resulting cyclical path corresponds to the shape of the centerline 48.

The corresponding climbing or descending sequence for the above embodiment is depicted in FIGS. 15a to 15d. As the pinion gear 24 turns, the cyclical motion mechanism 53 executes a rectilinear cyclical path relative to the mechanism 16. In turn, this allows the step frame to execute the cyclical climbing motion similar to that discussed above.

In FIG. 16, an alternative embodiment of the cyclical motion mechanism 530 is shown. This embodiment illustrates an alternative mechanism used to restrain the pinion gear 24 to the toothed rack gear 49.

In particular, as shown in FIG. 16, the pinion gear 24 is constrained to the toothed rack 49 by a constraint mechanism 531. The constraint mechanism comprises a base plate 532 which has a first pin 534 located on the inside of rack frame 533. Two additional pins 536, 538 are located on the other side of the rack frame 533 from the first pin such that the pinion gear 24, located at the relative center of the base plate 532, is biased against the toothed rack gear 49 on the outer circumference of the rack frame 533. The drive shaft 22 connects to the pinion gear 24 through the base plate 532. As a skilled person may appreciate, similar or equivalent constraint mechanisms may be used.

It is to be noted that the loop rack need not be rectilinear, but may be configured in any suitable shape. Non-exhaustive examples of some of the possible loop rack shapes are shown in FIG. 17, including stadium shape and polygonal shapes with three or more distinctive sides.

Rotary Crank Mechanism

FIG. 18a shows another embodiment of the mechanism 360 which generates a circular cyclical motion utilizing a crank-arm 362.

In this embodiment, the mechanism 360 contains a non-rotating carriage assembly 31, similar to that shown in FIG. 10, and a crank-arm 362 that is actuated by a drive shaft 22 originating in the payload body 12. Again, the drive shaft 22 may be motorized or human-powered. The drive shaft 22 extends through an opening 363 in the main body 365 of the mechanism 360. It is to be noted that the length of the drive shaft 22 that extends through the opening 363 is at least greater than the width of the vertical rail 42 of the non-rotating carriage assembly 31, such that the crank-arm 362 may rotate unobstructed by the vertical rails 42.

As shown in the exploded view in FIG. 18b, a step frame 14 is attached to the mechanism 360 by attachments points 44. A pin 364 at the end of the rotating crank-arm 362 is attached to a corresponding bore 366 on the step frame 14.

As shown in the sequence depicted in FIGS. 19a to 19d, the cyclical path 368 produced by a crank-arm mechanism is circular.

Double Crank Arm Mechanism

FIG. 20a illustrates another embodiment of the crank-arm cyclical mechanism. In particular, a double-crank-arm mechanism 460 consisting of a primary arm 462 and a secondary arm 464. A pin 466, which connects to the frame assembly 14 (not shown), is attached to the end of secondary arm 464 that is opposite to the end at which the primary arm 462 and secondary arm 464 are rotatably connected.

In this embodiment, the primary arm 462 is actuated by a drive shaft 22, which may be motorized or human powered, through a non-rotating primary apparatus or pulley 463. The primary pulley 463 does not rotate relative to the payload body 12. The secondary arm 464 is connected at the other end of the primary crank arm 462 by a secondary apparatus or pulley 468. The two pulleys are connected by a connecting apparatus or belt 470. Any skilled person may appreciate that the belt 470 may be implemented by equivalent means, such as a chain or a series of gears, with corresponding changes to the two pulleys to achieve the same functionality. When the primary arm 462 is rotated by the drive shaft 22, the secondary arm 464 rotates relative to the primary arm 462.

As shown in the sequence depicted in FIG. 20b, a cyclical path 472 produced by the above double-crank-arm mechanism 460 is, in general, cycloidal. In the specific embodiment shown, the gear ratios and arm lengths have been selected to cause the pin 466 to execute a hypotrochoid path, which closely resembles a square with rounded corners.

Non-Rotating Hub Mechanism

It should be noted that the non-rotating connection and the cyclical motion mechanism within the mechanism do not necessarily have to be distinct features. It is possible to combine these two features into a single mechanism.

FIG. 21a (perspective) and FIG. 21b (exploded) show an embodiment of a combined mechanism 560 that incorporates a first non-rotating hub 562 at the end of a rotating crank-arm 564. The non-rotating hub 562 is rigidly connected to the step frame 14 (not shown). The first non-rotating hub 562, through a shaft 563, is rigidly connected to a first apparatus or sprocket 565. The other end of the crank-arm 564 is connected to the drive shaft 22 from the payload body 12 (not shown). The drive shaft 22 passes through a second non-rotating hub 566, which is rigidly connected to payload body 12 (not shown). Drive shaft 22 also passes through a second apparatus or sprocket 567 by means of a bearing 569 and turns the crank-arm 564. Sprocket 567 is rigidly fixed to the non-rotating hub 566. The two sprockets (565, 567) have the same diameter and are connected by a connecting apparatus or chain loop 570. When the crank-arm 564 rotates, the first sprocket 565 counter-rotates at the same angular rate, such that the first non-rotating hub 562 experiences a net-zero rotation relative to the non-rotating hub 566 and the payload body 12. Hence, this type of mechanism incorporates the non-rotating and cyclical motion features into a single mechanism.

In FIG. 21c, a circular cyclical path 574 is formed with the combined mechanism 560 depicted in FIGS. 21a and 21b.

As shown in FIG. 22a, the first non-rotating hub 562 connects to a corresponding connection feature 568 on the frame assembly 14, and the second non-rotating hub 566 is affixed to the main structure of the payload body 12.

FIGS. 22b to 22j illustrate how the circular cyclical motion may be executed using the crank-arm mechanism 560 shown in FIGS. 21a and 21b. Specifically, FIGS. 22b to 22i shows the relative positions of the payload body 12 and step frame 14 with respect to the stairs during one complete revolution of the combined mechanism 560 as shown in FIG. 21a. Again, the motion may be executed in reverse to descend the stairs.

Figure 22B:
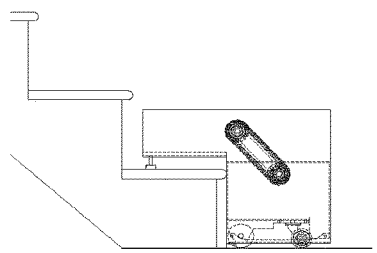

FIG. 22b—the stair traversing device is in a retracted configuration at the first stair level.

Figure 22C:
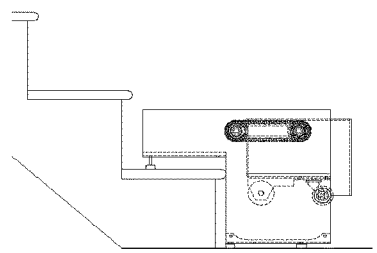

FIG. 22c—the weight of the device is shifted on the step frame 14 as the payload body 12 is raised.

Figure 22D:
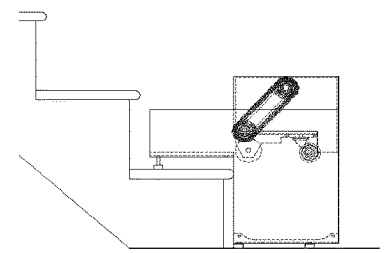
Figure 22E:
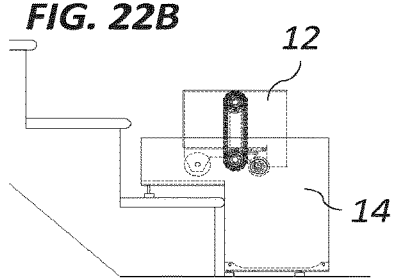

FIG. 22d and FIG. 22e—show the payload body 12 being rotated in a circular fashion.

Figure 22F:
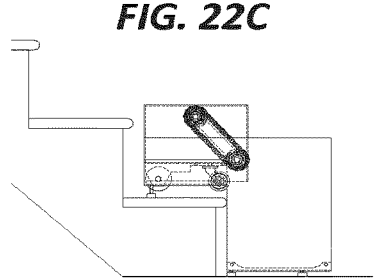

FIG. 22f—the device is in an extended configuration wherein payload body 12 makes contact with the next stair level.

Figure 22G:
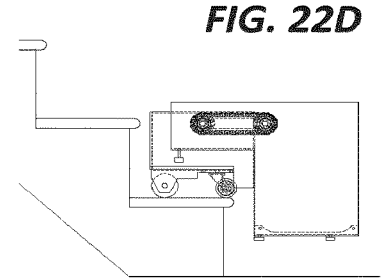

FIG. 22g—the weight of the device now shifts back to the payload body 12 as the step frame 14 is raised off of the first level.

Figure 22H:
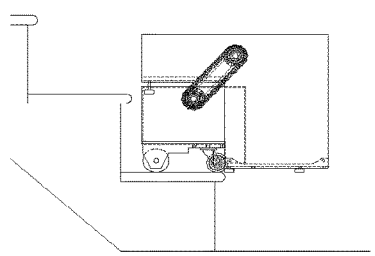
Figure 22I:
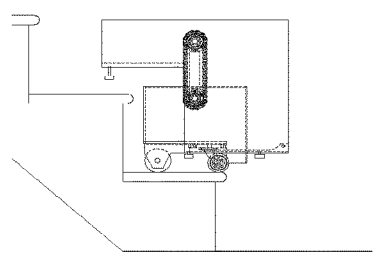

FIG. 22h and FIG. 22i—show the step frame 14 being rotated in a circular fashion.

Figure 22J:
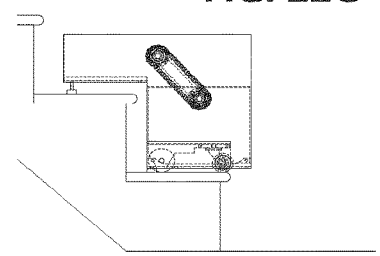

FIG. 22j—the circular cyclical path is completed and the device returns to its retracted configuration, now on the second level.

Alternative Non-Rotating Hub Mechanisms

FIGS. 23a to 23c illustrate an embodiment of a combined mechanism 590 that is equivalent to embodiment 560 in FIG. 21 except that the first and second rotating apparatuses, and the connecting apparatus, which were sprockets and chain loops, have been replaced with a series of gears.

Mechanism 590 that incorporates a first non-rotating hub 562 at the end of a rotating crank-arm 564. The non-rotating hub 562 is rigidly connected to the frame assembly 14 (not shown). The first non-rotating hub 562, through a shaft 563, is rigidly connected to a first main gear 585. The other end of the crank-arm 564 is connected to the drive shaft 22 from the payload body 12 (not shown). The drive shaft 22 passes through a second non-rotating hub 566, which is rigidly connected to payload body 12 (not shown). Drive shaft 22 also passes through a second main gear 587 by means of a bearing 569 and turns the crank-arm 564. Gear 587 is rigidly fixed to the non-rotating hub 566. The two main gears (585, 587) have the same diameter and are connected by a chain of gears 580 also with the same diameter. When the crank-arm 564 rotates, the first gear 585 counter-rotates at the same angular rate, such that the first non-rotating hub 562 experiences a net-zero rotation relative to the non-rotating hub 566 and the payload body 12.

In addition, any person skilled in the art will appreciate that the sprockets and chains may also be replaced by timing belts and pulleys with equivalent results.

FIG. 24 shows another embodiment of a combined mechanism 690 that incorporates a four-bar linkage. Drive shaft 22 passes through a first bearing (not show) in main body 680 and is rigidly fixed to a first sprocket 665. A second sprocket 667 is connected by shaft 661 to a second bearing (not shown) in main body 680. The sprockets 665, 667 are connected by a chain loop 670. A first crank arm 664 is rigidly connected to first sprocket 665 while a second crank arm 674, equal in length to arm 664, is rigidly connected to second sprocket 667, such that both crank arms turn in unison and remain parallel. A link 675 is connected to arm 664 by pin 676 and to arm 674 by pin 677. The centers of pins 676, 677 are same distance apart as the sprockets 665, 667. Link 675 is rigidly connected to the step frame (not shown). When shaft 22 is rotated, the link 665 (and hence the attached step frame) executes a circular cyclical path while maintaining the same orientation throughout.

Two Actuator Mechanism

FIG. 25 shows an alternative preferred embodiment a stair traversing device 3000 that achieves cyclical motion by using two actuators. Device 3000 comprises a payload body 12, a step frame 14 and a two-actuator mechanism 3100 that includes a vertical motion actuator 3200, here depicted as a ball-screw-type actuator, and a horizontal motion actuator 3300, here depicted as a rack-and-pinion-type actuator. FIG. 25 illustrates the mechanism 3100 in four stages of a rectilinear cyclical path. Since the two actuators 3200, 3300 may have their motions synchronized by an electronic control system, it is possible for the mechanism 3100 to execute cyclical paths with arbitrary shapes. Since the actuators are separate, their respective power outputs may be scaled independently, so that the horizontal actuator 3200 may have a higher power output in order to achieve heavier lifts. As can be appreciated by a person skilled in the art, the actuators 3200 and 3300 may be replaced by other mechanisms using chain loops, belts, or other devices to achieve equivalent results.

Step Frame Embodiments

As shown in FIGS. 26a and 26b (and in FIG. 4), in general the step frame 14 is shaped to be conformal to the different heights between steps, allowing to provide level, statically-stable contact with one or more steps. Step frame assemblies generally have a main body portion 54 and an overhanging portion 56 that is attached to the main body at a height 58 that is at least greater than the height of a single stair step.

As shown in FIG. 26a and FIG. 26b, the step frame 14 may consist, preferentially, of separate multiple bodies moving in unison, or alternatively, of multiple bodies connected by a structure (FIG. 26d), or a single body (FIG. 26e).

Fixed Geometry

In general, the step frame 14 may have a fixed geometry or a variable geometry. FIGS. 4 and 26a, 26b, 26d, 26e depict fixed geometry embodiments. The step frame may consist of solid bodies (FIG. 26a) or light-weight structures (FIG. 26b).

Variable Geometry

FIG. 26c depicts another embodiment of the frame assembly 640 with a slide-away overhanging portion 642 that may be retracted for convenience or storage, and that may be deployed immediately before ascending or descending a step.

FIG. 27 depicts a variable geometry frame assembly 740 in which the lower portion 742 can be re-configured forwards or backwards on a slide 744 rigidly attached along the bottom edge of a upper portion 741, allowing the variable geometry frame assembly 740 to assume either an ascending configuration 746 or a descending configuration 748 without reorienting the payload body 12 (not show) relative to the direction of motion 750. Similar to the other step frame designs, assembly 740 attaches to a mechanism (not shown) through bore 749.

Level Finding

The stair traversing device 10, and particularly the step frame 14, may possess level-finding capability.

FIG. 28a depicts one embodiment of the level-finding variable geometry step frame 140 in which the main body portion 141 comprises two slides 142, 143. A first frame panel 144 and a second frame panel 145 are each to slide freely upon the slides 142, 143 respectively. Each of frame panel 144 and 145 has toothed rack 146 and 147 on the side surfaces of the two panels that face each other. Additionally, the first frame panel 144 and the second frame panel 145 are connected by pinion gear 148 that correspondingly engages the toothed racks 146 and 147, such that when connected, the two portions move in opposite vertical directions.

When the main body portion 141 is lowered, one or the other panel (144 or 145) makes first contact with either the upper or lower step. Then, the two panels may move in opposite vertical directions such that one of the panels is lowered, and the other panel raised, until both panels make contact with both steps.

For example, FIG. 28b shows the step frame 140 lowering onto a comparatively high step 801. When the main body portion 141 descends towards the first step, the rear panel 144 contacts the lower level 81 first. The rack-and-pinion (146, 148) causes the panels to move in opposite directions until both panels (144, 145) are in contact with their respective levels. In this configuration, the step frame 130 is in static equilibrium.

FIG. 28c shows the step frame 140 lowering onto a comparatively low step. Note that the final configuration of panels 144, 145 in this figure differs from that in FIG. 28b, due to the difference in height between steps 801 and 802.

FIG. 29a illustrates another embodiment of the frame assembly with level-finding capability, in particular, a level-finding frame assembly 240 based on a four-bar mechanism 242. The main body portion 241 attaches to a mechanism (not shown).

In FIG. 29b, the level finding frame assembly 240 lowers onto a set of steps. First, the rear support feet (247, 248) make contact with the lower level 81. The main body portion 241 will continue to descend vertically until the front support foot 246 makes contact with the upper level 82. When all support feet (246, 247, 248) have made contact with their respective levels, the step frame 240 is in static equilibrium.

FIG. 30a depicts another embodiment of the level finding frame assembly 340 consisting of a supporting body portion 341, a mounting body portion 342 and a rotating body portion 344 defining the main body portion and the overhanging portion. The main body portion 341 attaches to a mechanism (not shown) and slides vertically relative to the mounting body portion 342 by means of slot features 343. The rotating body portion 344 is attached to the mount body portion 342 by a pivot feature 345. The rotating body portion also has a clamping surface 347 that, when engaged by the main body portion 341, prevents the rotating body portion 344 from rotating. The rotating body portion has a front support 346 and a rear support 348, here depicted as a wheel.

In FIG. 30b, the level finding frame assembly 340 lowers onto a set of steps. First, the rear support 348 makes contact with the lower level 81. As main body portion 341 continues to descend vertically, the rotating body portion 344 rotates until I the front support foot 346 makes contact with the upper level 82. When both supports (346, 348) have made contact with their respective levels, the main body portion 341 slides down and clamps onto the rotating body portion 344, preventing it from rotating any further. The step frame 340 is now in static equilibrium.

FIG. 31a illustrates another embodiment of the level-finding frame assembly 440 in which the front leg 446 is free to move vertically relative to the main portion 441 until a locking bolt 444 slides forward and engages the front leg stem 442. The locking bolt 444 is mechanically linked by a pin-in-slot feature 449 to a lower moving leg 447 that is free to move vertically relative to the main body portion 441. When not under load, moving leg 447 is kept extended by spring 445. When the lower moving leg 447 slides upwards, the pin-in-slot 449 causes the locking bolt 444 to slide forward until it engages the front leg stem 442, preventing the front leg 446 from moving any further.

In FIG. 31b, the level finding frame assembly 440 lowers onto a set of steps. When the main portion 441 descends, the front leg 446 makes contact with level 82 first. When the lower leg 447 eventually makes contact with level 81, the locking bolt 444 engages and locks the front leg 446 into position. The step frame 440 is now in static equilibrium.

FIG. 32a depicts another embodiment of the level finding frame assembly 540 consisting of a main body portion 541 and a rotating overhanging portion 542, which rotates relative to the main body portion 541 by means a pivot feature 543. The rotating overhanging portion 542 is free to rotate until a locking bolt 544 slides upwards and engages a clamping surface 552. Lower moving leg 547 is free to move vertically relative to the main body portion 541. When not under load, moving leg 547 is kept extended by spring 545. Lower moving leg 547 is rigidly connected to locking bolt 544 by stem 553 which passes through end-stop 554. The lower-most position of both the moving leg 547 and the rotating overhanging portion 542 are limited by the end-stop 554.

In FIG. 32b, the level finding frame assembly 540 lowers onto a set of steps. When the main portion 541 descends, the rotating overhanging portion 542 makes contact with level 82 first. When the lower leg 547 eventually makes contact with level 81, the locking bolt 544 engages and locks the rotating overhanging portion 542 into position. The step frame 540 is now in static equilibrium.

FIG. 33a depicts another embodiment of the level finding frame assembly 940 consisting of a main body portion 941 and an articulated front leg 942 consisting of a two-body linkage. The forward link of the articulated front leg 942 is attached to the main body portion 941 by first pin 955 while the rear link is attached to locking bar 944 that slides horizontally relative to the main body portion 941. The articulated front leg 942 is free to move until the top point 954 of stem 953 engages the clamping surface 952 of the locking bar 942. Stem 953 is rigidly attached to lower moving leg 947, which is free to move vertically relative to the main body portion 941. When not under load, moving leg 947 is kept extended by spring 945.

In FIG. 33b, the level finding frame assembly 940 lowers onto a set of steps. When the main portion 941 descends, the articulated front leg 942 makes contact with level 82 first. When the lower leg 947 eventually makes contact with level 81, stem 953 engages the locking bolt 944 engages and locks the articulated front leg 942 into position. The step frame 940 is now in static equilibrium.

It is to be appreciated that the level finding embodiments shown above are mechanical linkages. Equivalent concepts may be implemented using electro-mechanical switches and actuators to trigger the locking mechanisms when the frames have made contact with the step levels.

Multiple Steps

The step frame design is not limited to ascending or descending single steps at a time. In the embodiment shown in FIG. 34a, an embodiment of the frame assembly 840 is shown which may be configured to traverse multiple steps in a single cycle, as shown in FIG. 34b. In particular, the main body portion 842 has an overhanging arm 844 extending at a height that is at least greater than the height of two or more stair steps.

Payload Body Embodiments
Payload Body Configurations

In addition to the embodiments of payload body 12 disclosed above, FIGS. 35a to 35d show further alternative embodiments of the payload body 12:

FIG. 35a depicts a semi-autonomous mobile robot where payload body 12 contains motorized actuators and control logic that control the movement of the wheels 20;

FIG. 35b depicts a tele-operated treaded vehicle where the movement of the movement support 20, in the form of tracks, are controlled remotely by an operator;

FIG. 35c depicts a manually steered hand cart, which may attach to either a motorized mechanism or a manually operated mechanism powered by a hand crank;

FIG. 35d depicts a wheelchair.

Wheel Configurations

FIGS. 36a to 36d depict alternative movement support configurations 20 for various embodiments of the payload body 12.

FIG. 36a shows a wheel configuration 20 consisting of pairs of fixed-direction wheels 2010 and swivel casters 2020, each pair having comparable diameters.

The wheel configuration depicted in FIG. 36b comprises pairs of wheels of dissimilar diameters, including a pair of omni-directional roller casters 2030, a pair of large wheels 2040 and a pair of small pilot wheels 2050 that are part of an edge-detection system (as discussed below).

FIG. 36c shows a configuration that, in addition to the main support wheels and casters, also contains a pair of auxiliary stabilizing wheels 2060 that prevents the payload body 12 from pitching forward when its casters are pointed inward, and a pair of outrigger wheels 2070.

FIG. 36d illustrates how the outrigger wheels 2070 add further stability when the payload body 12 is traversing the floor 90, and may also function as pilot wheels in an edge detection braking system while on the step 80 (as discussed below).

Edge Detection Brakes

The present invention may include a braking feature to prevent undesired wheel movement, in particular when wheels are near the edge of a step.

FIG. 37a shows a preferred embodiment of a braking assembly 100 attached to one leading wheel 101. In this embodiment, the braking assembly body 102 rigidly attaches to the payload body 12 and provides an attachment point for the wheel axle 103. A first brake pad 104 is manually or electromechanically actuated to prevent wheel 101 from rotating in general. A second brake pad 105 is configured to be actuated when the wheel 101 approaches the edge 84 of a step 80. The second brake pad 105 is attached to one end of a pivot arm 106, which pivots about a pin 107. A pilot wheel 108 is attached to the other end of the pivot arm 106. A spring (hidden) biases the pivot arm to rotate clockwise, pressing the pilot wheel against the surface 82 on which the payload body 12 is resting.

FIG. 37b shows a payload body 12 equipped with the braking assembly 100 approaching an edge 84. The first brake pad 104 remains disengaged, allowing the payload body 12 to roll freely on surface 82. If leading wheel 101 is sufficiently far from edge 84, the second brake pad 105 remains disengaged. However, once wheel 101 is close enough to allow pilot wheel 108 to move over the edge 84, the second brake pad 105 engages with wheel 101, preventing any further movement of the payload body 12.

FIG. 37c shows an alternative embodiment of the edge detection brake. In this embodiment, the second brake pad 105 is incorporated into the pivot arm, and the pilot wheel 108 is comparable in size with the lead wheel 101. When pilot wheel 108 moves over the step edge, brake pad 105 engages with wheel 101, against either its tread or another feature such as it axle, to prevent further movement.

Other embodiments of the braking feature 100 are possible, such as an embodiment in which the edge-probing arm 102 causes a friction pad to engage with the surface of the step, preventing further motion. Other possible embodiments include electro-mechanical versions that use a combination of edge-detection sensors, actuators and control logic to the same effect.

Preferred and Alternative Embodiments of the Device

As any person skilled in the art may appreciate, it is possible to assemble a stair traversing device that is consistent with the scope of the invention by combining various alternative embodiments of the constituent sub-assemblies and attributes. In particular, different payload bodies (e.g., robot, vehicle, hand-truck, wheel-chair) may be combined with different step frames assemblies (e.g., single-body vs. multi-bodied, fixed geometry, variable geometry, foldable, etc.) and different mechanisms (e.g., crank-arm, non-rotating hub, chain-loop, rack-and-pinion, etc.).

FIG. 38 shows one preferred embodiment of the stair traversing device 10 in the form of a service robot comprising a payload body 12 similar to the one depicted in FIG. 35a, a step frame 14 similar to the one shown in FIG. 26a, and a mechanism 16 similar to that depicted in FIG. 14.

FIG. 39 depicts another preferred embodiment of the stair traversing device 10 in the form of a manually steered hand cart comprising a payload body 12 similar to the one depicted in FIG. 35c, a step frame 14 similar to the one shown in FIG. 26b and a non-rotating hub-type mechanism 14 similar to that depicted in FIG. 21. This embodiment is moved from place to place by a human operator.

In FIG. 40, another embodiment 500 of a hand cart version of the stair traversing device is shown, similar to the one depicted in FIG. 39, which uses a manually powered crank 504 rather than a motor to turn the shaft 502 that drives the mechanism 16.

In alternative embodiments, the configuration of the payload body relative to the step frame and the mechanism may vary. In the embodiments shown in the designs disclosed above, the stair traversing device employs a step frame consisting of two symmetric bodies on either side of the payload body.

As shown in FIG. 41, however, the present invention may also be implemented using a step frame consisting of a single central body instead of the designs with two symmetric bodies disclosed above. The stair traversing device 300 comprises a payload body 302 that is a three-sided rectangular frame with a hollowed center. Mechanism 14 is rigidly connected to the inner surfaces of the two vertical sides 304 and 306 of the payload body 302. A frame assembly consisting of a single central body 308 is attached, on both sides to the two mechanisms 14 through two bores 310 on either side. The single central body 308 may be of increased width with multiple support feet 309 attached to the overhanging portion 312 and the bottom of the frame assembly. In addition, the height of the single central body 308 is to be less than the interior height of the payload body 302 such that when the single central body 308 is raised to its highest point during the cyclical motion it would not contact the top portion of the payload body 302.

Method of Climbing a Stair

It is also disclosed a method for traversing a stair using a stair traversing device as described herein and comprising a payload body for transporting a payload, a step frame, and a mechanism between the step frame and the payload body. The method comprises using the mechanism to move one of a payload body and a step frame with regards to another one of the payload body and the step frame along a cyclical path from a retracted configuration in which the payload body and the step frame are both on a first level of the stair to an extended configuration in which the payload body and the step frame are on two different levels of the stair.

The method further comprises moving the other one of the payload body and the step frame along the cyclical path back in the retracted configuration in which both the payload body and the step frame are on a second level of the stair.

The method comprises the step of concurrently maintaining a relative orientation between the payload body and the stair during any climbing or descending movement. Accordingly, the payload will remain stable on the payload body through the stair. This step may be performed using the non-rotating carriage assembly, the non-rotating hub assembly or the non-rotating connection assembly.

To adapt to a plurality of step dimensions, the method may comprise the step of adjusting the step frame to conform to said step dimensions using a variable geometry step frame.

The method may further comprise the step of engaging a driving shaft pivotally mounted to the payload body and to the mechanism. As explained herein above, the driving shaft may be engaged by a motorized actuator, such as but not limited to an electric motor. The driving shaft may also be engaged by human power through a dedicated mechanism.

In some situation, it may be necessary to preclude the payload body to go rearward using a breaking assembly when it is adjacent to the stair to avoid accident. Embodiments of breaking assemblies are described herein above.

The scope of the present invention should not be limited by the preferred embodiments set forth in the examples, but should be given the broadest interpretation consistent with the description as a whole.

The invention claimed is:

1. A stair traversing device, comprising:
a payload body configured for transporting a payload;
a step frame; and
a mechanism between the step frame and the payload body,
the mechanism being configured to move the step frame with regards to the payload body along a cyclical path by:
driving a movement of one of the payload body and the step frame relative to the other one of the payload body and the step frame along a first segment of the cyclical path from a retracted configuration in which the step frame and the payload body are both on a first level, to an extended configuration in which the step frame and the payload body are on two different levels; and
driving a movement of the other one of the payload body and the step frame along a second segment of the cyclical path back into the retracted configuration in which the step frame and the payload body are both on a second level;
wherein the step frame is configured to remain on the first or second level when the payload body is moved between the first level and the second level;
wherein the mechanism is configured to maintain the relative orientation between the payload body and the step frame; and
wherein the mechanism comprises an engaging portion operatively connected to the one of the payload body and the step frame, and a receiving portion, engaged by the engaging portion, the receiving portion being operatively connected to the other one of the payload body and the step frame, the mechanism moving the engaging portion relative to the receiving portion along the first segment of the cyclical path in which the engaging portion moves from a first position to a second position by passing by a first intermediate position, the mechanism moving the engaging portion relative to the receiving portion along the second segment of the cyclical path in which the engaging portion moves from the second position back to the first position by passing by a second intermediate position, the first intermediate position being offset from the second intermediate position.

2. The stair traversing device according to claim 1, wherein the payload body and the step frame are both configured to remain in position on the first or second level when the other one of the payload body and the step frame is moved between the first level and the second level.

3. The stair traversing device according to claim 1, wherein the mechanism further comprises a non-rotating carriage assembly, and wherein a shape of the step frame conforms to a shape of a step of the stair.

4. The stair traversing device according to claim 3, wherein the non-rotating carriage assembly comprises vertical rails moving integrally with the payload body, a horizontal rail moving integrally with the step frame, and a carriage disposed between the vertical rails and the horizontal rail, the carriage being in sliding engagement with the vertical rails and the horizontal rail thereby allowing the step frame to move in a vertical direction and in a horizontal direction relative to the payload body.

5. The stair traversing device according to claim 4, wherein the carriage pivotally receives vertical rollers engaging the vertical rail and horizontal rollers engaging the horizontal rails.

6. The stair traversing device according to claim 1, wherein the mechanism further comprises a non-rotating connection assembly, and wherein a shape of the step frame conforms to a shape of a step of the stair.

7. The stair traversing device according to claim 6, wherein the non-rotating connection assembly comprises carriages slidingly received within rails moving integrally with the payload body, the carriages each defining a guide slot extending along a direction perpendicular to the rails, each of the guide slots slidingly receiving a lug having a shape matching a shape of the guide slot for allowing translation and precluding rotation, the lug and the step frame moving integrally.

8. The stair traversing device according to claim 7, wherein the mechanism comprises chain loops moving with the payload body, each chain loop being mounted around a plurality of sprockets pivotally mounted to the mechanism, one of the plurality of sprockets being drivingly engaged by a driving shaft protruding from the payload body, wherein the engaging portion are pins rigidly connected to the chain loops for moving there around thereby defining the cyclical path, and wherein the receiving portion are apertures defined in the lugs for pivotally receiving the pins, the pins rotating relative to the lugs about an axis parallel to the driving shaft.

9. The stair traversing device according to claim 8, wherein step frame engaging portion are rigidly connected to the lugs.

10. The stair traversing device according to claim 9, wherein the step frame engaging lugs are square lugs and wherein the step frame defines square bores each having a shape matching a shape of the square lugs for precluding rotation.

11. The stair traversing device according to claim 8, wherein the driving shaft is engaged by an electric motor disposed within the payload body.

12. A method for traversing a stair using a stair traversing device, the device comprising:
   a payload body configured for transporting a payload;
   a step frame; and
   a mechanism between the step frame and the payload body, the method comprising, with the mechanism:
   a) moving one of a payload body and a step frame with regards to another one of the payload body and the step frame along a cyclical path from a retracted configuration in which the payload body and the step frame are both on a first level of the stair to an extended configuration in which the payload body and the step frame are on two different levels of the stair;
   b) moving the other one of the payload body and the step frame along the cyclical path back to the retracted configuration in which both the payload body and the step frame are on a second level of the stair; and
   c) maintaining a relative orientation between the payload body and the stair during steps a) and b),
   wherein the method includes adjusting the step frame to dimensions of the steps of the stair using a variable geometry step frame.

13. A method for traversing a stair using a stair traversing device, the device having a payload body configured for transporting a payload, a step frame, and a mechanism between the step frame and the payload body, the method comprising, with the mechanism:
   a) moving one of a payload body and a step frame with regards to another one of the payload body and the step frame along a cyclical path from a retracted configuration in which the payload body and the step frame are both on a first level of the stair to an extended configuration in which the payload body and the step frame are on two different levels of the stair
   b) moving the other one of the payload body and the step frame along the cyclical path back to the retracted configuration in which both the payload body and the step frame are on a second level of the stair; and
   c) maintaining a relative orientation between the payload body and the stair during steps a) and b),
   wherein the method includes precluding the payload body from rolling backward using a braking assembly when the payload body is adjacent to the edge of a step of the stair.

14. A stair traversing device, comprising:
   a payload body configured for transporting a payload;
   a step frame having a shape conforming to a shape of a step of the stair; and
   a mechanism between the step frame and the payload body,
   the mechanism being configured to move the step frame with regards to the payload body along a cyclical path by:
   driving a movement of one of the payload body and the step frame relative to the other one of the payload body and the step frame along a first segment of the cyclical path from a retracted configuration in which the step frame and the payload body are both on a first level, to an extended configuration in which the step frame and the payload body are on two different levels; and
   driving a movement of the other one of the payload body and the step frame along a second segment of the cyclical path back into the retracted configuration in which the step frame and the payload body are both on a second level;

wherein the step frame is configured to remain on the first or second level when the payload body is moved between the first level and the second level; and wherein the mechanism is configured to maintain the relative orientation between the payload body and the step frame.

* * * * *